(12) United States Patent
Jensen et al.

US012281091B1

(10) Patent No.: US 12,281,091 B1
(45) Date of Patent: Apr. 22, 2025

(54) METHODS OF PREPARING CANNABINOIDS OR DERIVATIVES THEREOF

(71) Applicant: FloraScience Inc., Milwaukie, OR (US)

(72) Inventors: Robert Paul Jensen, Portland, OR (US); Vaughn Hartung, Milwaukie, OR (US)

(73) Assignee: FloraScience Inc., Milwaukie, OR (US)

( * ) Notice: Subject to any disclaimer, the term of this patent is extended or adjusted under 35 U.S.C. 154(b) by 0 days.

(21) Appl. No.: 18/739,493

(22) Filed: Jun. 11, 2024

Related U.S. Application Data

(63) Continuation of application No. 18/403,509, filed on Jan. 3, 2024.

(51) Int. Cl.
*C07D 311/80* (2006.01)
*B01J 27/06* (2006.01)
*C07D 307/91* (2006.01)

(52) U.S. Cl.
CPC ............. *C07D 311/80* (2013.01); *B01J 27/06* (2013.01); *C07D 307/91* (2013.01)

(58) Field of Classification Search
CPC .................................................. C07D 311/80
USPC ........................................................ 549/390
See application file for complete search history.

(56) References Cited

U.S. PATENT DOCUMENTS

| | | | |
|---|---|---|---|
| 2022/0162180 A1 | 5/2022 | Opperman et al. | |
| 2023/0373942 A1* | 11/2023 | Berkowitz | ........... A61K 31/352 |
| 2024/0261302 A1 | 8/2024 | Jensen et al. | |

FOREIGN PATENT DOCUMENTS

WO    WO 2020/252277    12/2020

OTHER PUBLICATIONS

Nguyen et al., J. Nat. Prod. (2022) 85:1555-68. Submitted by applicant in U.S. Appl. No. 18/403,509.*
Adams et al., "Structure of Cannabidiol. VI. Isomerization of Cannabidiol to Tetrahydrocannabinol, a Physiologically Active Product. Conversion of Cannabidiol to Cannabinol 1," Journal of American Chemical Society, Sep. 1940, 62(9):2402-2405.
Caprioglio et al., "One-Pot Total Synthesis of Cannabinol via Iodine-Mediated Deconstructive Annulation," Organic Letters, Jul. 2019, 21(15):6122-6125.
Davis et al., "Protein kinase C activation inhibits glutamate-induced cytotoxicity in a neuronal cell line," Brain Research, Jul. 1994, 652(1):169-173.
Ghosh et al., "Cannabis indica. Part V. The synthesis of cannabinol," Journal of the Chemical Society (Resumed), 1940, 1393-1396.
Levine, "Origin of Cannabinol," Journal of American Chemical Society, 1944, 66(11):1868-1870.
Mechoulam et al., "Hashish. XII. Stereoelectronic factor in the chloranil dehydrogenation of cannabinoids. Total synthesis of dl-cannabichromene," Journal of American Chemical Society, Apr. 1968, 90(9):2418-2420.
Meltzer et al., "An Improved Synthesis of Cannabinol and Cannabiorcol," Synthesis, Dec. 1981, (12): 985-987.
Pollastro et al., "Iodine-Promoted Aromatization of p-Menthane-Type Phytocannabinoids," J. Nat. Prod., Dec. 2018, 81(3):630-633.
International Search Report and Written Opinion in International Appln. No. PCT/US2024/010195, mailed on Jul. 2, 2024, 21 pages.
Nguyen et al., "Synthetic Strategies for Rare Cannabinoids Derived from Cannabis sativa," Journal of Natural Products, Jun. 2022, 85:1555-1568.

* cited by examiner

*Primary Examiner* — Taofiq A Solola
(74) *Attorney, Agent, or Firm* — Fish & Richardson P.C.

(57) ABSTRACT

Provided are methods of preparing cannabinoids and cannabinoid derivatives and compositions containing the cannabinoids and derivatives.

29 Claims, 4 Drawing Sheets

METHODS OF PREPARING CANNABINOIDS OR DERIVATIVES THEREOF

CLAIM OF PRIORITY

This application claims priority to U.S. patent application Ser. No. 18/403,509, filed on Jan. 3, 2024, the entire contents of which are hereby incorporated by reference.

TECHNICAL FIELD

This disclosure relates to methods of preparing cannabinoids or derivatives thereof and compositions including two or more cannabinoids or derivatives thereof.

BACKGROUND

Many cannabinoids are produced via metabolic processes of the *cannabis* plant; however, cannabinol (CBN) is different. CBN is not produced by the metabolic processes of the *cannabis* plant, as there is no enzyme that can produce CBN in a high-fidelity transformation. It has been understood since 1944 that CBN is produced naturally by non-enzymatic oxidation of tetrahydrocannabinol (THC) (Levine, *J. Am. Chem. Soc.* 1944, 66 (11), 1868-1870), a process that is slow and cannot generate CBN in high enough abundance to become the dominant cannabinoid in biomass. Thus, while some cultivars of *Cannabis sativa* can produce extracts and distillates with very high levels of cannabidiol (CBD) and THC, it is not feasible to do so with CBN. Traditional horticultural methods of optimizing cannabinoid expression are not practically useful for cannabinoids such as CBN, cannabinodiol (CBND), and cannabifuran (CBF) which are not made by enzymatic processes. While THC can transform into CBN, the lack of any enzyme known to catalyze the transformation also means that traditional industrial biosynthesis approaches are not practical methods of generating CBN in high purity. One of the ways that CBN can be generated in high yield and with high purity is by beginning with a purified cannabinoid as a starting material and performing a synthetic oxidation reaction, a method sometimes referred to as "partial synthesis." In the chemical literature there exist at least six examples of CBN being generated by a controlled synthetic oxidation of a cannabinoid compound (see, e.g., Adams et al., J. Am. Chem. Soc. (1940) 62(9):2402-2405; Ghosh et al., J. Chem. Soc. Resumed (1940) No. 0:1393-1396; Mechoulam et al., J. Am. Chem. Soc. (1968) 90(9):2418-2420; Meltzer et al., Improv. Synth. Cannabinol Cannabiorcol (1981); Pollastro et al., J. Nat. Prod. (2018) 81(3):630-633; and Caprioglio et al., Org. Lett. (2019) 21(15):6122-6125. However, none of these methods constitute a scalable means of producing CBN due to a variety of reasons including their use of toxic solvents, formation of undesirable byproducts, high temperatures, expensive reagents, or other peculiarities which limit the practicality of these methods to below the kilogram scale.

SUMMARY

Provided in the present disclosure are methods of preparing cannabinoids and cannabinoid derivatives, and compositions thereof.

Provided is a method of preparing cannabinol, or a pharmaceutically acceptable salt thereof, the method comprising admixing a catalyst, cannabidiol, and an oxidizing agent to form cannabinol, or a pharmaceutically acceptable salt thereof, wherein the catalyst is $I_2$, $Br_2$, or $Cl_2$.

In some embodiments, the admixing comprises (a) reacting the catalyst and the cannabidiol to form tetrahydrocannabinol; and (b) reacting the tetrahydrocannabinol, the catalyst, and the oxidizing agent to form the cannabinol, or a pharmaceutically acceptable salt thereof.

In some embodiments, the catalyst is $I_2$.

In some embodiments, reacting the catalyst and the cannabidiol is performed at a temperature of about 35° C. to about 200° C., about 50° C. to about 150° C., about 50° C. to about 100° C., or less than about 100° C.

In some embodiments, the admixing is done in the presence of a solvent.

In some embodiments, the solvent comprises one or more of benzene, toluene, xylenes, mesitylene, anisole, acetonitrile, acetic acid, acetic anhydride, heptane, cyclohexane, pyridine, chloroform, isopropyl acetate, dimethyl sulfoxide, dimethylformamide, dimethylacetamide, N-methylpyrrolidone, and chlorobenzene.

In some embodiments, the catalyst is present in an amount of about 10 mol % or less, about 5 mol % or less, or about 1 mol % or less, based on the total mols of cannabidiol.

In some embodiments, the reacting the tetrahydrocannabinol, the catalyst, and the oxidizing agent is performed at a temperature in a range of about 50° C. to about 250° C., about 75° C. to about 200° C., about 120° C. to about 170° C., or less than about 150° C.

In some embodiments, the oxidizing agent comprises one or more of $O_2$, $S_8$, benzoquinone, chloranil, hydrogen peroxide, peracetic acid, diacetyl peroxide, ditertbutyl peroxide, dicumyl peroxide, peroxybenzoic acid, benzoyl peroxide, and dimethyl sulfoxide. In some embodiments, the oxidizing agent comprises $O_2$ and an inert gas. In some embodiments, the oxidizing agent comprises $O_2$ and $N_2$. In some embodiments, the oxidizing agent comprises $O_2$ and the $O_2$ is present in an amount of less than about 25 wt %, less than about 20 wt %, less than about 15 wt %, about 10 wt % to about 20 wt %, or about 1 wt % to about 10 wt %, based on the total weight of the oxidizing agent.

In some embodiments, step (a) and step (b) are performed in situ.

In some embodiments, the method is performed in a single vessel.

In some embodiments, the method further forms cannabifuran, and wherein the cannabifuran is formed in an amount of less than about 5 mol %, based on the total mols of cannabinol, or a pharmaceutically acceptable salt thereof.

In some embodiments, the method further comprises crystallizing the cannabinol, or a pharmaceutically acceptable salt thereof.

In some embodiments, the cannabinol, or a pharmaceutically acceptable salt thereof, has a purity of about 90% or more, about 95% or more, or about 99% or more.

In some embodiments, the cannabinol, or a pharmaceutically acceptable salt thereof, is substantially free of $\Delta^{(9\text{-}10)}$-tetrahydrocannabinol.

In some embodiments, the cannabinol, or a pharmaceutically acceptable salt thereof, is substantially free of $\Delta^{(8,9)}$-tetrahydrocannabinol and $\Delta^{(9\text{-}10)}$-tetrahydrocannabinol.

In some embodiments, the method further comprises admixing the cannabinol, or a pharmaceutically acceptable salt thereof, with a dehydrating agent and acetic acid to form a mixture comprising acetylcannabinol, or a pharmaceutically acceptable salt thereof.

In some embodiments, the dehydrating agent comprises one or more of acetic anhydride, phosphoric acid, sulfuric acid, sodium bisulfite, phosphorus pentoxide, and polyphosphoric acid.

In some embodiments, the mixture further forms acetylcannabifuran, or a pharmaceutically acceptable salt thereof, wherein the acetylcannabifuran, or a pharmaceutically acceptable salt thereof, is formed in an amount of less than about 5 mol %, based on the total mols of acetylcannabinol.

Provided is a method of preparing cannabinol, or a pharmaceutically acceptable salt thereof, the method comprising admixing a catalyst, an oxidizing agent, and tetrahydrocannabinol to form cannabinol, or a pharmaceutically acceptable salt thereof, wherein the catalyst is $I_2$, $Br_2$, or $Cl_2$.

In some embodiments, the tetrahydrocannabinol is prepared by a process comprising admixing the catalyst and cannabidiol to form the tetrahydrocannabinol.

In some embodiments, admixing the catalyst and the cannabidiol is performed at a temperature of about 35° C. to about 200° C., about 50° C. to about 150° C., about 50° C. to about 100° C., or about less than about 100° C.

Provided is a method of preparing cannabinol, or a pharmaceutically acceptable salt thereof, the method comprising (a) admixing cannabidiol and a catalyst to form a mixture of $\Delta^{(8-9)}$-tetrahydrocannabinol and $\Delta^{(9-10)}$-tetrahydrocannabinol; and (b) admixing the mixture and an oxidizing agent to form the cannabinol, or a pharmaceutically acceptable thereof.

In some embodiments, the catalyst is $I_2$. In some embodiments, the $I_2$ is present in an amount of less than about 5 mol %, based on the total mols of the cannabidiol.

In some embodiments, the catalyst is present in an amount of less than about 1 mol %, based on the total mols of the cannabidiol.

In some embodiments, the cannabinol has a purity of about 90% or more, about 95% or more, or about 99% or more.

Provided is a method of preparing acetylcannabinol, or a pharmaceutically acceptable salt thereof, the method comprising admixing cannabidiol, an oxidizing agent, $I_2$, and acetic acid to form a mixture comprising cannabinol, or a pharmaceutically acceptable salt thereof and admixing the mixture with a dehydrating agent to form acetylcannabinol, or a pharmaceutically acceptable salt thereof.

In some embodiments, the $I_2$ is present in an amount of less than about 5 mol %, based on the total mols of cannabidiol. In some embodiments, the $I_2$ is present in an amount of less than about 1 mol %, based on the total mols of cannabidiol.

In some embodiments, the acetylcannabinol has a purity of about 90% or more, about 95% or more, or about 99% or more.

The details of one or more embodiments of the subject matter of this disclosure are set forth in the accompanying drawings and the description. Other features, aspects, and advantages of the subject matter will become apparent from the description, the drawings, and the claims.

DETAILED DESCRIPTION

Figure 1:
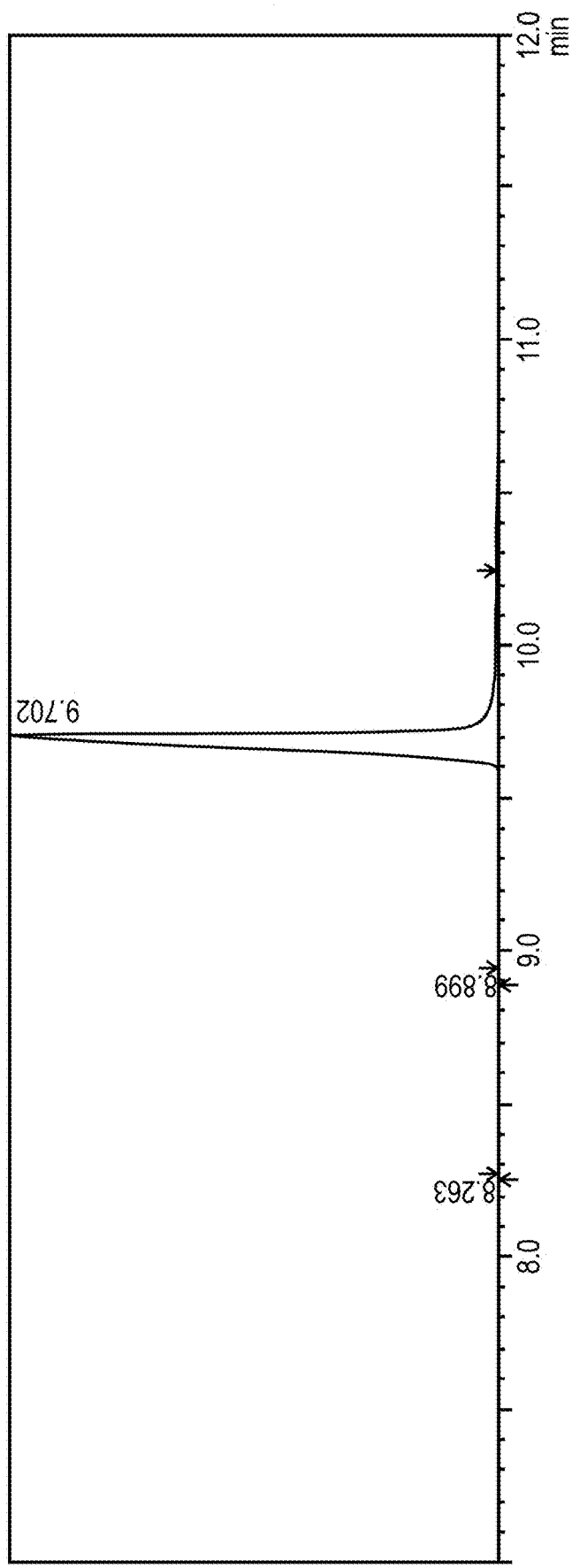
FIG. 1 is a gas chromatography-mass spectrometry (GCMS) spectrum of the CBN of the disclosure.

Provided in the present disclosure are methods for the catalytic conversion of cannabinoid compounds into cannabinoid oxidation products. The methods of the present disclosure are scalable and generate the cannabinoid oxidation products in high yield and with high purity. In some embodiments, the cannabinoid is a compound of Formula (I), or a pharmaceutically acceptable salt thereof. Thus, provided in the present disclosure are methods of preparing a cannabinoid (e.g., a compound of Formula (I)), or a pharmaceutically acceptable salt thereof, the method including admixing a catalyst, a cannabinoid precursor, and an oxidizing agent to form the cannabinoid (a compound of Formula (I)), or a pharmaceutically acceptable salt thereof. In some embodiments, the cannabinoid precursor is cannabidiol. Compared with other known methods of preparing cannabinoids, the methods disclosed herein have one or more advantages. For example, the methods disclosed herein are scalable methods that can produce large quantities in high yield of high quality, high purity, cannabinoid. In some embodiments, the cannabinoid is a compound of Formula (I), or a pharmaceutically acceptable salt thereof. Specifically, producing the cannabinoid CBN (cannabinol) that is substantially free of other cannabinoids has previously proven difficult because other cannabinoids with structural similarities can co-crystallize with the CBN. For example, isomers of THC, such as delta-8-THC and delta-9-THC, can co-crystallize with CBN. Since THC isomers can co-crystallize with CBN and cannot easily be separated away from crude CBN by crystallization, they must be completely reacted away during the synthesis. The methods disclosed herein can accomplish just that because it is a method having high fidelity and producing very few side products. Advantageously, the methods disclosed herein can produce a cannabinoid in high enough yield to allow for crystallization as an isolation method and in turn, avoid any chromatography methods. The methods disclosed herein can generate a cannabinoid with both high purity and in high yield and minimize side products both in number and abundance. In some embodiments, the cannabinoid is a compound of Formula (I), or a pharmaceutically acceptable salt thereof.

The methods disclosed herein advantageously maximize scalability in one or more ways, such as by using gentle conditions, using inexpensive solvents and reagents, and producing manageable by-products and waste. The methods disclosed herein advantageously minimize cost by using the fewest possible number of total steps, and each discreet step in the synthesis can occur sequentially in one pot without excessive workup or purification steps (e.g., chromatography, etc.) in between each step. For example, the methods of the present disclosure utilize only catalytic amounts of a halogen (such as $I_2$, $Br_2$, or $Cl_2$) to catalyze the conversion of cannabinoid compounds into cannabinoid oxidation products, whereas known reactions typically utilize stoichiometric amounts of the same halogen. Similarly, the methods of the present disclosure utilize only catalytic amounts of an oxidizing agent to catalyze the conversion of cannabinoid compounds into cannabinoid oxidation products, whereas known reactions typically utilize stoichiometric amounts of the same oxidizing agent.

The methods of the present disclosure also provide an environmentally friendly method of producing cannabinoid products due to the small amount of toxic chemicals utilized and the byproducts produced. For example, the methods of the present disclosure produce water and only trace amounts of a halogen hydride (e.g., HI, HBr, HCl) as byproducts. This is because the method of the present disclosure employs a homogeneous catalyst in the dehydrogenation step that can be regenerated in situ by the oxidizing agent. This can lead to high quality cannabinoid products, where the cannabinoid is abundant enough in the crude product to be easily refined by crystallization. In some embodiments, the method can fully deplete all THC isomer intermediates until they are no longer detectable, including by sensitive analytical methods.

Also provided are methods of producing oxidative degradation cannabinoid products, including cannabinoid compounds that are not produced by enzymatic activity in the *cannabis* plant. The methods of synthesizing such compound provided in the present disclosure can be performed in only two steps, whereas known methods of producing these compounds require multiple steps, some having at least six steps.

Definitions

Unless otherwise defined, all technical and scientific terms used in this document have the same meaning as commonly understood by one of ordinary skill in the art to which the present application belongs. Methods and materials are described in this document for use in the present application; other, suitable methods and materials known in the art can also be used. The materials, methods, and examples are illustrative only and not intended to be limiting. All publications, patent applications, patents, sequences, database entries, and other references mentioned in this document are incorporated by reference in their entirety. In case of conflict, the present specification, including definitions, will control.

Values expressed in a range format should be interpreted in a flexible manner to include not only the numerical values explicitly recited as the limits of the range, but also to include all the individual numerical values or sub-ranges encompassed within that range as if each numerical value and sub-range is explicitly recited. For example, a range of "about 0.1% to about 5%" or "about 0.1% to 5%" should be interpreted to include not just about 0.1% to about 5%, but also the individual values (for example, 1%, 2%, 3%, and 4%) and the sub-ranges (for example, 0.1% to 0.5%, 1.1% to 2.2%, and 3.3% to 4.4%) within the indicated range. The statement "about X to Y" has the same meaning as "about X to about Y," unless indicated otherwise. Likewise, the statement "about X, Y, or about Z" has the same meaning as "about X, about Y, or about Z," unless indicated otherwise.

The term "about," as used in this disclosure, can allow for a degree of variability in a value or range, for example, within 5%, or within 1% of a stated value or of a stated limit of a range.

As used in this disclosure, the terms "a," "an," and "the" are used to include one or more than one unless the context clearly dictates otherwise. The term "or" is used to refer to a nonexclusive "or" unless otherwise indicated. The statement "at least one of A and B" has the same meaning as "A, B, or A and B." In addition, it is to be understood that the phraseology or terminology employed in this disclosure, and not otherwise defined, is for the purpose of description only and not of limitation. Any use of section headings is intended to aid reading of the document and is not to be interpreted as limiting; information that is relevant to a section heading may occur within or outside of that particular section.

In the methods described in this disclosure, the acts can be carried out in any order, except when a temporal or operational sequence is explicitly recited. Furthermore, specified acts can be carried out concurrently unless explicit claim language recites that they be carried out separately. For example, a claimed act of doing X and a claimed act of doing Y can be conducted simultaneously within a single operation, and the resulting process will fall within the literal scope of the claimed process.

As used herein, the term "cannabinoid" refers to a compound that is structurally related to the terpophenolic compounds metabolically produced by *Cannabis sativa*. Cannabinoids include the endocannabinoids (produced naturally in the body by humans and animals), the phytocannabinoids (found in *Cannabis* and some other plants), and synthetic cannabinoids. For example, a notable phytocannabinoid is $\Delta^{9(10)}$-tetrahydrocannabinol ($\Delta^{9(10)}$-THC), the primary psychoactive compound of *Cannabis*. Cannabidiol is another major constituent of the plant, representing up to 40% in extracts of the plant resin. There are at least 85 different cannabinoids isolated from *Cannabis*, which exhibit varied effects.

As used herein, the term "tetrahydrocannabinol" or "THC" refers to any molecule which upon removal or loss of four hydrogen atoms will become CBN (e.g., Scheme 1 shows various THC compounds under acidic conditions maintain a dynamic equilibrium and can lead to the conversion to CBN). This includes the (−)-trans-$\Delta^{(9,10)}$-tetrahydrocannabinol isomer having (6aR,10aR) stereochemistry which is found naturally in *Cannabis sativa*, but also includes all stereochemical variants of this molecular scaffold including (−)-cis-$\Delta^{(9,10)}$-tetrahydrocannabinol, (+)-trans-$\Delta^{(9,10)}$-tetrahydrocannabinol, and (+)-cis-$\Delta^{(9,10)}$-tetrahydrocannabinol, as well as double bond isomers including $\Delta^{(8,9)}$-tetrahydrocannabinol, $\Delta^{(9,11)}$-tetrahydrocannabinol, $\Delta^{(10,10a)}$-tetrahydrocannabinol, $\Delta^{(6a,10a)}$-tetrahydrocannabinol, $\Delta^{(6a,7)}$-tetrahydrocannabinol, and $\Delta^{(7,8)}$-tetrahydrocannabinol and any stereochemical variation thereof. Under acidic reaction conditions such as those described in the methods disclosed herein, this also includes CBC, CBT, and a class of cannabinoid compounds known as iso-THCs which includes $\Delta^{(4,8)}$-iso-tetrahydrocannabinol, cis-$\Delta^{(8,9)}$-iso-tetrahydrocannabinol, trans-$\Delta^{(8,9)}$-iso-tetrahydrocannabinol, and $\Delta^{(4,5)}$-iso-tetrahydrocannabinol (e.g., Scheme 1).

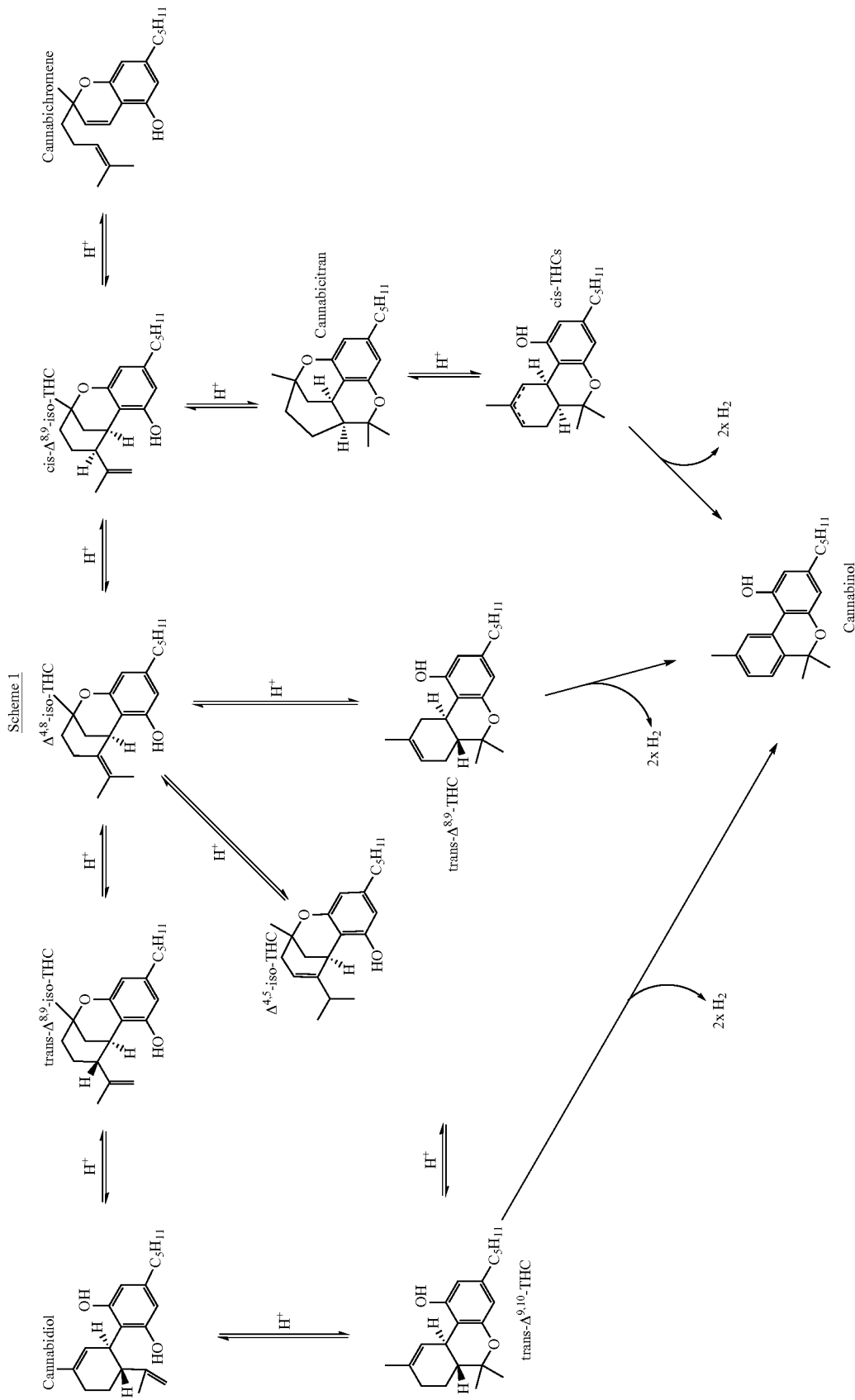

As used herein, the term "high fidelity" refers to a reaction which results in a product ensemble composed of a high amount (e.g., at least 90 mol %, at least 95 mol %, at least 98 mol %, or at least 99 mol %) of the intended product, and having a low number (e.g., less than 3, less than 2, or less than 1) and low abundance (e.g., less than 10 mol %, less than 5 mol %, less than 2 mol %, or less than 1 mol %) of side products.

As used herein, the term "substantially free of" an ingredient(s) as provided throughout the disclosure is intended to mean that the composition or compound(s) contain less than about 0.1 wt % (percent by weight of the total weight of the composition or compound(s)), or insignificant or negligible amounts of said ingredient(s) unless specifically indicated otherwise. In some embodiments, the compound of Formula (I), or a pharmaceutically acceptable salt thereof, of the present disclosure is substantially free of THC, meaning that the compound of Formula (I), or a pharmaceutically acceptable salt thereof, contains less than about 0.1 wt % THC. In some embodiments, the compound of Formula (I), or a pharmaceutically acceptable salt thereof, is CBN, or a pharmaceutically acceptable salt thereof, and is substantially free of THC. In some embodiments, the CBN, or a pharmaceutically acceptable salt thereof, of the present disclosure is substantially free of $\Delta^{9(10)}$-THC, meaning that the CBN, or a pharmaceutically acceptable salt thereof, contains less than about 0.1 wt % $\Delta^{9(10)}$-THC.

As used herein, the term "alkyl" refers to straight chained and branched saturated hydrocarbon groups containing one to thirty carbon atoms, for example, one to twenty-two carbon atoms, or one to twenty carbon atoms, or one to ten carbon atoms. The term $C_n$ means the alkyl group has "n" carbon atoms. For example, C4 alkyl refers to an alkyl group that has 4 carbon atoms. $C_{1-10}$ alkyl refer to an alkyl group having a number of carbon atoms encompassing the entire range (i.e., 1 to 10 carbon atoms), as well as all subgroups (e.g., 1-10, 2-8, 5-10, 1, 2, 3, 4, 5, 6, 7, 8, 9, and 10 carbon atoms). Nonlimiting examples of alkyl groups include, methyl, ethyl, n-propyl, isopropyl, n-butyl, sec-butyl (2-methylpropyl), t-butyl (1,1-dimethylethyl), 3,3-dimethylpentyl, and 2-ethylhexyl. Unless otherwise indicated, an alkyl group can be an unsubstituted alkyl group or a substituted alkyl group. Unless otherwise indicated, an alkyl group can be an unsubstituted alkyl group or a substituted alkyl group.

The term "alkenyl" refers to straight chain and branched chain groups of hydrocarbons having at least one carbon-carbon double bond. Representative examples include, but are not limited to, ethenyl, 1-propenyl, 2-propenyl (allyl), isopropenyl, 2-methyl-1-propenyl, 1-butenyl, 2-butenyl, and the like. When the compounds of the disclosure contain an alkenyl group, the compound can exist as the pure E (entgegen) form, the pure Z (zusammen) form, or any mixture thereof.

The term "hydroxyalkyl" refers to an alkyl, in which one or more hydrogen atoms have been replaced with hydroxyl.

The term "pharmaceutically acceptable salt" refers to a formulation of a compound that does not cause significant irritation to an organism to which it is administered and does not abrogate the biological activity and properties of the compound.

Cannabinoids

Exemplary cannabinoids that can be used or produced in the methods of the present disclosure are described in Table 1.

TABLE 1

| Cannabinoids | | |
|---|---|---|
| Trivial Name | Structure | IUPAC name |
| Cannabichromene (CBC) | | 2-Methyl-2-(4-methylpent-3-enyl)-7-pentyl-5-chromenol |
| Cannabichromenic acid (CBCA) | | 5-Hydroxy-2-methyl-2-(4-methylpent-3-enyl)-7-pentylchromene-6-carboxylic acid |
| Cannabichromenevarin (CBCV) | | 2-Methyl-2-(4-methylpent-3-enyl)-7-propyl-5-chromenol |

TABLE 1-continued

Cannabinoids

| Trivial Name | Structure | IUPAC name |
|---|---|---|
| Cannabidiol (CBD) | 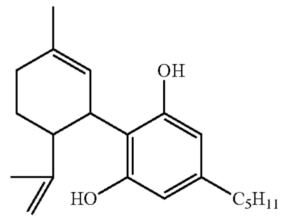 | 2-[(1R,6R)-6-Isopropenyl-3-methylcyclohex-2-en-1-yl]-5-pentylbenzene-1,3-diol |
| 11-Hydroxycannabidiol (11-OH-CBD) | 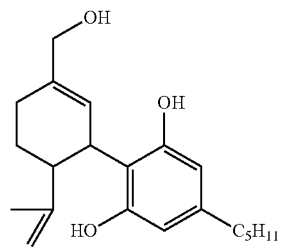 | 5'-(hydroxymethyl)-4-pentyl-2'-(prop-1-en-2-yl)-1',2',3',4'-tetrahydro-[1,1'-biphenyl]-2,6-diol |
| Cannabidiolic acid (CBDA) | 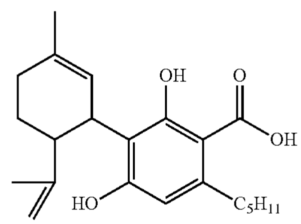 | (1'R,2'R)-2,6-Dihydroxy-5'-methyl-4-pentyl-2'-(prop-1-en-2-yl)-1',2',3',4'-tetrahydro[1,1'-biphenyl]-3-carboxylic acid |
| Cannabidivarol (CBDV) | 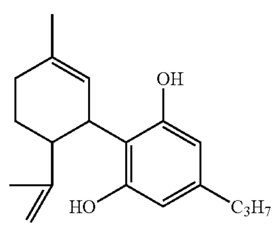 | 2-[(1R,6R)-6-Isopropenyl-3-methylcyclohex-2-en-1-yl]-5-propylbenzene-1,3-diol |
| Cannabielsoin (CBE) | 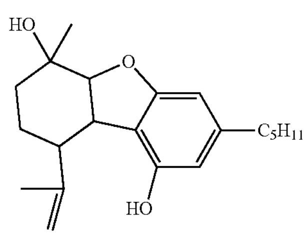 | (5aS,6S,9R,9aR)-6-methyl-3-pentyl-9-prop-1-en-2-yl-7,8,9,9a-tetrahydro-5aH-dibenzofuran-1,6-diol |
| Cannabifuran (CBF) | 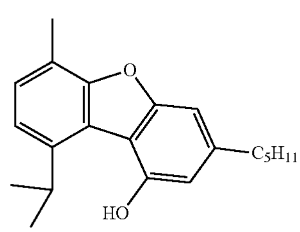 | 5-isopropyl-8-methyl-2-pentyl-9-oxa-4-fluorenol |
| Cannabigerol (CBG) | 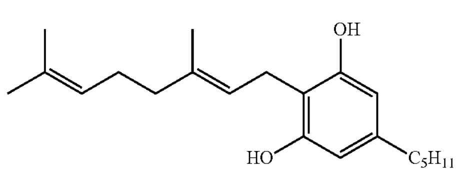 | 2-[(2E)-3,7-Dimethylocta-2,6-dienyl]-5-pentyl-benzene-1,3-diol |

TABLE 1-continued

Cannabinoids

| Trivial Name | Structure | IUPAC name |
|---|---|---|
| Cannabigerolic acid (CBGA) | 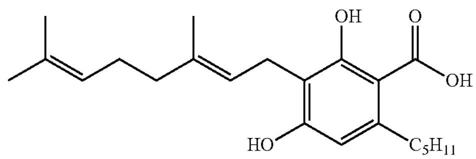 | 3-[(2E)-3,7-Dimethylocta-2,6-dien-1-yl]-2,4-dihydroxy-6-pentylbenzoic acid |
| Cannabigerovarinol (CBGV) | 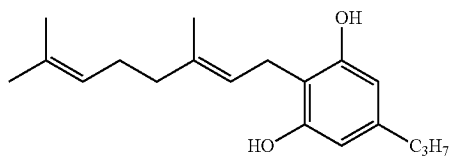 | 2-[(2E)-3,7-Dimethylocta-2,6-dienyl]-5-propyl-benzene-1,3-diol |
| Cannabicyclol (CBL) | 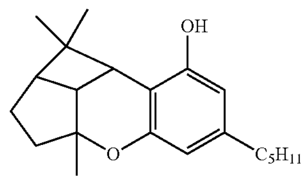 | (1aR-(1a alpha,3a alpha,8b alpha,8calpha))-1a,2,3,3a,8b,8c-hexahydro-1,1,3a-trimethyl-6-pentyl-1H-4-oxabenzo(f)-cyclobut(cd)inden-8-ol |
| Cannabinol (CBN) | 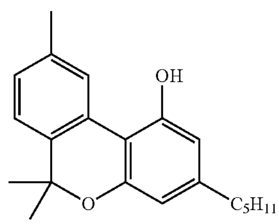 | 6,6,9-Trimethyl-3-pentyl-benzo[c]chromen-1-ol |
| 11-Hydroxycannabinol (11-OH-CBN) | 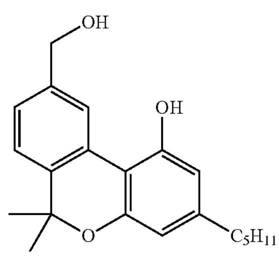 | 9-(hydroxymethyl)-6,6-dimethyl-3-pentyl-6H-benzo[c]chromen-1-ol |
| Cannabinolic acid (CBNA) | 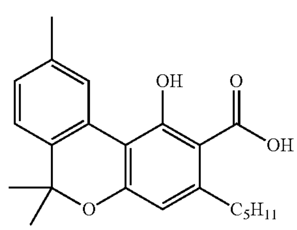 | 1-hydroxy-6,6,9-trimethyl-3-pentyl-benzo[c]chromene-2-carboxylic acid |
| Cannabivarol (CBNV) | 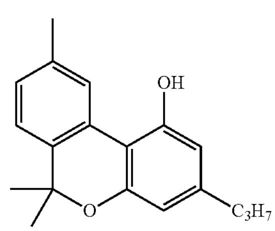 | 6,6,9-trimethyl-3-pentyl-benzo[c]chromen-1-ol |

TABLE 1-continued

| Cannabinoids | | |
|---|---|---|
| Trivial Name | Structure | IUPAC name |
| Acetylcannabinol (CBN-OAc) | | 1-acetoxy-6,6,9-trimethyl-3-pentyl-benzo[c]chromene |
| Methoxycannabinol (CBN-OMe) | | 1-methoxy-6,6,9-trimethyl-3-pentyl-benzo[c]chromene |
| CBN-OTMS | | trimethyl((6,6,9-trimethyl-3-pentyl-6H-benzo[c]chromen-1-yl)oxy)silane |
| Cannabinodiol (CBND) | | 2,6-dihydroxy-4-pentyl-2'-isopropenyl-5'-methyl-1,1'-biphenyl |
| Cannabicitran (CBT) | | 1,5,5-trimethyl-9-pentyl-6,15-dioxatetracyclo[9.3.1.0$^{4,13}$.0$^{7,12}$]-pentadeca-7(12),8,10-triene |
| Dehydrocannabifuran (DHCBF) | | 5-isopropenyl-8-methyl-2-pentyl-9-oxa-4-fluorenol |

TABLE 1-continued

| Cannabinoids | | |
|---|---|---|
| Trivial Name | Structure | IUPAC name |
| Dihydrocannabinodiol (H₂CBND) | | 2,6-dihydroxy-4-pentyl-2'-isopropyl-5'-methyl-1,1'-biphenyl |
| Dihydrocannabidiol (H₂CBD) | | 2-[(1R,6R)-6-Isopropyl-3-methylcyclohex-2-en-1-yl]-5-pentylbenzene-1,3-diol |
| Tetrahydrocannabidiol (H₄CBD) | | 2-[(1S,6R)-6-Isopropyl-3-methylcyclohexyl]-5-pentylbenzene-1,3-diol |
| Δ$^{8(9)}$-iso-tetrahydrocannabinol (Δ$^{8(9)}$-iso-THC) | | 3,4,5,6-tetrahydro-2-methyl-5-(1-methylethenyl)-9-pentyl-2,6-methano-2H-1-benzoxocin-7-ol |
| Δ$^{4(8)}$-iso-tetrahydrocannabinol (Δ$^{4(8)}$-iso-THC) | | 3,4,5,6-tetrahydro-2-methyl-5-(1-methylethylidene)-9-pentyl-2,6-methano-2H-1-benzoxocin-7-ol |
| Δ$^{4(5)}$-iso-tetrahydrocannabinol (Δ$^{4(5)}$-iso-THC) | | 3,6-dihydro-2-methyl-5-(1-methylethyl)-9-pentyl-2,6-methano-2H-1-benzoxocin-7-ol |

TABLE 1-continued

| | Cannabinoids | |
|---|---|---|
| Trivial Name | Structure | IUPAC name |
| Hexahydrocannabinol (HHC) | | 6,6,9-trimethyl-3-pentyl-6a,7,8,9,10,10a-hexahydro-6H-benzo[c]chromen-1-ol |
| $\Delta^{8(9)}$-tetrahydrocannabinol ($\Delta^{8(9)}$-THC) | | 6,6,9-trimethyl-3-pentyl-6a,7,10,10a-tetrahydro-6H-benzo[c]chromen-1-ol |
| 11-hydroxy-$\Delta^{8(9)}$-tetrahydrocannabinol (11-OH-$\Delta^{8(9)}$-THC) | | 9-(hydroxymethyl)-6,6-dimethyl-3-pentyl-6a,7,10,10a-tetrahydro-6H-benzo[c]chromen-1-ol |
| $\Delta^{8(9)}$-tetrahydrocannabinolic acid ($\Delta^{8(9)}$-THCA) | | 6,6,9-trimethyl-3-pentyl-6a,7,10,10a-tetrahydro-6H-benzo[c]chromen-1-yl acetate |
| Methoxy $\Delta^{8(9)}$-tetrahydrocannabinol ($\Delta^{8(9)}$-THC-OMe) | | 1-methoxy-6,6,9-trimethyl-3-pentyl-6a,7,10,10a-tetrahydro-6H-benzo[c]chromene |
| $\Delta^{8(9)}$-tetrahydrocannabivarol ($\Delta^{8(9)}$-THCV) | | 6,6,9-trimethyl-3-propyl-6a,7,10,10a-tetrahydro-6H-benzo[c]chromen-1-ol |

TABLE 1-continued

| Cannabinoids | | |
|---|---|---|
| Trivial Name | Structure | IUPAC name |
| Δ$^{9(10)}$-tetrahydrocannabinol (Δ$^{9(10)}$-THC) | | 6,6,9-trimethyl-3-pentyl-6a,7,8,10a-tetrahydro-6H-benzo[c]chromen-1-ol |
| 11-hydroxy-Δ$^{9(10)}$-tetrahydrocannabinol (11-OH-Δ$^{9(10)}$-THC) | | 9-(hydroxymethyl)-6,6-dimethyl-3-pentyl-6a,7,8,10a-tetrahydro-6H-benzo[c]chromen-1-ol |
| Δ$^{9(10)}$-tetrahydrocannabinolic acid (Δ$^{9(10)}$-THCA) | | (6aR,10aR)-1-Hydroxy-6,6,9-trimethyl-3-pentyl-6a,7,8,10a-tetrahydro-6H-benzo[c]chromene-2-carboxylic acid |
| Δ$^{9(10)}$-tetrahydrocannabinovarol (Δ$^{9(10)}$-THCV) | | 6,6,9-Trimethyl-3-propyl-6a,7,8,10a-tetrahydro-6H-benzo[c]chromen-1-ol |
| Δ$^{10(10a)}$-tetrahydrocannabinol (Δ$^{10(10a)}$-THC) | | 6,6,9-trimethyl-3-pentyl-6a,7,8,9-tetrahydro-6H-benzo[c]chromen-1-ol |
| Δ$^{6a(10a)}$-tetrahydrocannabinol (Δ$^{6a(10a)}$-THC) | | 6,6,9-trimethyl-3-pentyl-7,8,9,10-tetrahydro-6H-benzo[c]chromen-1-ol |

TABLE 1-continued

Cannabinoids

| Trivial Name | Structure | IUPAC name |
|---|---|---|
| Δ^{6a(10a)}-THC-OTMS | | trimethyl((6,6,9-trimethyl-3-pentyl-7,8,9,10-tetrahydro-6H-benzo[c]chromen-1-yl)oxy)silane |
| iso-hexahydrocannabinol (iso-HHC) | 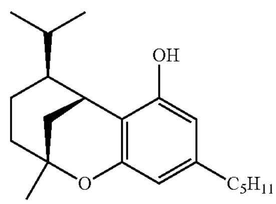 | (2α,5α,6α)-(-)-3,4,5,6-tetrahydro-2-methyl-5-(1-methylethyl)-9-pentyl-2,6-methano-2H-1-benzoxocin-7-ol |
| 4-desisopropenyl-cannabinodiol (4-DI-CBND) | 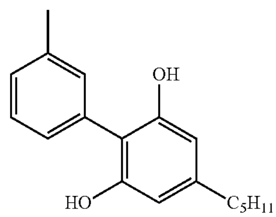 | 3'-methyl-4-pentyl-[1,1'-biphenyl]-2,6-diol |
| Abnormal Cannabidiol (Abn-CBD) | 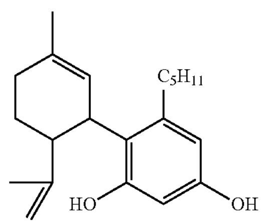 | 4-[(1R,6R)-3-methyl-6-(1-methylethenyl)-2-cyclohexen-1-yl]-5-pentyl-1,3-benzenediol |
| Abnormal Cannabivarol (Abn-CBNV) | 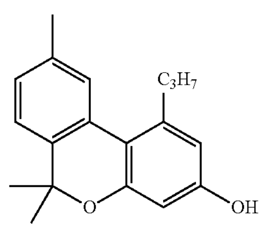 | 6,6,9-trimethyl-1-propyl-6H-benzo[c]chromen-3-ol |
| Diacetylcannabidiol (CBD-(OAc)$_2$), | 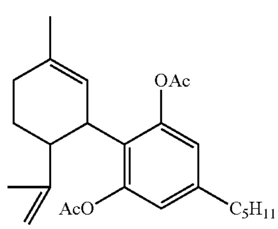 | 5'-methyl-4-pentyl-2'-(prop-1-en-2-yl)-1',2',3',4'-tetrahydro-[1,1'-biphenyl]-2,6-diyl diacetate |
| Cannabiorcinol (CBN-C$_1$), | 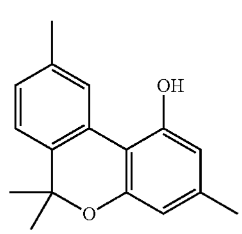 | 3-methyl-6,6,9-trimethyl-6H-benzo[c]chromen-1-ol |

TABLE 1-continued

| Cannabinoids | | |
|---|---|---|
| Trivial Name | Structure | IUPAC name |
| Cannabinol ethyl (CBN-C$_2$), | | 3-ethyl-6,6,9-trimethyl-6H-benzo[c]chromen-1-ol |
| Cannabibutol (CBN-C$_4$), | | 3-butyl-6,6,9-trimethyl-6H-benzo[c]chromen-1-ol |
| Cannabihexol (CBN-C$_6$) | | 3-hexyl-6,6,9-trimethyl-6H-benzo[c]chromen-1-ol |
| Cannabiphorol (CBN-C$_7$) | | 3-heptyl-6,6,9-trimethyl-6H-benzo[c]chromen-1-ol |
| Acetylcannabivarol (CBNV-OAc) | | 6,6,9-trimethyl-3-propyl-6H-benzo[c]chromen-1-yl acetate |
| $\Delta^{8(9)}$-iso-tetrahydrocannabifuran ($\Delta^{8(9)}$-iso-THCBF) | | (5aR,9aR)-9a-isopropyl-8-methyl-3-pentyl-5a,6,7,9a-tetrahydrodibenzo[b,d]furan-1-ol |

TABLE 1-continued

Cannabinoids

| Trivial Name | Structure | IUPAC name |
| --- | --- | --- |
| Dihydrocannabielsoin (H₂CBE) | 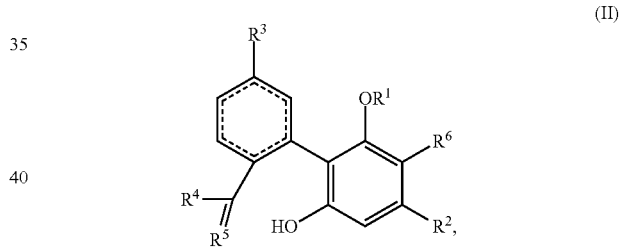 | (5aS,6S,9S,9aR)-9-isopropyl-6-methyl-3-pentyl-5a,6,7,8,9,9a-hexahydrodibenzo[b,d]furan-1,6-diol |
| Tetrahydrocannabigerol (H₄CBG) | 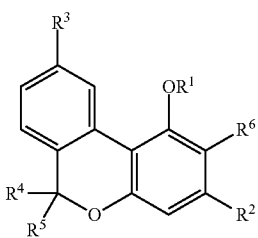 | 2-(3,7-dimethyloctyl)-5-pentylbenzene-1,3-diol |
| Olivetol | 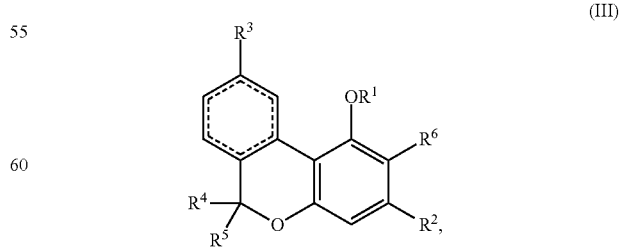 | 5-pentyl-1,3-benzenediol |

Methods

Provided in the present disclosure is a method of preparing a compound of Formula (I):

(I)

[structure of Formula (I)]

or a pharmaceutically acceptable salt thereof, wherein:

$R^1$ is hydrogen, $C_1$-$C_{10}$ alkyl, C(=O)—($C_1$-$C_{10}$ alkyl), or Si($C_1$-$C_{10}$ alkyl)$_3$;

$R^2$ is hydrogen or $C_1$-$C_{10}$ alkyl;

$R^3$ is hydrogen, $C_1$-$C_6$ alkyl, or $C_1$-$C_6$ hydroxyalkyl;

$R^4$ is hydrogen, $C_1$-$C_{10}$ alkyl, or $C_2$-$C_{10}$ alkenyl;

$R^5$ is hydrogen, $C_1$-$C_{10}$ alkyl, or $C_2$-$C_{10}$ alkenyl; and $R^6$ is hydrogen, $C_1$-$C_6$ alkyl, C(=O)(OH), or C(=O)—($C_1$-$C_6$ alkyl);

the method including:

admixing a catalyst, an oxidizing agent, and a compound of Formula (II):

(II)

[structure of Formula (II)]

wherein each ═══ is independently a single bond or a double bond, and wherein only one ═══ is a double bond, to form a compound of Formula (I), or a pharmaceutically acceptable salt thereof, wherein the catalyst is $I_2$, $Br_2$, or $Cl_2$.

In some embodiments, the admixing includes:

(a) reacting the catalyst and the compound of Formula (II) to form a compound of Formula (III):

(III)

[structure of Formula (III)]

wherein each ═══ is independently a single bond or a double bond, and wherein only one ═══ is a double bond; and (b) reacting the compound of Formula (III), the catalyst, and the oxidizing agent to form the compound of Formula (I), or a pharmaceutically acceptable salt thereof.

An exemplary synthetic scheme of the methods disclosed herein is shown in Scheme 2, where $R^1$-$R^6$ are as described elsewhere herein and $X_2$ is $I_2$, $Br_2$, or $Cl_2$.

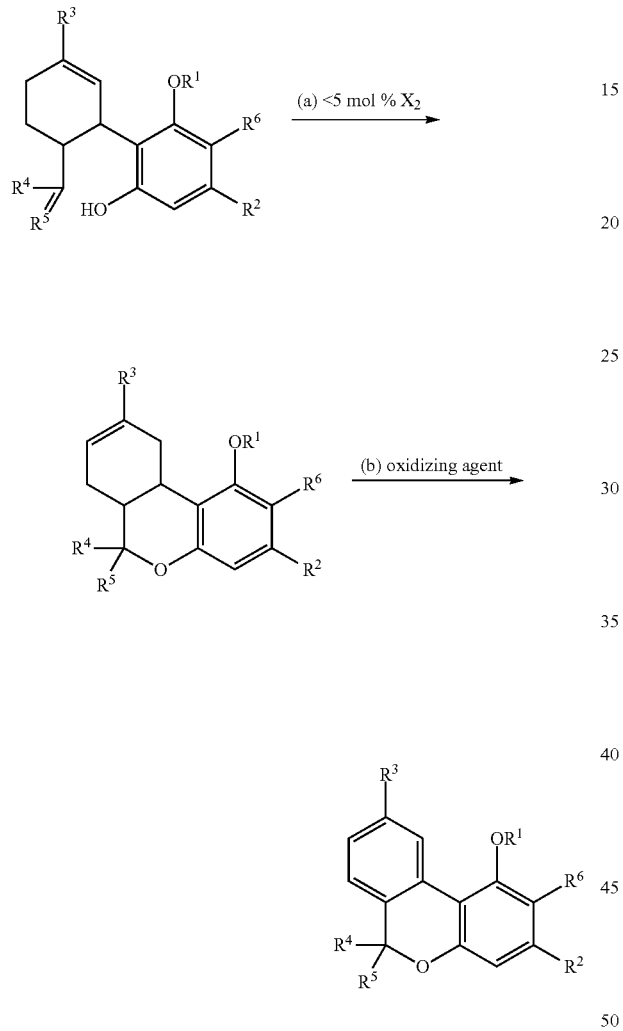

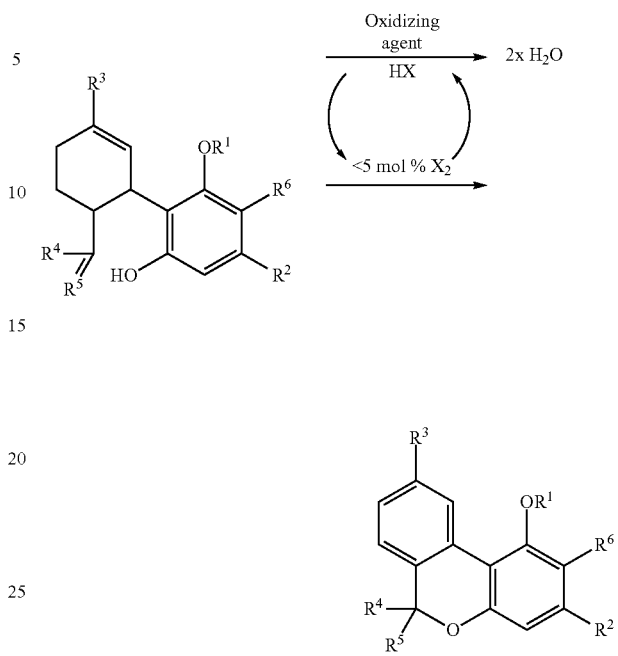

In some embodiments, step (a) and step (b) are performed in situ. In some embodiments, the compound formed after step (a) is not isolated prior to performing step (b).

In some embodiments, $X_2$ is $I_2$. In some embodiments, $X_2$ is $Br_2$. In some embodiments, $X_2$ is $Cl_2$.

In some embodiments, the oxidizing agent includes one or more of $O_2$, $S_8$, dimethyl sulfoxide, benzoquinone, chloranil, hydrogen peroxide, peracetic acid, diacetyl peroxide, ditertbutyl peroxide, dicumyl peroxide, peroxybenzoic acid, and benzoyl peroxide. In some embodiments, the oxidizing agent includes $S_8$. In some embodiments, the oxidizing agent includes $O_2$ and an inert gas.

An exemplary synthetic scheme of the methods disclosed herein is shown in Scheme 3, where $R^1$-$R^6$ are as described elsewhere herein.

In some embodiments, $X_2$ is $I_2$ and HX is HI. In some embodiments, $X_2$ is $Br_2$ and HX is HBr. In some embodiments, $X_2$ is $Cl_2$ and HX is HCl.

In some embodiments, the oxidizing agent includes one or more of $O_2$, $S_8$, dimethyl sulfoxide, benzoquinone, chloranil, hydrogen peroxide, peracetic acid, diacetyl peroxide, ditertbutyl peroxide, dicumyl peroxide, peroxybenzoic acid, and benzoyl peroxide. In some embodiments, the oxidizing agent includes $S_8$. In some embodiments, the oxidizing agent includes $O_2$ and an inert gas.

Also provided are methods of preparing a compound of Formula (I):

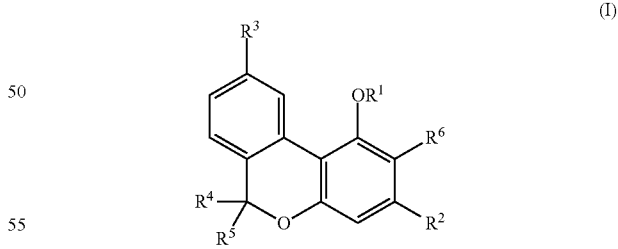

(I)

or a pharmaceutically acceptable salt thereof, wherein:

$R^1$ is hydrogen, $C_1$-$C_{10}$ alkyl, C(=O)—($C_1$-$C_{10}$ alkyl);

$R^2$ is hydrogen or $C_1$-$C_{10}$ alkyl;

$R^3$ is hydrogen, $C_1$-$C_6$ alkyl, or $C_1$-$C_6$ hydroxyalkyl;

$R^4$ is hydrogen, $C_1$-$C_{10}$ alkyl, or $C_2$-$C_{10}$ alkenyl;

$R^5$ is hydrogen, $C_1$-$C_{10}$ alkyl, or $C_2$-$C_{10}$ alkenyl; and $R^6$ is hydrogen, $C_1$-$C_6$ alkyl, C(=O)(OH), or C(=O)—($C_1$-$C_6$ alkyl);

the method including:
admixing a catalyst, an oxidizing agent, and a compound of Formula (III):

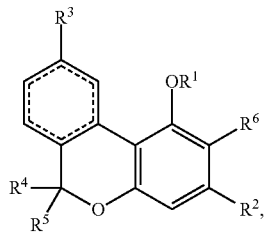

to form the compound of Formula (I), or a pharmaceutically acceptable salt thereof,
  wherein each ⚌ is independently a single bond or a double bond, and wherein only one ⚌ is a double bond, and
  wherein the catalyst is $I_2$, $Br_2$, or $Cl_2$.

An exemplary synthetic scheme of the method disclosed herein is shown in Scheme 4, where $R^1$-$R^6$ are as described elsewhere herein.

Scheme 4

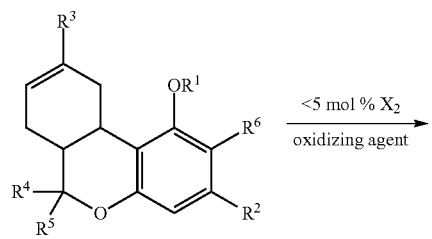

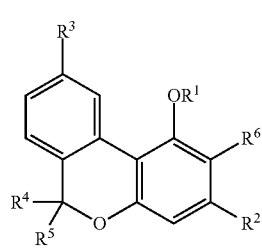

In some embodiments, $X_2$ is $I_2$. In some embodiments, $X_2$ is $Br_2$. In some embodiments, $X_2$ is $Cl_2$.

In some embodiments, the oxidizing agent includes one or more of $O_2$, $S_8$, dimethyl sulfoxide, benzoquinone, chloranil, hydrogen peroxide, peracetic acid, diacetyl peroxide, ditertbutyl peroxide, dicumyl peroxide, peroxybenzoic acid, and benzoyl peroxide. In some embodiments, the oxidizing agent includes $S_8$. In some embodiments, the oxidizing agent includes $O_2$ and an inert gas.

In some embodiments, the compound of Formula (III) is prepared by a process including:
admixing the catalyst and a compound of Formula (II):

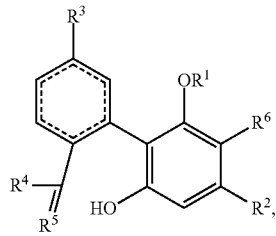

to form the compound of Formula (III),
  wherein each ⚌ is independently a single bond or a double bond, and wherein only one ⚌ is a double bond.

An exemplary synthetic scheme of the method disclosed herein is shown in Scheme 5, where $R^1$-$R^6$ are as described elsewhere herein and $X_2$ is $I_2$, $Br_2$, or $Cl_2$.

Scheme 5

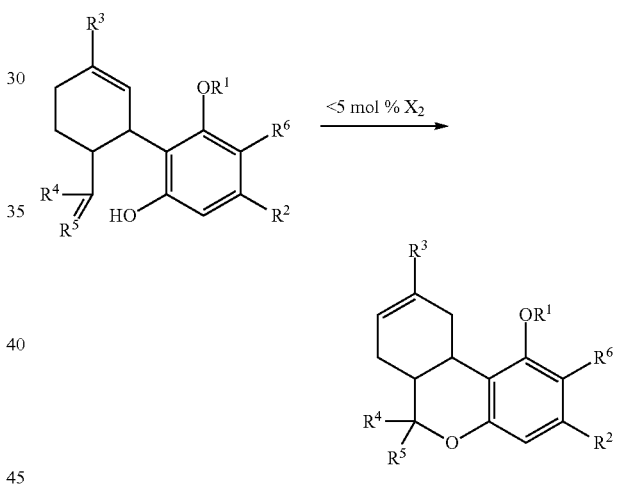

In some embodiments, $X_2$ is $I_2$. In some embodiments, $X_2$ is $Br_2$. In some embodiments, $X_2$ is $Cl_2$.

In some embodiments, the oxidizing agent includes one or more of $O_2$, $S_8$, dimethyl sulfoxide, benzoquinone, chloranil, hydrogen peroxide, peracetic acid, diacetyl peroxide, ditertbutyl peroxide, dicumyl peroxide, peroxybenzoic acid, and benzoyl peroxide. In some embodiments, the oxidizing agent includes $S_8$. In some embodiments, the oxidizing agent includes $O_2$ and an inert gas.

In some embodiments, the method of preparing a compound of Formula (III) from a compound of Formula (II) is performed in situ. In some embodiments, the method of preparing a compound of Formula (I), or a pharmaceutically acceptable salt thereof, from the compound of Formula (II) or the compound of Formula (III) is performed in situ.

In some embodiments of the methods of the present disclosure, $R^1$ is hydrogen or $C_1$-$C_{10}$ alkyl.

In some embodiments, $R^1$ is hydrogen.

In some embodiments, $R^1$ is $C_1$-$C_{10}$ alkyl. In some embodiments, $R^1$ is $C_1$-$C_6$ alkyl. In some embodiments, $R^1$ is $C_1$-$C_3$ alkyl. In some embodiments, $R^1$ is methyl, ethyl, or propyl. In some embodiments, $R^1$ is methyl. In some embodiments, $R^1$ is ethyl. In some embodiments, $R^1$ is propyl.

In some embodiments, $R^1$ is C(=O)—($C_1$-$C_{10}$ alkyl). In some embodiments, $R^1$ is C(=O)—($C_1$-$C_6$ alkyl). In some embodiments, $R^1$ is C(=O)—($C_1$-$C_3$ alkyl). In some embodiments, $R^1$ is C(=O)—($C_3$ alkyl). In some embodiments, $R^1$ is C(=O)—($C_2$ alkyl). In some embodiments, $R^1$ is C(=O)—($C_1$ alkyl).

In some embodiments, $R^1$ is Si($C_1$-$C_{10}$ alkyl)$_3$. In some embodiments, $R^1$ is Si($C_1$-$C_6$ alkyl)$_3$. In some embodiments, $R^1$ is Si($C_1$-$C_3$ alkyl)$_3$. In some embodiments, $R^1$ is Si($CH_3$)$_3$.

In some embodiments, $R^2$ is hydrogen.

In some embodiments, $R^2$ is $C_1$-$C_{10}$ alkyl. In some embodiments, $R^2$ is $C_1$-$C_6$ alkyl. In some embodiments, $R^2$ is $C_3$-$C_6$ alkyl. In some embodiments, $R^2$ is $C_1$-$C_3$ alkyl. In some embodiments, $R^2$ is $C_6$ alkyl. In some embodiments, $R^2$ is $C_5$ alkyl. In some embodiments, $R^2$ is $C_4$ alkyl. In some embodiments, $R^2$ is $C_3$ alkyl. In some embodiments, $R^2$ is $C_2$ alkyl. In some embodiments, $R^2$ is $C_1$ alkyl.

In some embodiments, $R^3$ is hydrogen.

In some embodiments, $R^3$ is $C_1$-$C_6$ alkyl. In some embodiments, $R^3$ is $C_1$-$C_3$ alkyl. In some embodiments, $R^3$ is methyl, ethyl, or propyl. In some embodiments, $R^3$ is methyl. In some embodiments, $R^3$ is ethyl. In some embodiments, $R^3$ is propyl.

In some embodiments, $R^3$ is $C_1$-$C_6$ hydroxyalkyl. In some embodiments, $R^3$ is $C_1$-$C_3$ hydroxyalkyl. In some embodiments, $R^3$ is $CH_2CH_2OH$, $CH(CH_3)(OH)$, or $CH_2OH$. In some embodiments, $R^3$ is $CH_2CH_2OH$. In some embodiments, $R^3$ is $CH(CH_3)(OH)$. In some embodiments, $R^3$ is $CH_2OH$.

In some embodiments, $R^4$ is hydrogen.

In some embodiments, $R^4$ is $C_1$-$C_{10}$ alkyl. In some embodiments, $R^4$ is $C_1$-$C_6$ alkyl. In some embodiments, $R^4$ is $C_5$-$C_{10}$ alkyl. In some embodiments, $R^4$ is $C_3$-$C_6$ alkyl. In some embodiments, $R^4$ is $C_1$-$C_3$ alkyl. In some embodiments, $R^4$ is methyl, ethyl, or propyl. In some embodiments, $R^4$ is methyl. In some embodiments, $R^4$ is ethyl. In some embodiments, $R^4$ is propyl.

In some embodiments, $R^4$ is $C_2$-$C_{10}$ alkenyl. In some embodiments, $R^4$ is $C_4$-$C_{10}$ alkenyl. In some embodiments, $R^4$ is $C_6$-$C_{10}$ alkenyl. In some embodiments, $R^4$ is $C_8$-$C_{10}$ alkenyl. In some embodiments, $R^4$ is $C_2$-$C_8$ alkenyl. In some embodiments, $R^4$ is $C_4$-$C_8$ alkenyl. In some embodiments, $R^4$ is $C_6$-$C_8$ alkenyl. In some embodiments, $R^4$ is $C_2$-$C_6$ alkenyl. In some embodiments, $R^4$ is $C_4$-$C_6$ alkenyl. In some embodiments, $R^4$ is $C_2$ alkenyl. In some embodiments, $R^4$ is $C_3$ alkenyl. In some embodiments, $R^4$ is $C_4$ alkenyl. In some embodiments, $R^4$ is $C_5$ alkenyl. In some embodiments, $R^4$ is $C_6$ alkenyl.

In some embodiments, $R^5$ is hydrogen.

In some embodiments, $R^5$ is $C_1$-$C_{10}$ alkyl. In some embodiments, $R^5$ is $C_1$-$C_6$ alkyl. In some embodiments, $R^5$ is $C_1$-$C_3$ alkyl. In some embodiments, $R^5$ is $C_5$-$C_{10}$ alkyl. In some embodiments, $R^5$ is methyl, ethyl, or propyl. In some embodiments, $R^5$ is methyl. In some embodiments, $R^5$ is ethyl. In some embodiments, $R^5$ is propyl.

In some embodiments, $R^5$ is $C_2$-$C_{10}$ alkenyl. In some embodiments, $R^5$ is $C_4$-$C_{10}$ alkenyl. In some embodiments, $R^5$ is $C_6$-$C_{10}$ alkenyl. In some embodiments, $R^5$ is $C_8$-$C_{10}$ alkenyl. In some embodiments, $R^5$ is $C_2$-$C_8$ alkenyl. In some embodiments, $R^5$ is $C_4$-$C_8$ alkenyl. In some embodiments, $R^5$ is $C_6$-$C_8$ alkenyl. In some embodiments, $R^5$ is $C_2$-$C_6$ alkenyl. In some embodiments, $R^5$ is $C_4$-$C_6$ alkenyl. In some embodiments, $R^5$ is $C_2$ alkenyl. In some embodiments, $R^5$ is $C_3$ alkenyl. In some embodiments, $R^5$ is $C_4$ alkenyl. In some embodiments, $R^5$ is $C_5$ alkenyl. In some embodiments, $R^5$ is $C_6$ alkenyl.

In some embodiments, $R^6$ is hydrogen.

In some embodiments, $R^6$ is $C_1$-$C_3$ alkyl. In some embodiments, $R^6$ is methyl. In some embodiments, $R^6$ is ethyl. In some embodiments, $R^6$ is propyl.

In some embodiments, $R^6$ is C(=O)(OH).

In some embodiments, $R^6$ is C(=O)—($C_1$-$C_6$ alkyl). In some embodiments, $R^6$ is C(=O)—($C_1$-$C_3$ alkyl). In some embodiments, $R^6$ is C(=O)—($CH_3$).

In some embodiments, one or more of the compound of Formula (I), the compound of Formula (II), and the compound of Formula (III) are selected from the group consisting of compounds in Examples 1-3, or a pharmaceutically acceptable salt thereof. In some embodiments, the compound of Formula (I) is CBN, or a pharmaceutically acceptable salt thereof. In some embodiments, the compound of Formula (II) is CBD, or a pharmaceutically acceptable salt thereof. In some embodiments, the compound of Formula (III) is THC. In some embodiments, the compound of Formula (III) is $\Delta^{8(9)}$-THC. In some embodiments, the compound of Formula (III) includes a mixture of $\Delta^{8(9)}$-THC and $\Delta^{9(10)}$-THC.

In some embodiments, the compound of Formula (I) is selected from the group of compounds delineated in Table 2, or a pharmaceutically acceptable salt thereof.

TABLE 2

| Trivial Name | Structure | IUPAC name |
|---|---|---|
| Cannabinol (CBN) | 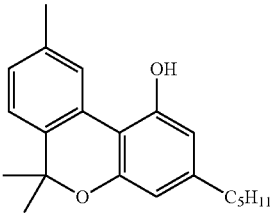 | 6,6,9-Trimethyl-3-pentyl-benzo[c]chromen-1-ol |

TABLE 2-continued

| Trivial Name | Structure | IUPAC name |
| --- | --- | --- |
| 11-Hydroxycannabinol (11-OH-CBN) | 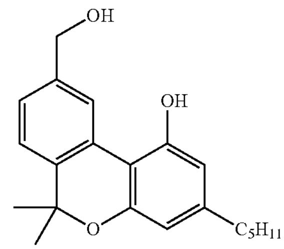 | 9-(hydroxymethyl)-6,6-dimethyl-3-pentyl-6H-benzo[c]chromen-1-ol |
| Cannabinolic acid (CBNA) | 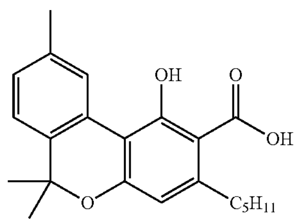 | 1-hydroxy-6,6,9-trimethyl-3-pentyl-benzo[c]chromene-2-carboxylic acid |
| Cannabivarol (CBNV) | 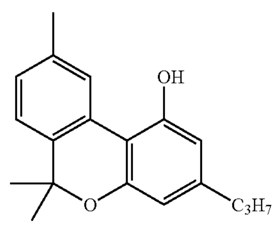 | 6,6,9-trimethyl-3-pentyl-benzo[c]chromen-1-ol |
| Acetylcannabinol (CBN-OAc) | 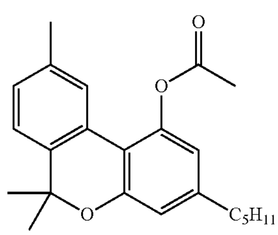 | 1-acetoxy-6,6,9-trimethyl-3-pentyl-benzo[c]chromene |
| Methoxycannabinol (CBN-OMe) | 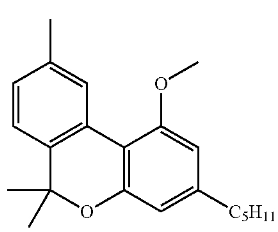 | 1-methoxy-6,6,9-trimethyl-3-pentyl-benzo[c]chromene |
| CBN-OTMS | 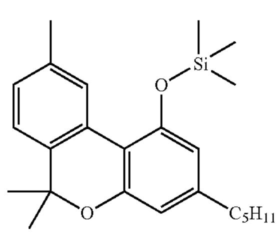 | trimethyl((6,6,9-trimethyl-3-pentyl-6H-benzo[c]chromen-1-yl)oxy)silane |

In some embodiments, the compound of Formula (II) is selected from the group of compounds delineated in Table 3, or a pharmaceutically acceptable salt thereof

TABLE 3

| Trivial Name | Structure | IUPAC name |
|---|---|---|
| Cannabidiol (CBD) | 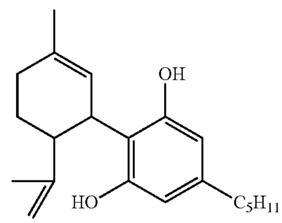 | 2-[(1R,6R)-6-Isopropenyl-3-methylcyclohex-2-en-1-yl]-5-pentylbenzene-1,3-diol |
| 11-Hydroxycannabidiol (11-OH-CBD) | 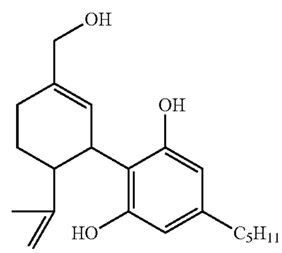 | 5'-(hydroxymethyl)-4-pentyl-2'-(prop-1-en-2-yl)-1',2',3',4'-tetrahydro-[1,1'-biphenyl]-2,6-diol |
| Cannabidivarol (CBDV) | 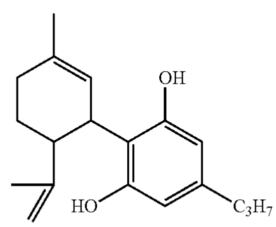 | 2-[(1R,6R)-6-Isopropenyl-3-methylcyclohex-2-en-1-yl]-5-propylbenzene-1,3-diol |
| Cannabidiolic acid (CBDA) | 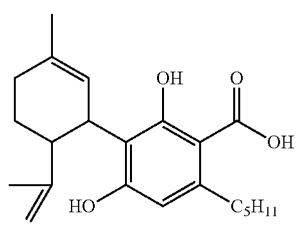 | (1'R,2'R)-2,6-Dihydroxy-5'-methyl-4-pentyl-2'-(prop-1-en-2-yl)-1',2',3',4'-tetrahydro[1,1'-biphenyl]-3-carboxylic acid |

In some embodiments, the compound of Formula (III) is selected from the group of compounds delineated in Table 4, or a pharmaceutically acceptable salt thereof.

TABLE 4

| Trivial Name | Structure | IUPAC name |
|---|---|---|
| $\Delta^{8(9)}$-tetrahydrocannabinol ($\Delta^{8(9)}$-THC) | 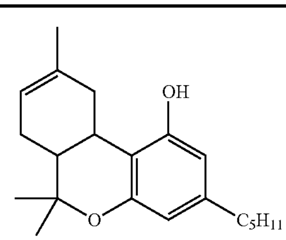 | 6,6,9-trimethyl-3-pentyl-6a,7,10,10a-tetrahydro-6H-benzo[c]chromen-1-ol |

TABLE 4-continued

| Trivial Name | Structure | IUPAC name |
|---|---|---|
| 11-hydroxy-Δ[8(9)]-tetrahydrocannabinol (11-OH-Δ[8(9)]-THC) | | 9-(hydroxymethyl)-6,6-dimethyl-3-pentyl-6a,7,10,10a-tetrahydro-6H-benzo[c]chromen-1-ol |
| Δ[8(9)]-tetrahydrocannabinolic acid (Δ[8(9)]-THCA) | | 6,6,9-trimethyl-3-pentyl-6a,7,10,10a-tetrahydro-6H-benzo[c]chromen-1-yl acetate |
| Methoxy Δ[8(9)]-tetrahydrocannabinol (Δ[8(9)]-THC-OMe) | | 1-methoxy-6,6,9-trimethyl-3-pentyl-6a,7,10,10a-tetrahydro-6H-benzo[c]chromene |
| Δ[8(9)]-tetrahydrocannabivarol (Δ[8(9)]-THCV) | | 6,6,9-trimethyl-3-propyl-6a,7,10,10a-tetrahydro-6H-benzo[c]chromen-1-ol |
| Δ[9(10)]-tetrahydrocannabinol (Δ[9(10)]-THC) | | 6,6,9-trimethyl-3-pentyl-6a,7,8,10a-tetrahydro-6H-benzo[c]chromen-1-ol |
| 11-hydroxy-Δ[9(10)]-tetrahydrocannabinol (11-OH-Δ[9(10)]-THC) | | 9-(hydroxymethyl)-6,6-dimethyl-3-pentyl-6a,7,8,10a-tetrahydro-6H-benzo[c]chromen-1-ol |

TABLE 4-continued

| Trivial Name | Structure | IUPAC name |
|---|---|---|
| $\Delta^{9(10)}$-tetrahydrocannabinolic acid ($\Delta^{9(10)}$-THCA) | | (6aR,10aR)-1-Hydroxy-6,6,9-trimethyl-3-pentyl-6a,7,8,10a-tetrahydro-6H-benzo[c]chromene-2-carboxylic acid |
| $\Delta^{9(10)}$-tetrahydrocannabinovarol ($\Delta^{9(10)}$-THCV) | | 6,6,9-Trimethyl-3-propyl-6a,7,8,10a-tetrahydro-6H-benzo[c]chromen-1-ol |
| $\Delta^{10(10a)}$-tetrahydrocannabinol ($\Delta^{10(10a)}$-THC) | | 6,6,9-trimethyl-3-pentyl-6a,7,8,9-tetrahydro-6H-benzo[c]chromen-1-ol |
| $\Delta^{6a(10a)}$-tetrahydrocannabinol $\Delta^{6a(10a)}$-THC) | | 6,6,9-trimethyl-3-pentyl-7,8,9,10-tetrahydro-6H-benzo[c]chromen-1-ol |
| $\Delta^{6a(10a)}$-THC-OTMS | | trimethyl((6,6,9-trimethyl-3-pentyl-7,8,9,10-tetrahydro-6H-benzo[c]chromen-1-yl)oxy)silane |

In some embodiments of the methods of the present disclosure, the catalyst is selected from $I_2$, $Br_2$, and $Cl_2$. In some embodiments, the catalyst is $I_2$. In some embodiments, the catalyst is $Br_2$. In some embodiments, the catalyst is $I_2$ or $Br_2$. In some embodiments, the catalyst is $Cl_2$.

In some embodiments, the oxidizing agent includes one or more of a peroxide, a quinone, $O_2$, $S_8$, and dimethyl sulfoxide. In some embodiments, the oxidizing agent includes one or more of $O_2$, $S_8$, benzoquinone, chloranil, benzoyl peroxide, peracetic acid, hydrogen peroxide, and dimethyl sulfoxide. In some embodiments, the oxidizing agent includes one or more of a peroxide or a quinone. In some embodiments, the oxidizing agent is a peroxide. The peroxide can include one or more of hydrogen peroxide, peracetic acid, diacetyl peroxide, ditertbutyl peroxide, dicumyl peroxide, peroxybenzoic acid, and benzoyl peroxide. In some embodiments, the peroxide is hydrogen peroxide or peracetic acid. In some embodiments, the peroxide is hydrogen peroxide. In some embodiments, the peroxide is peracetic acid. In some embodiments, the oxidizing agent is a quinone. The quinone can include one or more of chloranil, benzoquinone, and 2,3-dichloro-5,6-dicyano-1,4-benzoquinone (DDQ). In some embodiments, the quinone is benzoquinone. In some embodiments, the quinone is DDQ. In some embodiments, the quinone is chloranil.

In some embodiments, the oxidizing agent includes one or more of $O_2$, $S_8$, and dimethyl sulfoxide. In some embodiments, the oxidizing agent is $S_8$. In some embodiments, the oxidizing agent is dimethyl sulfoxide. In some embodiments, the oxidizing agent is $O_2$. As used herein, the $O_2$ can be pure $O_2$ or can be in a mixture with additional gases, for example, an inert gas. In some embodiments, the oxidizing agent includes $O_2$ and an inert gas. In some embodiments, the inert gas is $N_2$. In some embodiments, the oxidizing agent includes $O_2$ and $N_2$.

In some embodiments, the oxidizing agent is present in an inert gas in amount of about 1 wt % to about 25 wt %, such as about 1 wt % to about 20 wt %, about 1 wt % to about 15 wt %, about 1 wt % to about 12 wt %, about 1 wt % to about 10 wt %, about 1 wt % to about 8 wt %, about 1 wt % to about 5 wt %, about 5 wt % to about 25 wt %, about 5 wt % to about 20 wt %, about 5 wt % to about 15 wt %, about 5 wt % to about 12 wt %, about 5 wt % to about 10 wt %, about 5 wt % to about 8 wt %, about 8 wt % to about 25 wt %, about 8 wt % to about 20 wt %, about 8 wt % to about 15 wt %, about 8 wt % to about 12 wt %, about 8 wt % to about 10 wt %, about 10 wt % to about 25 wt %, about 10 wt % to about 20 wt %, about 10 wt % to about 15 wt %, about 10 wt % to about 12 wt %, about 12 wt % to about 25 wt %, about 12 wt % to about 20 wt %, about 12 wt % to about 15 wt %, about 15 wt % to about 25 wt %, about 15 wt % to about 20 wt %, about 20 wt % to about 25 wt %, or less than about 25 wt %, less than about 20 wt %, less than about 15 wt %, less than about 12 wt %, less than about 10 wt %, less than about 10 wt %, less than about 8 wt %, less than about 5 wt %, or about 25 wt %, about 24 wt %, about 23 wt %, about 22 wt %, about 21 wt %, about 20 wt %, about 19 wt %, about 18 wt %, about 17 wt %, about 16 wt %, about 15 wt %, about 14 wt %, about 13 wt %, about 12 wt %, about 11 wt %, about 10 wt %, about 9 wt %, about 8 wt %, about 7 wt %, about 6 wt %, about 5 wt %, about 4 wt %, about 3 wt %, about 2 wt %, or about 1 wt %, based on the total weight. In some embodiments, the oxidizing agent is $O_2$ and is present in the inert gas in an amount of about 25 wt %, about 20 wt %, about 15 wt %, about 10 wt %, about 9 wt %, about 8 wt %, about 7 wt %, about 6 wt %, about 5 wt %, about 4 wt %, about 3 wt %, about 2 wt %, or about 1 wt %. In some embodiments, the oxidizing agent includes about 10 wt % $O_2$ in about 90 wt % $N_2$.

In some embodiments, the methods of the disclosure can include a solvent such that reactants can be carried out in solution. In some embodiments, the admixing or the reacting is done in the presence of a solvent. Examples of solvents that can be used in the methods disclosed herein include, but are not limited to, organic solvents (e.g., polar aprotic, polar protic, or nonpolar aprotic solvents) that are inert under the conditions of the methods, such as aromatic hydrocarbons, halogenated hydrocarbons, ethers, aliphatic hydrocarbons, or mixtures thereof. In some embodiments, the solvent includes one or more of benzene, toluene, xylenes, mesitylene, anisole, acetonitrile, acetic acid, acetic anhydride, heptane, cyclohexane, pyridine, chloroform, isopropyl acetate, dimethyl sulfoxide, dimethylformamide, dimethylacetamide, N-methylpyrrolidone, and chlorobenzene. In some embodiments, the solvent includes one or more of benzene, toluene, anisole, acetonitrile, acetic acid, acetic anhydride, dimethyl sulfoxide, dimethylformamide, dimethylacetamide, and N-methylpyrrolidone. In some embodiments, the solvent is acetic acid.

The reacting or admixing of the compound of Formula (II) and the catalyst can be performed at a temperature of about 20° C. to about 220° C. For example, reacting or admixing of the compound of Formula (II) and the catalyst can be performed at a temperature of about 35° C. to about 200° C., about 50° C. to about 150° C., about 50° C. to about 100° C., about 40° C. to about 85° C., or less than about 100° C.

Reaction times can be determined upon completion or partial completion (e.g., about 90% or more completion) of the reaction. In embodiments, the reaction can be determined as being complete by spectroscopy (e.g., HPLC-UV). In some embodiments, the reaction times are about 30 seconds to about 72 hours, about 1 minute to about 24 hours, about 5 minutes to about 12 hours, about 30 minutes (min) to about 12 hours (h), about 1 hour to about 10 hours, about 1 hour to 3 hours, about 25 min to about 6 h, or about 30 min to about 3 h, for example, about 30 seconds, about 1 min, about 5 min, about 10 min, about 15 min, about 20 min, about 25 min, about 30 min, about 35 min, about 40 min, about 45 min, about 50 min, about 55 min, about 60 min, about 75 min, about 90 min, about 105 min, about 2 h, about 3 h, about 4 h, about 5 h, about 6 h, about 12 h, about 18 h, about 24 h, about 36 h, about 48 h, about 60 h, or about 72 h. The temperature and the reaction time will vary, depending on the particular catalyst and the compound of Formula (II).

The reacting or admixing of the compound of Formula (III), the catalyst, and the oxidizing agent can be performed at a temperature of about 20° C. to about 250° C. For example, reacting or admixing the compound of Formula (III), the catalyst, and the oxidizing agent can be performed at a temperature of about 50° C. to about 250° C., about 75° C. to about 200° C., about 50° C. to about 150° C., about 120° C. to about 170° C., or less than about 150° C.

Reaction times can be determined upon completion or partial completion (e.g., about 90% or more completion) of the reaction. In some embodiments, the reaction can be determined as being complete by spectroscopy (e.g., HPLC-UV). In some embodiments, the reaction times are about 30 seconds to about 72 hours, about 1 minute to about 24 hours, about 5 minutes to about 12 hours, about 30 minutes (min) to about 12 hours (h), about 1 hour to about 10 hours, about 1 hour to 3 hours, about 25 min to about 6 h, or about 30 min to about 3 h, for example, about 30 seconds, about 1 min, about 5 min, about 10 min, about 15 min, about 20 min, about 25 min, about 30 min, about 35 min, about 40 min, about 45 min, about 50 min, about 55 min, about 60 min, about 75 min, about 90 min, about 105 min, about 2 h, about 3 h, about 4 h, about 5 h, about 6 h, about 12 h, about 18 h, about 24 h, about 36 h, about 48 h, about 60 h, or about 72 h. The temperature and the reaction time will vary, depending on the particular catalyst, the oxidizing agent, and the compound of Formula (III).

In some embodiments of the methods of the present disclosure, the catalyst is present in an amount of about 0.1 mol % to about 10 mol %, such as about 0.1 mol % to about 9 mol %, about 0.1 mol % to about 8 mol %, about 0.1 mol % to about 7 mol %, about 0.1 mol % to about 6 mol %, about 0.1 mol % to about 5 mol %, about 0.1 mol % to about 4 mol %, about 0.1 mol % to about 3 mol %, about 0.1 mol % to about 2 mol %, about 0.1 mol % to about 1.5 mol %, about 0.1 mol % to about 1 mol %, about 0.1 mol % to about 0.5 mol %, about 0.5 mol % to about 10 mol %, about 0.5 mol % to about 9 mol %, about 0.5 mol % to about 8 mol %, about 0.5 mol % to about 7 mol %, about 0.5 mol % to about 6 mol %, about 0.5 mol % to about 5 mol %, about 0.5 mol % to about 4 mol %, about 0.5 mol % to about 3 mol %, about 0.5 mol % to about 2 mol %, about 0.5 mol % to about 1.5 mol %, about 0.5 mol % to about 1 mol %, about 1 mol % to about 10 mol %, about 1 mol % to about 9 mol %, about 1 mol % to about 8 mol %, about 1 mol % to about 7 mol %, about 1 mol % to about 6 mol %, about 1 mol % to about 5 mol %, about 1 mol % to about 4 mol %, about 1 mol % to about 3 mol %, about 1 mol % to about 2 mol %, about 1 mol % to about 1.5 mol %, about 1.5 mol % to about 10 mol %, about 1.5 mol % to about 9 mol %, about 1.5 mol % to about 8 mol %, about 1.5 mol % to about 7 mol %, about 1.5 mol % to about 6 mol %, about 1.5 mol % to about 5 mol %, about 1.5 mol % to about 4 mol %, about 1.5 mol % to about 3 mol %, about 1.5 mol % to about 2 mol %, about 2 mol % to about 10 mol %, about 2 mol % to about 9 mol %, about 2 mol % to about 8 mol %, about 2 mol % to about 7 mol %, about 2 mol % to about 6 mol %, about 2 mol % to about 5 mol %, about 2 mol % to about 4 mol %, about 2 mol % to about 3 mol %, about 3 mol % to about 10 mol %, about 3 mol % to about 9 mol %, about 3 mol % to about 8 mol %, about 3 mol % to about 7 mol %, about 3 mol % to about 6 mol %, about 3 mol % to about 5 mol %, about 3 mol % to about 4 mol %, about 4 mol % to about 10 mol %, about 4 mol % to about 9 mol %, about 4 mol % to about 8 mol %, about 4 mol % to about 7 mol %, about 4 mol % to about 6 mol %, about 4 mol % to about 5 mol %, about 5 mol % to about 10 mol %, about 5 mol % to about 9 mol %, about 5 mol % to about 8 mol %, about 5 mol % to about 7 mol %, about 5 mol % to about 6 mol %, about 6 mol % to about 10 mol %, about 6 mol % to about 9 mol %, about 6 mol % to about 8 mol %, about 6 mol % to about 7 mol %, about 7 mol % to about 10 mol %, about 7 mol % to about 9 mol %, about 7 mol % to about 8 mol %, about 8 mol % to about 10 mol %, about 8 mol % to about 9 mol %, about 9 mol % to about 10 mol %, or about 10 mol % or less, about 5 mol % or less, about 4 mol % or less, about 3 mol % or less, about 2 mol % or less, about 1 mol % or less, or about 0.5 mol % or less, based on the total mols of the compound of Formula (II) or the compound of Formula (III). In some embodiments, the catalyst is present in an amount of about 5 mol % or less, for example, about 4 mol %, about 3 mol %, about 2 mol %, about 1.5 mol %, about 1 mol %, about 0.9 mol %, about 0.8 mol %, about 0.7 mol %, about 0.6 mol %, about 0.5 mol %, about 0.4 mol %, about 0.3 mol %, about 0.2 mol %, or about 0.1 mol %, based on the total mols of the compound of Formula (II). In some embodiments, the catalyst is present in an amount of about 1 mol % based on the total mols of the compound of Formula (II). In some embodiments, the catalyst is present in an amount of about 0.6 mol % based on the total mols of the compound of Formula (II). In some embodiments, the catalyst is present in an amount of about 0.5 mol % based on the total mols of the compound of Formula (II). In some embodiments, the catalyst is present in an amount of about 5 mol % or less, for example, about 4 mol %, about 3 mol %, about 2 mol %, about 1.5 mol %, about 1 mol %, about 0.9 mol %, about 0.8 mol %, about 0.7 mol %, about 0.6 mol %, about 0.5 mol %, about 0.4 mol %, about 0.3 mol %, about 0.2 mol %, or about 0.1 mol %, based on the total mols of the compound of Formula (III). In some embodiments, the catalyst is present in an amount of about 1 mol % based on the total mols of the compound of Formula (III). In some embodiments, the catalyst is present in an amount of about 0.6 mol % based on the total mols of the compound of Formula (III). In some embodiments, the catalyst is present in an amount of about 0.5 mol % based on the total mols of the compound of Formula (III).

In some embodiments, the method disclosed herein are performed in a single vessel, also referred to as a "one pot reaction" or "one pot synthesis." The term "one pot reaction" also referred to as "one pot synthesis" refers to a multi-step chemical reaction carried out in a single vessel (e.g., single reaction vessel). In some embodiments, a reaction intermediate is generated in one step of the reaction, and the intermediate is then reacted in situ with other component(s) present in or introduced into the same vessel. The reaction intermediate generated is not isolated but serves directly as a reactant in a next step of the reaction. In some embodiments of the methods disclosed herein, a compound of Formula (III) is formed but is not isolated and is used directly in a next step where the oxidation of the cycloalkane ring occurs to form a phenyl ring.

The methods of the present disclosure can form a compound of Formula (I), or a pharmaceutically acceptable salt thereof. In some embodiments, the compound of Formula (I), or a pharmaceutically acceptable salt thereof, formed by the methods of the present disclosure has a purity of at least about 90%, such as at least about 95%, at least about 95.5%, at least about 96%, at least about 96.5%, at least about 97%, at least about 97.5%, at least about 98%, at least about 98.5%, at least about 99%, or at least 99.1%, 99.2%, 99.3%, 99.4%, 99.5%, 99.6%, 99.7%, 99.8%, or 99.9% and contains about 0.5 wt % THC or less, such as about 0.45 wt %, about 0.4 wt %, about 0.35 wt %, about 0.3 wt %, about 0.25 wt %, about 0.2 wt %, about 0.15 wt %, about 0.1 wt % THC, or less. In some embodiments, the compound of Formula (I), or a pharmaceutically acceptable salt thereof, is substantially free of THC. In some embodiments, the compound of Formula (I), or a pharmaceutically acceptable salt thereof, is substantially free of $\Delta^{(9,10)}$-tetrahydrocannabinol. In some embodiments, the compound of Formula (I), or a pharmaceutically acceptable salt thereof, is substantially free of $\Delta^{(8,9)}$-tetrahydrocannabinol and $\Delta^{(9,10)}$-tetrahydrocannabinol. In some embodiments, the compound of Formula (I) is cannabinol, or a pharmaceutically acceptable salt thereof.

In some embodiments of the methods of the present disclosure, a compound of Formula (IV), or a pharmaceutically acceptable salt thereof, is formed:

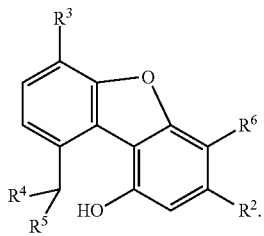

(IV)

In some embodiments, the compound of Formula (IV), or a pharmaceutically acceptable salt thereof, is formed in an amount of about 5 mol % or less, based on the total mols of the compound of Formula (I), or a pharmaceutically acceptable salt thereof. For example, the compound of Formula (IV), or a pharmaceutically acceptable salt thereof, is formed in an amount of less than about 5 mol %, such as less than about 4 mol %, less than about 3 mol %, less than about 2 mol %, or less than about 1 mol %, based on the total mols of the compound of Formula (I), or a pharmaceutically acceptable salt thereof. In some embodiments, the compound of Formula (IV) is cannabifuran, or a pharmaceutically acceptable salt thereof. In some embodiments, the cannabifuran, or a pharmaceutically acceptable salt thereof, is formed in an amount of less than about 5 mol %, based on the total mols of cannabinol, or a pharmaceutically acceptable salt thereof. In some embodiments, the compound of Formula (IV), or a pharmaceutically acceptable salt thereof, is dehydrocannabifuran. In some embodiments, the dehydrocannabifuran is formed in an amount of less than about 5 mol %, based on the total mols of cannabinol, or a pharmaceutically acceptable salt thereof.

In some embodiments, the compound of Formula (IV) is selected from the group of compounds delineated in Table 5, or a pharmaceutically acceptable salt thereof.

TABLE 5

| Trivial Name | Structure | IUPAC name |
|---|---|---|
| Cannabifuran (CBF) | 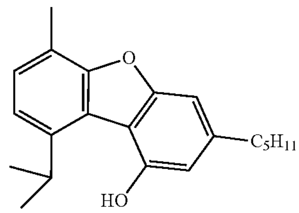 | 5-isopropyl-8-methyl-2-pentyl-9-oxa-4-fluorenol |
| Dehydrocannabifuran (DHCBF) | 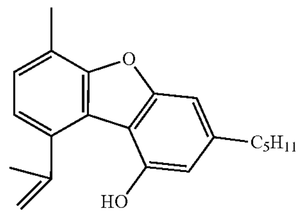 | 5-isopropenyl-8-methyl-2-pentyl-9-oxa-4-fluorenol |

In some embodiments, the methods disclosed herein further include crystallizing the compound of Formula (I), or a pharmaceutically acceptable salt thereof. In some embodiments, the crystallizing includes dissolving the compound of Formula (I), or a pharmaceutically acceptable salt thereof, in a solvent to form a solution. In some embodiments, the solvent is an aprotic organic solvent. In some embodiments, the aprotic organic solvent is hexane or heptane. In some embodiments, the crystallizing includes dissolving the compound of Formula (I), or a pharmaceutically acceptable salt thereof, in a solvent to form a solution where the temperature is at least about 35° C., such as about 35° C. to about 100° C., or about 40° C. to about 80° C., and cooling the solution to room temperature (e.g., about 20° C. to about 25° C.). In some embodiments, the cooling includes stirring the solution. In some embodiments, the crystallizing does not include seeding the solution.

In some embodiments, the compound of Formula (I), or a pharmaceutically acceptable salt thereof, has high purity (e.g., a purity of at least about 90%, at least about 95%, at least about 98%, or at least about 99%). For example, the compound of Formula (I), or a pharmaceutically acceptable salt thereof, can be at least 95%, 95.5%, 96%, 96.5%, 97%, 97.5%, 98%, 98.5%, 99%, 99.5%, 99.6%, 99.7%, 99.8%, 99.9%, or 99.99% pure. In some embodiments, the compound of Formula (I), or a pharmaceutically acceptable salt thereof, has a purity of at least about 95%, at least about 95.5%, at least about 96%, at least about 96.5%, at least about 97%, at least about 97.5%, at least about 98%, at least about 98.5%, at least about 99%, at least about 99.5%, at least about 99.6%, at least about 99.7%, at least about 99.8%, or at least about 99.9%. In some embodiments, the compound of Formula (I), or a pharmaceutically acceptable salt thereof, has a purity of at least about 99%. In some embodiments, the compound of Formula (I), or a pharmaceutically acceptable salt thereof, has a purity of at least about 99.5%. In some embodiments, the compound of Formula (I), or a pharmaceutically acceptable salt thereof, has a purity of at least about 99.9%. In some embodiments, the compound of Formula (I) is cannabinol, or a pharmaceutically acceptable salt thereof, and the cannabinol, or a pharmaceutically acceptable salt thereof, has a purity of at least about 95%, at least about 95.5%, at least about 96%, at least about 96.5%, at least about 97%, at least about 97.5%, at least about 98%, at least about 98.5%, at least about 99%, at least about 99.5%, at least about 99.6%, at least about 99.7%, at least about 99.8%, or at least about 99.9%. In some embodiments, the cannabinol, or a pharmaceutically acceptable salt thereof, has a purity of at least about 99%. In some embodiments, the cannabinol, or a pharmaceutically acceptable salt thereof, has a purity of at least about 99.5%. In some embodiments, the cannabinol, or a pharmaceutically acceptable salt thereof, has a purity of at least about 99.9%.

In some embodiments, the compound of Formula (I), or a pharmaceutically acceptable salt thereof, contains about 0.5 wt % THC or less, such as about 0.45 wt %, about 0.4 wt %, about 0.35 wt %, about 0.3 wt %, about 0.25 wt %, about 0.2 wt %, about 0.15 wt %, about 0.1 wt % THC, or less. In some embodiments, the compound of Formula (I), or a pharmaceutically acceptable salt thereof, contains less than the legal limit of THC, such as less than 0.3 wt % THC. In some embodiments, the compound of Formula (I), or a pharmaceutically acceptable salt thereof, is substantially free of THC. In some embodiments, the THC is $\Delta^{8(9)}$-iso-tetrahydrocannabinol ($\Delta^{8(9)}$-iso-THC), $\Delta^{4(8)}$-iso-tetrahydrocannabinol ($\Delta^{4(8)}$-iso-THC), $\Delta^{4(5)}$-iso-tetrahydrocannabinol ($\Delta^{4(5)}$-iso-THC), $\Delta^{8(9)}$-tetrahydrocannabinol ($\Delta^{8(9)}$-THC), $\Delta^{9(10)}$-tetrahydrocannabinol ($\Delta^{9(10)}$-THC), $\Delta^{10(10a)}$-tetrahydrocannabinol ($\Delta^{10(10a)}$-THC), or $\Delta^{6a(10a)}$-tetrahydrocannabinol ($\Delta^{6a(10a)}$-THC), or combinations thereof. In some embodiments, the compound of Formula (I), or a pharmaceutically acceptable salt thereof, contains about 0.5 wt % or less of $\Delta^{9(10)}$-THC. In some embodiments, the compound of Formula (I), or a pharmaceutically acceptable salt thereof, contains less than the legal limit of $\Delta^{9(10)}$-THC, such as less than 0.3 wt % $\Delta^{9(10)}$-THC. In some embodiments, the compound of Formula (I), or a pharmaceutically acceptable salt thereof, is substantially free of $\Delta^{9(10)}$-THC. Advantageously, the compound of Formula (I), or a pharmaceutically acceptable salt thereof, of the methods of the present disclosure contains THC (e.g., $\Delta^{9(10)}$-THC) in such an insignificant amount that the psychoactive effects of certain forms of THC (e.g., $\Delta^{9(10)}$-THC) are diminished or are completely absent when a subject is administered the compound of Formula (I), or a pharmaceutically acceptable salt thereof. In some embodiments, the compound of Formula (I) is cannabinol, or a pharmaceutically acceptable salt thereof.

In some embodiments, the methods of the present disclosure further include forming a compound of Formula (V), or a pharmaceutically acceptable salt thereof:

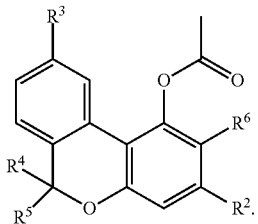

(V)

In some embodiments, the method includes admixing the compound of Formula (I), or a pharmaceutically acceptable salt thereof, where $R^1$ is hydrogen, with a dehydrating agent and acetic acid to form a compound of Formula (V), or a pharmaceutically acceptable salt thereof. In some embodiments, the compound of Formula (V) is CBN—OAc:

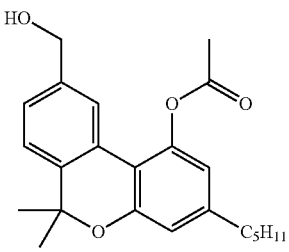

(CBN—OAc), or a pharmaceutically acceptable salt thereof.

In some embodiments, the methods of the present disclosure further include forming a compound of Formula (VI), or a pharmaceutically acceptable salt thereof:

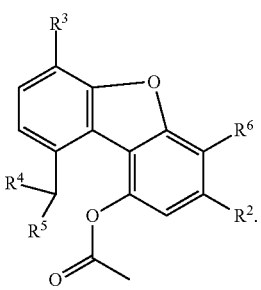

(VIa)

In some embodiments, the compound of Formula (VI), or a pharmaceutically acceptable salt thereof, is formed by admixing the compound of Formula (I), or a pharmaceutically acceptable salt thereof, where $R^1$ is hydrogen, with a dehydrating agent and acetic acid to form a compound of Formula (VI), or a pharmaceutically acceptable salt thereof. In some embodiments, the compound of Formula (VI), or a pharmaceutically acceptable salt thereof, is formed in an amount of less than about 5 mol %, based on the total mols of the compound of Formula (VI), or a pharmaceutically acceptable salt thereof. In some embodiments, the compound of Formula (VI) is CBF—OAc:

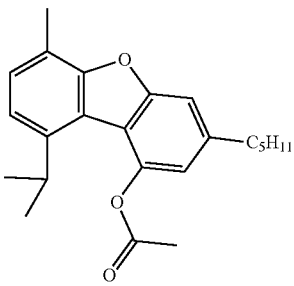

(CBF—OAc), or a pharmaceutically acceptable salt thereof.

In some embodiments, the dehydrating agent disclosed herein includes one or more of acetic anhydride, phosphoric acid, sulfuric acid, sodium bisulfite, phosphorus pentoxide, and polyphosphoric acid. In some embodiments, the dehydrating agent is polyphosphoric acid. In some embodiments, the dehydrating agent is acetic anhydride.

In some embodiments, the admixing of the compound of Formula (I), or a pharmaceutically acceptable salt thereof, where $R^1$ is hydrogen, with a dehydrating agent and acetic acid includes distilling the compound of Formula (I), or a pharmaceutically acceptable salt thereof, where $R^1$ is hydrogen, in the presence of the dehydrating agent and acetic acid.

In some embodiments, the compound of Formula (I), or a pharmaceutically acceptable salt thereof, is a compound of Formula (Ia):

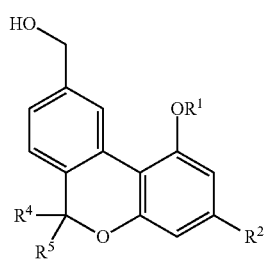

(Ia)

or a pharmaceutically acceptable salt thereof.

In some embodiments, the compound of Formula (II), or a pharmaceutically acceptable salt thereof, is a compound of Formula (IIa):

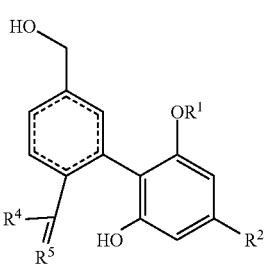

(IIa)

or a pharmaceutically acceptable salt thereof.

In some embodiments, the compound of Formula (III), or a pharmaceutically acceptable salt thereof, is a compound of Formula (IIIa):

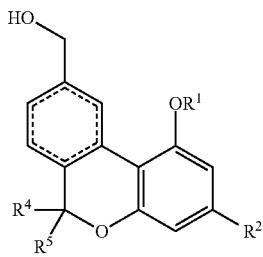

or a pharmaceutically acceptable salt thereof.

In some embodiments, the compound of Formula (IV), or a pharmaceutically acceptable salt thereof, is a compound of Formula (IVa):

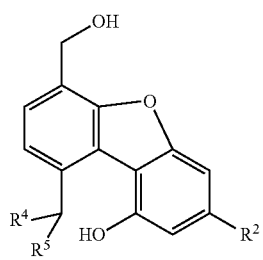

or a pharmaceutically acceptable salt thereof.

In some embodiments, the compound of Formula (V), or a pharmaceutically acceptable salt thereof, is a compound of Formula (Va):

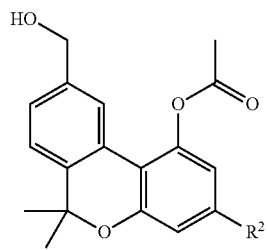

or a pharmaceutically acceptable salt thereof.

In some embodiments, the compound of Formula (VI), or a pharmaceutically acceptable salt thereof, is a compound of Formula (VIa):

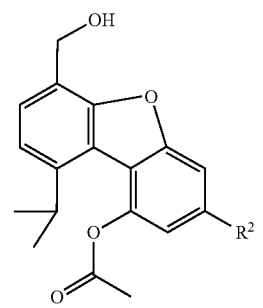

or a pharmaceutically acceptable salt thereof.

Also provided in the present disclosure are methods of preparing cannabinol, or a pharmaceutically acceptable salt thereof. In some embodiments, the method includes admixing a catalyst, cannabidiol, and an oxidizing agent to form cannabinol, or a pharmaceutically acceptable salt thereof, where the catalyst is $I_2$, $Br_2$, or $Cl_2$. In some embodiments, the admixing step includes: (a) reacting the catalyst and the cannabidiol to form tetrahydrocannabinol; and (b) reacting the tetrahydrocannabinol, the catalyst, and the oxidizing agent to form the cannabinol, or a pharmaceutically acceptable salt thereof.

In some embodiments, the method of preparing cannabinol, or a pharmaceutically acceptable salt thereof, includes admixing a catalyst, an oxidizing agent, and tetrahydrocannabinol to form cannabinol, or a pharmaceutically acceptable salt thereof, where the catalyst is $I_2$, $Br_2$, or $Cl_2$. In some embodiments, the THC is prepared by a process that includes admixing the catalyst and cannabidiol to form the THC.

In some embodiments, the method of preparing cannabinol, or a pharmaceutically acceptable salt thereof, includes: (a) admixing cannabidiol and a catalytic amount of $I_2$ to form a mixture of $\Delta^{(8,9)}$-tetrahydrocannabinol and $\Delta^{(9,10)}$-tetrahydrocannabinol; and (b) admixing the mixture and an oxidizing agent to form the cannabinol, or a pharmaceutically acceptable salt thereof. In some embodiments, the catalytic amount of $I_2$ is less than about 5 mol %, based on the total mols of the cannabidiol. In some embodiments, the catalytic amount of $I_2$ is less than about 4 mol %, based on the total mols of the cannabidiol. In some embodiments, the catalytic amount of $I_2$ is less than about 3 mol %, based on the total mols of the cannabidiol. In some embodiments, the catalytic amount of $I_2$ is less than about 2 mol %, based on the total mols of the cannabidiol. In some embodiments, the catalytic amount of $I_2$ is less than about 1 mol %, based on the total mols of the cannabidiol. In some embodiments, the catalytic amount of $I_2$ is about 0.5 mol %, based on the total mols of the cannabidiol. In some embodiments, the cannabinol, or a pharmaceutically acceptable salt thereof, is formed in about 50 mol % or more, about 75 mol % or more, or about 90 mol % or more yield, based on the total mols of cannabidiol.

In some embodiments, the method of preparing cannabinol, or a pharmaceutically acceptable salt thereof, includes admixing cannabidiol with $O_2$ and a catalytic amount of $I_2$ to form cannabinol, or a pharmaceutically acceptable salt thereof. In some embodiments, the $O_2$ is present in a gaseous mixture that contains an inert gas. In some embodiments, the inert gas is $N_2$. In some embodiments, the amount of $O_2$ in the gaseous mixture is less than about 25 wt %, less than about 20 wt %, less than about 15 wt %, or about 10 wt % to about 20 wt %, based on the total weight of the gaseous mixture. In some embodiments, the catalytic amount of $I_2$ is less than about 5 mol %, based on the total mols of the cannabidiol. In some embodiments, the catalytic amount of $I_2$ is less than about 4 mol %, based on the total mols of the cannabidiol. In some embodiments, the catalytic amount of $I_2$ is less than about 3 mol %, based on the total mols of the cannabidiol. In some embodiments, the catalytic amount of $I_2$ is less than about 2 mol %, based on the total mols of the cannabidiol. In some embodiments, the catalytic amount of $I_2$ is less than about 1 mol %, based on the total mols of the cannabidiol. In some embodiments, the catalytic amount of $I_2$ is about 0.5 mol %, based on the total mols of the cannabidiol. In some embodiments, the cannabinol, or a pharmaceutically acceptable salt thereof, has a purity of about 90% or more, about 95% or more, or about 99% or more, such as 99.1%, 99.2%, 99.3%, 99.4%, 99.5%, 99.6%, 99.7%, 99.8%, or 99.9%.

Also provided herein are methods of preparing cannabinol, or a pharmaceutically acceptable salt thereof. In some embodiments, the method includes: admixing cannabidiol, $O_2$, $I_2$, and a solvent to form a mixture that contains cannabinol, or a pharmaceutically acceptable salt thereof, and cannabifuran, or a pharmaceutically acceptable salt thereof; where the $I_2$ is present in an amount of about 10 mol % or less, based on the total mols of the cannabidiol; where the cannabinol, or a pharmaceutically acceptable salt thereof, has a purity of at least about 90%; and where the cannabifuran, or a pharmaceutically acceptable salt thereof, is present in the mixture in an amount of about 5 mol % or less, based on the total mols of cannabinol, or a pharmaceutically acceptable salt thereof. In some embodiments, the cannabinol, or a pharmaceutically acceptable salt thereof, is substantially free of $\Delta^{(8,9)}$-tetrahydrocannabinol and $\Delta^{(9-10)}$-tetrahydrocannabinol.

Also provided in the present disclosure are methods of preparing cannabifuran, or a pharmaceutically acceptable salt thereof. In some embodiments, the method includes admixing a catalyst, cannabidiol, and an oxidizing agent to form a mixture containing cannabinol, or a pharmaceutically acceptable salt thereof, and cannabifuran, or a pharmaceutically acceptable salt thereof, where the catalyst is $I_2$, $Br_2$, or $Cl_2$. In some embodiments, the admixing step includes: (a) reacting the catalyst and the cannabidiol to form tetrahydrocannabinol; and (b) reacting the tetrahydrocannabinol, the catalyst, and the oxidizing agent to form the mixture containing cannabinol or a pharmaceutically acceptable salt thereof, and cannabifuran, or a pharmaceutically acceptable salt thereof. In some embodiments, the method includes isolating the cannabifuran, or pharmaceutically acceptable salt thereof, from the mixture.

In some embodiments, the method of preparing cannabifuran, or a pharmaceutically acceptable salt thereof, includes admixing a catalyst, an oxidizing agent, and tetrahydrocannabinol to form a mixture containing cannabinol, or a pharmaceutically acceptable salt thereof, and cannabifuran, or a pharmaceutically acceptable salt thereof, where the catalyst is $I_2$, $Br_2$, or $Cl_2$. In some embodiments, the method includes isolating the cannabifuran, or pharmaceutically acceptable salt thereof, from the mixture. In some embodiments, the THC is prepared by a process that includes admixing the catalyst and cannabidiol to form the THC.

Also provided in the present disclosure are methods of preparing acetylcannabinol (CBN—OAc), or a pharmaceutically acceptable salt thereof. In some embodiments, the method includes: admixing cannabidiol, an oxidizing agent, a catalyst, and a solvent to form a mixture containing cannabinol; and admixing the mixture with a dehydrating agent and acetic acid to form acetylcannabinol, or a pharmaceutically acceptable salt thereof. In some embodiments, the catalyst is $I_2$. In some embodiments, the catalyst is present in an amount of less than about 5 mol %, based on the total mols of the cannabidiol. In some embodiments, the oxidizing agent is a peroxide. In some embodiments, the oxidizing agent is $O_2$.

In some embodiments, the method of preparing acetylcannabinol, or a pharmaceutically acceptable salt thereof, includes: admixing cannabidiol, $O_2$, a catalytic amount of $I_2$, and acetic acid to form a mixture containing cannabinol; and admixing the mixture with a dehydrating agent to form acetylcannabinol, or a pharmaceutically acceptable salt thereof. In some embodiments, the $O_2$ is present in a gaseous mixture including an inert gas. In some embodiments, the inert gas is $N_2$. In some embodiments, the amount of $O_2$ in the gaseous mixture is less than about 25 wt %, less than about 20 wt %, less than about 15 wt %, or about 10 wt % to about 20 wt %, based on the total weight of the gaseous mixture. In some embodiments, the catalytic amount of $I_2$ is less than about 5 mol %, based on the total mols of the cannabidiol. In some embodiments, the catalytic amount of $I_2$ is less than about 4 mol %, based on the total mols of the cannabidiol. In some embodiments, the catalytic amount of $I_2$ is less than about 3 mol %, based on the total mols of the cannabidiol. In some embodiments, the catalytic amount of $I_2$ is less than about 2 mol %, based on the total mols of the cannabidiol. In some embodiments, the catalytic amount of $I_2$ is less than about 1 mol %, based on the total mols of the cannabidiol. In some embodiments, the catalytic amount of $I_2$ is about 0.5 mol %, based on the total mols of the cannabidiol. In some embodiments, the cannabinol, or a pharmaceutically acceptable salt thereof, has a purity of about 90% or more, about 95% or more, or about 99% or more, such as 99.1%, 99.2%, 99.3%, 99.4%, 99.5%, 99.6%, 99.7%, 99.8%, or 99.9%. In some embodiments, the dehydrating agent is selected from acetic anhydride and polyphosphoric acid. In some embodiments, the dehydrating agent is acetic anhydride. In some embodiments, the dehydrating agent is polyphosphoric acid. In some embodiments, the method is performed in a single vessel without purifying the mixture containing the cannabinol prior to admixing the mixture with the dehydrating agent.

In some embodiments, the method of preparing acetylcannabinol, or a pharmaceutically acceptable salt thereof, includes admixing cannabinol, or a pharmaceutically acceptable salt thereof, a dehydrating agent, and acetic acid to form acetylcannabinol, or a pharmaceutically acceptable salt thereof. In some embodiments, the dehydrating agent is selected from acetic anhydride and polyphosphoric acid. In some embodiments, the dehydrating agent is acetic anhydride. In some embodiments, the dehydrating agent is polyphosphoric acid.

Also provided in the present disclosure are methods of preparing acetylcannabifuran, or a pharmaceutically acceptable salt thereof. In some embodiments, the method includes: admixing cannabidiol, an oxidizing agent, a catalytic amount of $I_2$, and a solvent to form a mixture containing cannabinol and cannabifuran; and admixing the mixture with a dehydrating agent and acetic acid to form a mixture containing acetylcannabinol, or a pharmaceutically acceptable salt thereof, and acetylcannabifuran, or a pharmaceutically acceptable salt thereof. In some embodiments, the method includes isolating the acetylcannabifuran, or pharmaceutically acceptable salt thereof, from the acetylcannabinol, or a pharmaceutically acceptable salt thereof. In some embodiments, the oxidizing agent is a peroxide. In some embodiments, the oxidizing agent is $O_2$.

In some embodiments, the method of preparing acetylcannabifuran, or a pharmaceutically acceptable salt thereof, includes: admixing cannabidiol, $O_2$, a catalytic amount of $I_2$, and acetic acid to form a mixture containing cannabinol; and admixing the mixture with a dehydrating agent to form a mixture containing acetylcannabinol, or a pharmaceutically acceptable salt thereof, and acetylcannabifuran, or a pharmaceutically acceptable salt thereof. In some embodiments, the method includes isolating the acetylcannabifuran, or pharmaceutically acceptable salt thereof, from the acetylcannabinol, or a pharmaceutically acceptable salt thereof. In some embodiments, the $O_2$ is present in a gaseous mixture including an inert gas. In some embodiments, the inert gas is $N_2$. In some embodiments, the amount of $O_2$ in the gaseous mixture is less than about 25 wt %, less than about 20 wt %, less than about 15 wt %, or about 10 wt % to about 20 wt %, based on the total weight of the gaseous mixture. In some embodiments, the catalytic amount of $I_2$ is less than about 5 mol %, based on the total mols of the cannabidiol. In some embodiments, the catalytic amount of $I_2$ is less than about 4 mol %, based on the total mols of the cannabidiol. In some embodiments, the catalytic amount of $I_2$ is less than about 3 mol %, based on the total mols of the cannabidiol. In some embodiments, the catalytic amount of $I_2$ is less than about 2 mol %, based on the total mols of the cannabidiol. In some embodiments, the catalytic amount of $I_2$ is less than about 1 mol %, based on the total mols of the cannabidiol. In some embodiments, the catalytic amount of $I_2$ is about 0.5 mol %, based on the total mols of the cannabidiol. In some embodiments, the cannabinol, or a pharmaceutically acceptable salt thereof, has a purity of about 90% or more, about 95% or more, or about 99% or more, such as 99.1%, 99.2%, 99.3%, 99.4%, 99.5%, 99.6%, 99.7%, 99.8%, or 99.9%. In some embodiments, the dehydrating agent is selected from acetic anhydride and polyphosphoric acid. In some embodiments, the dehydrating agent is acetic anhydride. In some embodiments, the dehydrating agent is polyphosphoric acid. In some embodiments, the method is performed in a single vessel without purifying the mixture containing the cannabinol prior to admixing the mixture with the dehydrating agent.

In some embodiments, the method of preparing acetylcannabifuran, or a pharmaceutically acceptable salt thereof, includes admixing cannabinol, a dehydrating agent, and acetic acid to form a mixture containing acetylcannabinol, or a pharmaceutically acceptable salt thereof, and acetylcannabifuran, or a pharmaceutically acceptable salt thereof. In some embodiments, the method includes isolating the acetylcannabifuran, or pharmaceutically acceptable salt thereof, from the acetylcannabinol, or a pharmaceutically acceptable salt thereof. In some embodiments, the dehydrating agent is selected from acetic anhydride and polyphosphoric acid. In some embodiments, the dehydrating agent is acetic anhydride. In some embodiments, the dehydrating agent is polyphosphoric acid.

Also provided herein are methods of preparing a mixture of CBN—OAc and CBF—OAc, or pharmaceutically acceptable salts thereof. In some embodiments, the method includes: (a) admixing a catalyst, an oxidizing agent, and CBD in a single vessel to form CBN; and (b) in the single vessel, admixing a dehydrating agent, acetic acid, and CBN, to form the mixture of CBN—OAc and CBF—OAc, or pharmaceutically acceptable salts thereof, where the catalyst is $I_2$, $Br_2$, or $Cl_2$.

Compositions

Provided in the present disclosure are compositions that contain cannabinol, or a pharmaceutically acceptable salt thereof prepared according to the methods of the disclosure, and one or more additional cannabinoids, or pharmaceutically acceptable salts thereof. In some embodiments, provided is a composition that contains cannabinol, or a pharmaceutically acceptable salt thereof, and a cannabinoid of Table 1, or a pharmaceutically acceptable salt thereof. In some embodiments, the composition contains cannabinol, or a pharmaceutically acceptable salt thereof, and a cannabinoid of Table 1, or a pharmaceutically acceptable salt thereof in a ratio of 100:1 to 1:1, respectively. For example, the composition can contain cannabinol, or a pharmaceutically acceptable salt thereof, and a cannabinoid of Table 1, or a pharmaceutically acceptable salt thereof in a ratio 100:1 to 5:1, 100:1 to 10:1, 100:1 to 25:1, 100:1 to 50:1, 100:1 to 75:1, 100:1 to 90:1, 10:1 to 1:1, 5:1 to 1:1, or 3:1 to 1:1, respectively. In some embodiments, the composition contains cannabinol, or a pharmaceutically acceptable salt thereof, and cannabifuran, or a pharmaceutically acceptable salt thereof. In some embodiments, the cannabinol, or a pharmaceutically acceptable salt thereof, and the cannabifuran, or a pharmaceutically acceptable salt thereof, are present in the composition in a ratio of 100:1 to 1:1, respectively. For example, the cannabinol, or a pharmaceutically acceptable salt thereof, and the cannabifuran, or a pharmaceutically acceptable salt thereof can be present in the composition in a ratio of 100:1 to 5:1, 100:1 to 10:1, 100:1 to 25:1, 100:1 to 50:1, 100:1 to 75:1, 100:1 to 90:1, 10:1 to 1:1, 5:1 to 1:1, or 3:1 to 1:1, respectively.

Provided in the present disclosure are compositions containing cannabivarin, or a pharmaceutically acceptable salt thereof, prepared according to the methods of the disclosure and cannabifuranvarin, or a pharmaceutically acceptable salt thereof prepared according to the methods of the disclosure. In some embodiments, the cannabivarin, or a pharmaceutically acceptable salt thereof, and the cannabifuranvarin, or a pharmaceutically acceptable salt thereof are present in the composition in a ratio of 100:1 to 1:1, respectively. For example, the cannabivarin, or a pharmaceutically acceptable salt thereof, and the cannabifuranvarin, or a pharmaceutically acceptable salt thereof can be present in the composition in a ratio of 100:1 to 5:1, 100:1 to 10:1, 100:1 to 25:1, 100:1 to 50:1, 100:1 to 75:1, 100:1 to 90:1, 10:1 to 1:1, 5:1 to 1:1, or 3:1 to 1:1, respectively.

Provided in the present disclosure are compositions containing acetylcannabinol (CBN—OAc), or a pharmaceutically acceptable salt thereof, prepared according to the methods of the disclosure and acetylcannabifuran (CBF—OAc), or a pharmaceutically acceptable salt thereof prepared according to the methods of the disclosure. In some embodiments, the CBN—OAc, or a pharmaceutically acceptable salt thereof, and the CBF—OAc, or a pharmaceutically acceptable salt thereof are present in the composition in a ratio of 100:1 to 1:1, respectively. For example, the CBN—OAc, or a pharmaceutically acceptable salt thereof, and the CBF—OAc, or a pharmaceutically acceptable salt thereof can be present in the composition in a ratio of 100:1 to 5:1, 100:1 to 10:1, 100:1 to 25:1, 100:1 to 50:1, 100:1 to 75:1, 100:1 to 90:1, 10:1 to 1:1, 5:1 to 1:1, or 3:1 to 1:1, respectively.

Typically, cannabinoids act on cannabinoid receptors on cells that repress neurotransmitter release in the brain. However, it has surprisingly been found that in the methods of the present disclosure, the cannabinoid inhibits oxytosis/ferroptosis independently of cannabinoid receptors. In some embodiments, the cannabinoid is cannabinol and the cannabinol inhibits oxytosis/ferroptosis independently of cannabinoid receptors.

The cannabinoid or cannabinoid derivative used in the method of the present disclosure can be administered in an amount of about 1 mg/kg/day to about 50 mg/kg/day. For example, the cannabinoid can be administered in an amount of about 5 mg/kg/day to about 30 mg/kg/day, or about 10 mg/kg/day to 20 mg/kg/day. In some embodiments, the cannabinoid is administered in an amount of about 10 mg/kg/day to 20 mg/kg/day. In some embodiments, the cannabinoid is administered in an amount of about 10 mg/kg/day. In some embodiments, the cannabinoid is administered in an amount of about 20 mg/kg/day. In some embodiments, the cannabinoid is cannabinol and the cannabinol is administered in an amount of about 1 mg/kg/day to about 50 mg/kg/day, or about 5 mg/kg/day to about 30 mg/kg/day, or about 10 mg/kg/day to 20 mg/kg/day. For example, the cannabinol is administered in an amount of about 10 mg/kg/day to 20 mg/kg/day. In some embodiments, the cannabinol is administered in an amount of about 10 mg/kg/day. In some embodiments, the cannabinol is administered in an amount of about 20 mg/kg/day.

EXAMPLES

Material and Methods

Chemicals and Reagents: All solvents and reagents were purchased from commercial sources and were used without further purification.

Mass Spectrometry (MS): High-resolution mass spectrometric (HRMS) data were obtained on a Thermo Q-Exactive Quadrupole-Orbitrap mass spectrometer in positive mode. Samples were diluted with a 95:5 mixture of methanol and water containing 0.1% formic acid and then introduced by direct electrospray infusion. Accurate masses of all analytes were obtained from the pseudo-molecule [M+H]$^+$ and were within 3 ppm mass error. Full MS scans were recorded for the 150-2000 m/z range.

Nuclear magnetic resonance (NMR): $^1$H and $^{13}$C NMR data were collected at 298 K on a 600 MHz Bruker Avance III spectrometer fitted with a 5 mm triple resonance probe with z-axis gradients. NMR spectra were collected in DMSO-D$_6$ and referenced to tetramethylsilane. Resonance multiplicities are denoted s, d, t, q, m, and br for singlet, doublet, triplet, quartet, multiplet, and broad, respectively.

Melting Point Analysis of CBN: Melting point ranges were determined using a model RD-MP2 digital melting point determination apparatus.

Figure 4:
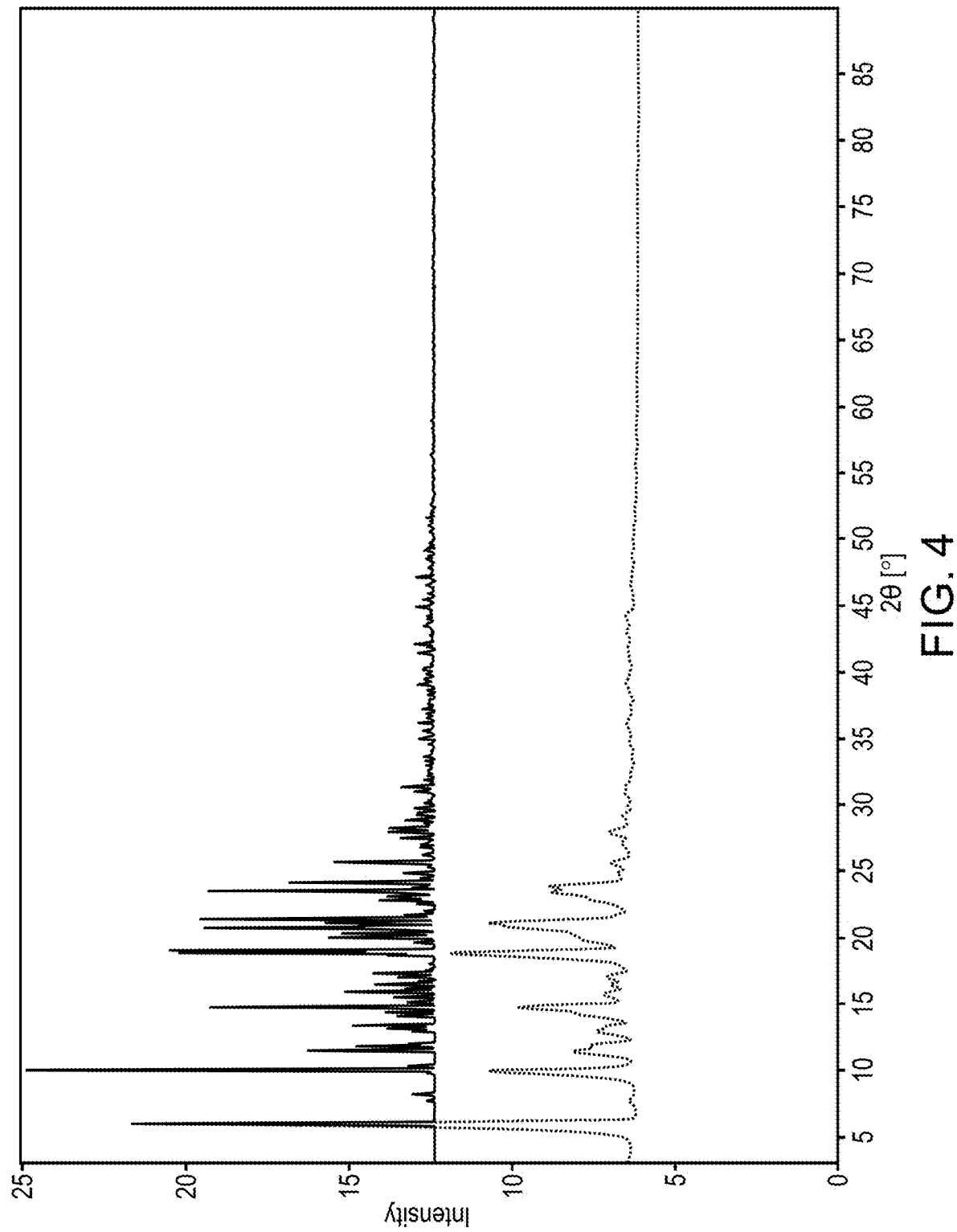
FIG. 4 shows an X-ray powder diffraction spectrum (bottom) and a single crystal X-ray diffraction spectrum (top) of the CBN of the disclosure.

XRD analysis of CBN (FIG. 4): Powder diffraction data was collected using a Rigaku Smartlab diffractometer. The single crystal diffraction data shown in FIG. 4 was calculated from the powder diffraction data collected.

Example 1: Synthesis of Cannabinol and Derivatives Thereof

Synthesis of CBN from CBD Via "Two Step in One Pot" Continuous In Situ Process Using Diiodine as Homogeneous Catalyst and Dioxygen as Oxidizing Agent

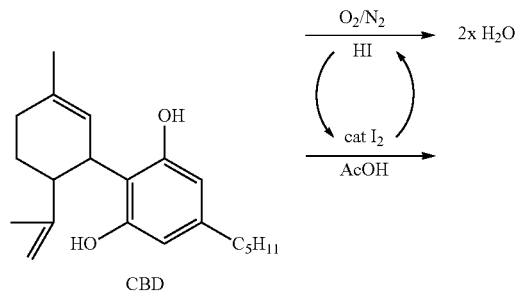

CBD

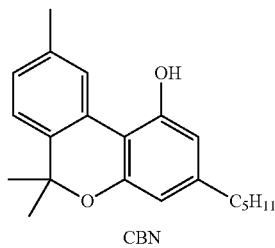

CBN

CBD (163 g, 0.518 mol) was charged to a glass pressure reactor equipped with magnetic stirrer and a temperature controller. Elemental iodine (0.68 g, 0.0027 mol, 0.5% catalytic mol equivalents) was charged to the reactor as well as 126 g of glacial acetic acid to form a mixture. This mixture was stirred together at room temperature.

The temperature of the mixture was increased to 70° C. for cyclization. After stirring at this temperature for 3 hours, analysis by high performance liquid chromatography-ultraviolet spectroscopy (HPLC-UV) showed that CBD cyclization was >90% complete.

The reactor was pressurized to 40 psig with dry compressed air. Flow of 0.5 to 0.75 liters per minute was established through the reactor via a purge valve. Upon pressurization with air the mixture changed color reflecting the initiation of a redox cycle between diiodine and hydroiodic acid involving the reduction of dioxygen to water. The mixture was heated to 130° C. for 40 hours until GCMS analysis (FIG. 1) showed that reaction intermediates fell below 0.3% area under the curve (AUC).

The mixture was combined with 160 mL water. CBN was extracted into 250 g isopropyl acetate. The acidic aqueous layer was removed, and the organic phase washed and the diiodine was quenched using an aqueous sodium thiosulfate solution. The washed and quenched organic layer was stripped by rotary evaporation yielding 162 grams of crude reaction product. The crude product was composed of >90% CBN and contained ~1% cannabifuran (CBF).

The crude product was vacuum distilled yielding 100 grams of distillate which was dissolved in 500 mL of hot n-heptane and crystallized without seeding upon cooling to 20° C. while stirring. This crystallization afforded pure CBN which was dried overnight in a vacuum oven at 70° C. under reduced pressure. The final mass of CBN collected was 93 grams (0.3 mol), for an overall 57.9% yield. Final product quality of CBN was confirmed at >99% pure.

The identity of CBN was confirmed by high-resolution nuclear magnetic resonance (NMR) and mass spectrometry (MS) analyses. $^1$H NMR (600 MHz, Dimethylsulfoxide-D$_6$) δ 9.87 (s, 1H), 8.27 (s, 1H), 7.17 (d, J=7.8 Hz, 1H), 7.04 (d, J=7.8 Hz, 1H), 6.39 (s, 1H), 6.24 (s, 1H), 2.43 (t, J=7.7 Hz, 2H), 2.30 (s, 3H), 1.54 (p, 2H), 1.49 (s, 6H), 1.29 (m, 4H), 0.87 (t, J=7.2 Hz, 3H). $^{13}$C NMR (150 MHz, Dimethylsulfoxide-D$_6$) δ 14.4, 21.7, 22.4, 27.4, 30.4, 31.4, 35.3, 77.0, 108.1, 109.0, 110.0, 122.9, 126.9, 127.5, 128.2, 136.2, 136.5, 144.0, 154.3, 155.7. HR-MS m/z [M+H]$^+$ 311.2000 (calculated for $C_{21}H_{27}O_2^+$, 311.2006, 1.93 ppm error).

The identity of the CBN of the disclosure was also confirmed by X-ray powder diffraction analysis shown in Table A below.

TABLE A

| No. | 2-theta(deg) | d(ang.) | Height(cps) | FWHM(deg) | Int. I(cps deg) | Int. W(deg) | Asym. factor |
|---|---|---|---|---|---|---|---|
| 1 | 5.821(16) | 15.17(4) | 58(7) | 0.33(2) | 26.9(9) | 0.47(7) | 1.8(4) |
| 2 | 9.73(5) | 9.08(4) | 19(4) | 0.42(4) | 8.5(10) | 0.45(15) | 1.7(8) |
| 3 | 14.45(6) | 6.12(2) | 11(3) | 0.41(8) | 6.6(8) | 0.6(2) | 0.9(6) |
| 4 | 18.67(3) | 4.749(9) | 20(4) | 0.47(3) | 10.1(6) | 0.50(13) | 1.9(6) |
| 5 | 20.88(2) | 4.251(4) | 12(3) | 0.98(6) | 13.1(9) | 1.1(3) | 3.7(11) |
| 6 | 23.35(11) | 3.806(18) | 7(2) | 0.92(9) | 7.4(10) | 1.0(5) | 1.2(6) |

Figure 2:
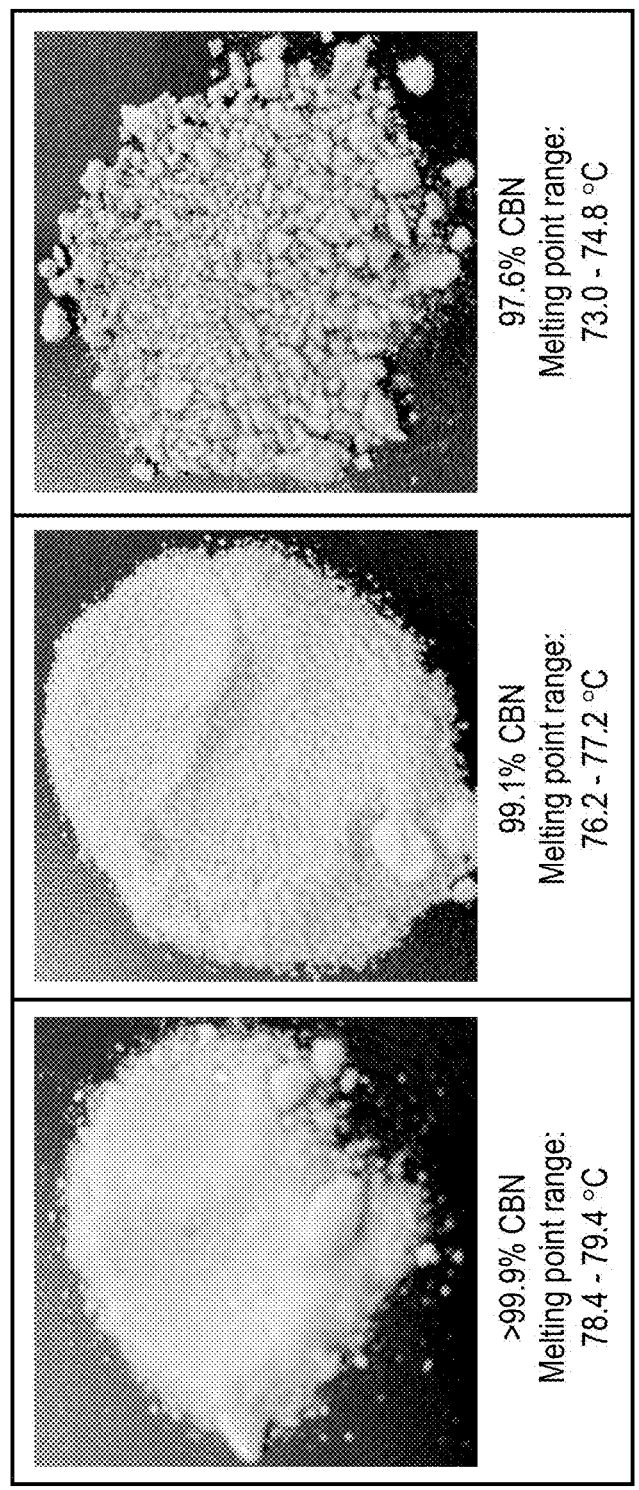
FIG. 2 depicts photographic images of three samples of CBN with different purities.
Figure 3:
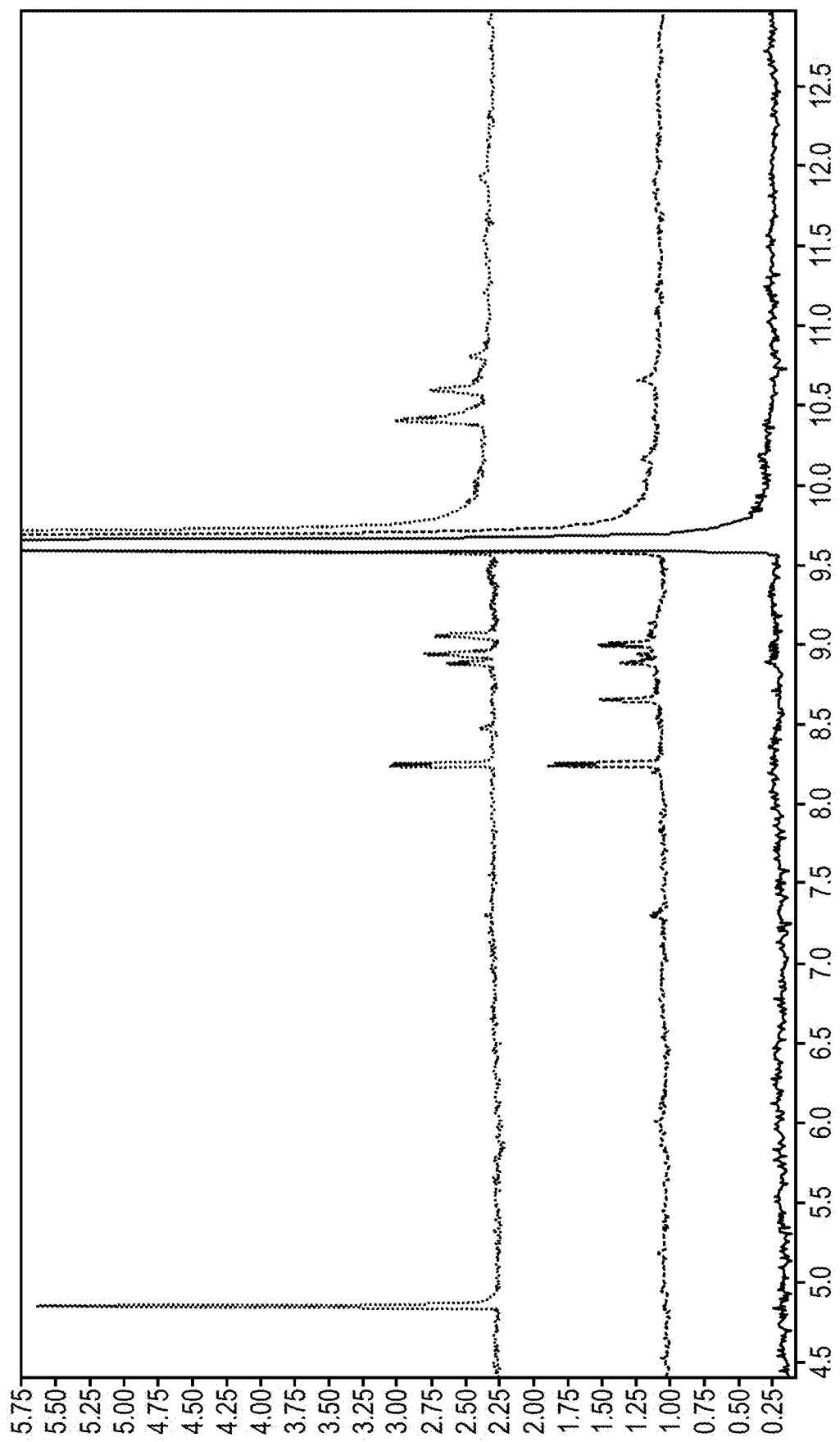
FIG. 3 shows the mass spectra of three samples of CBN with different purities, where the top spectrum represents a sample that is 97.6% pure (crude), the middle spectrum represents a sample that is 99.1% pure, and the bottom spectrum represents a sample that is >99.9% pure.

Melting point analysis of three different CBN samples was accomplished. Sample 1 was CBN of >99.9% purity (white), Sample 2 was CBN of about 99.1% purity (beige), and Sample 3 was crude CBN of about 97.6% purity (brown) (FIG. 2; colors not shown). The purity was tested via mass spectrometry shown in FIG. 3, where the bottom spectrum was CBN with >99.9% purity, the middle spectrum was CBN of 99.1% purity; and the top spectrum was CBN with 97.6% purity. As shown in FIG. 2, the melting points of the three samples differed based on purity.

Synthesis of CBN from CBD Via "Two Step in One Pot" Continuous In Situ Process Using Diiodine as Homogeneous Catalyst and Elemental Sulfur as Oxidizing Agent:

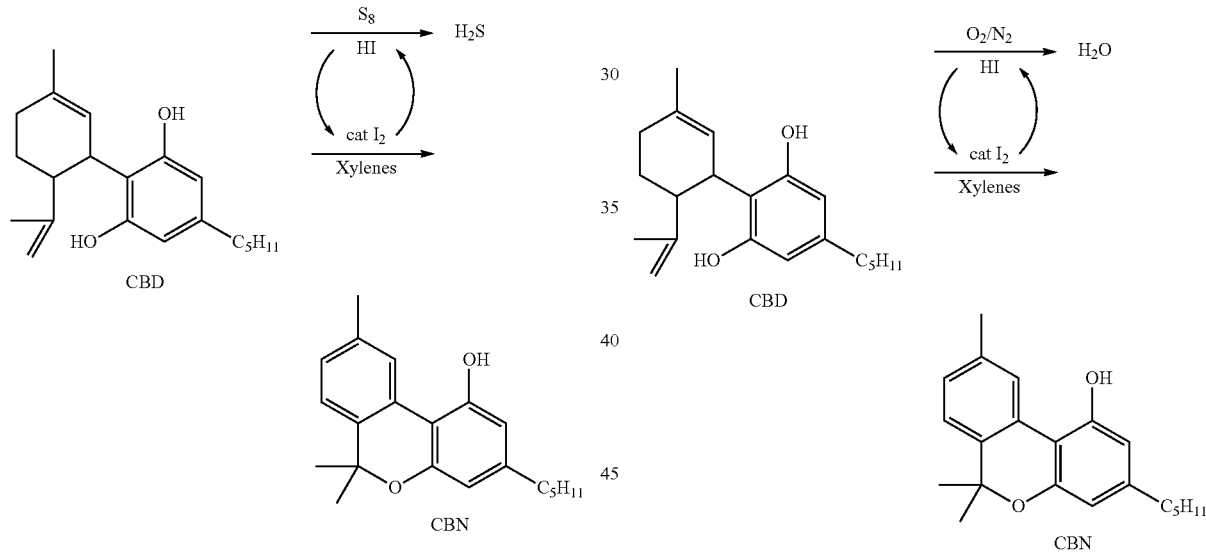

CBD (20000 g, 63.69 mol) was charged to a glass reactor equipped with overhead stirrer and a temperature controller. Elemental iodine (100 g, 0.39 mol, 0.6% catalytic mol equivalents) was charged to the reactor as well as 10000 mL of xylenes to form a mixture. This mixture was stirred together at room temperature.

The temperature of the mixture was increased to 75° C. for cyclization. After stirring at this temperature for at least 2 hours analysis by GCMS showed that CBD cyclization was at least 95% complete.

Elemental sulfur (4076 g, 127.4 mol, 2.0 mol equivalents) was added to the mixture, and the temperature was increased to 135° C. After heating for 4 hours GCMS analysis showed that reaction intermediates fell below 0.3% AUC.

The reaction mixture was washed with 10000 mL water. The acidic aqueous layer was removed, and the organic phase washed and the diiodine was quenched using an aqueous sodium thiosulfate solution. The washed and quenched organic layer was stripped by rotary evaporation yielding 18982 grams of crude reaction product.

The crude product was vacuum distilled at 150 mtorr and 180° C., yielding 14534 grams of distillate which was dissolved in 20000 mL of hot n-heptane and crystallized upon cooling to 20° C. while stirring. This crystallization afforded pure crystalline CBN which was dried overnight in a vacuum oven at 70° C. under reduced pressure. The final mass of CBN collected was 11617 grams (37.47 mol), for an overall 58.8% yield. Final product quality was confirmed at >99% pure by GCMS analysis.

Synthesis of CBN from CBD Via "Two Step in One Pot" Continuous In Situ Process Using Diiodine as Homogeneous Catalyst and Dioxygen as Oxidizing Agent:

CBD (314 g, 1 mol) was charged to a glass reactor equipped with magnetic stirrer and a temperature controller. Elemental iodine (2.54 g, 0.01 mol, 1.0% catalytic mol equivalents) was charged to the reactor as well as 1000 mL of xylenes to form a mixture. This mixture was stirred together at room temperature.

Dry compressed air was added to the mixture at a rate of 3 liters per minute via gas dispersion tube, and the temperature was increased to 100° C. After heating for 24 hours, the temperature was increased to 135° C. and the mixture was heated for an additional 24 hours until GCMS analysis showed that reaction intermediates fell below 0.3% AUC.

The reaction mixture was washed with 1000 mL water. The acidic aqueous layer was removed, and the organic phase washed and the diiodine was quenched using an aqueous sodium thiosulfate solution. The washed and quenched organic layer was stripped by rotary evaporation yielding 282 grams of crude product, CBN.

The crude product was vacuum distilled at 150 mtorr and 180° C., yielding 210 grams of distillate which was dissolved in 1000 mL of hot n-heptane and crystallized upon cooling to 20° C. while stirring. This crystallization afforded pure crystalline CBN which was dried overnight in a vacuum oven at 70° C. under reduced pressure. The final mass of CBN collected was 161 grams (0.52 mol), for an overall 52% yield. Final product quality was confirmed at >99% pure by GCMS analysis.

HRMS data was collected on CBN shown in Table 6 below.

TABLE 6

| Formula | Species | Structure | Calculated Mass (M/Z) | Observed Mass (M/Z) | Calculated Error (PPM) |
|---|---|---|---|---|---|
| $C_{21}H_{26}O_2$ | Molecule | 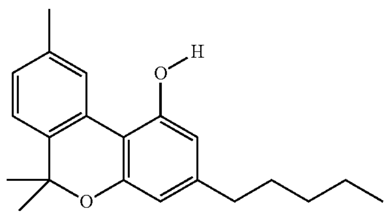 [SMILES: CCCCCc1cc(O)c2c(c1)OC(C)(C)c1ccc(C)cc1-2] | 310.1933 | | |
| $C_{21}H_{27}O_2^+$ | $[M + H]^+$ ion | 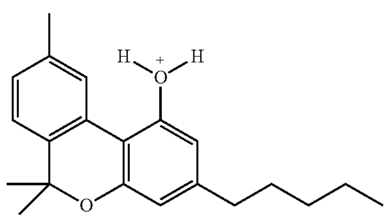 | 311.2006 | 311.2000 | 1.93 |
| $C_{21}H_{26}O_2 + Na^+$ | $[M + Na]^+$ adduct | 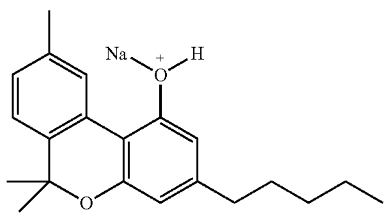 | 333.1825 | 333.1819 | 1.80 |

Example 2: Synthesis of Acetylcannabinol and Derivatives Thereof

Synthesis of CBN—OAc from CBD:

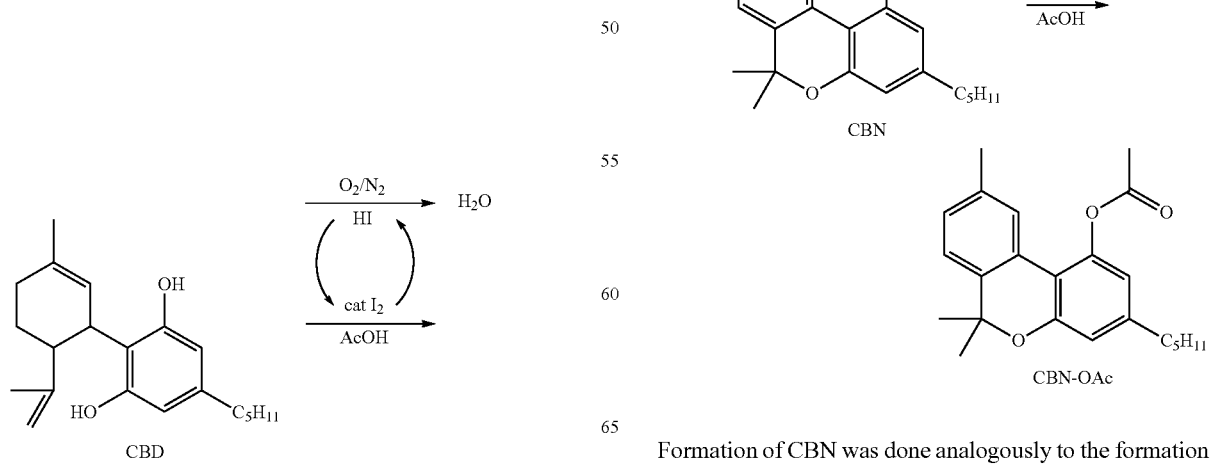

Formation of CBN was done analogously to the formation of CBN in Example 1 above. CBN (157 g, 0.5 mol) was heated and stirred in acetic acid (200 mL) in a 1000 mL round bottom flask, then polyphosphoric acid (63.9 g, 0.75 mol, 1.5 EQ) was added and the mixture was allowed to reflux for 18 hours. Water was added (250 mL) and the crude acetylcannabinol was extracted into isopropyl acetate (200 mL). Isopropyl acetate was removed by rotary evaporation, then the crude acetylcannabinol was dissolved in hot ethanol (500 mL) and crystallized upon cooling, yielding 126 g (0.36 mol, 72% yield) of white crystalline powder measuring >99.5% CBN—OAc by GCMS (AUC).

Formation of CBN was done analogously to the formation of CBN in Example 1 above. CBN (2000 g, 6.45 mol) was dissolved in acetic anhydride (1000 mL, 10.6 mol, 1.6 EQ) in a 5000 mL round bottom flask. A short path distillation apparatus was attached to the flask, and the acetic anhydride was removed by distillation under atmosphere by stirring while heating the mixture between 140-260° C. The resultant crude acetylcannabinol was dissolved in hot ethanol (8000 mL) and crystallized upon cooling, yielding 1930 g (5.48 mol, 85% yield) of white crystalline powder which measured >99.9% CBN—OAc by GCMS (AUC).

Formation of CBN was done analogously to the formation of CBN in Example 1 above. CBN (310 g, 1.0 mol) was dissolved in xylenes (500 mL) in a 3000 mL round bottom flask, to which was added acetic anhydride (190 mL, 2 mol, 2 EQ) and N,N-diisopropylethylamine (350 mL, 2 mol, 2 EQ), The mixture was stirred and heated at 100° C. for 24 hours. The mixture was cooled and was successively washed with three 600 mL portions of water. The organic layer was concentrated by rotary evaporation and the crude acetylcannabinol was dissolved in hot ethanol (1200 mL) and crystallized upon cooling, yielding 282 g (0.80 mol, 80% yield) of white crystalline powder measuring >99.5% CBN—OAc by GCMS (AUC).

Synthesis of CBN—OAc from CBD

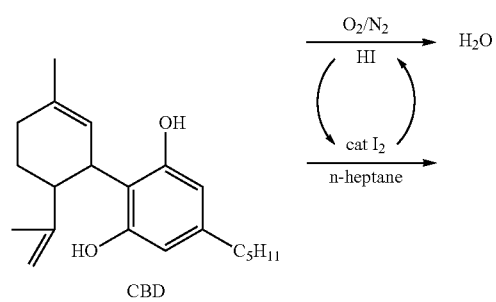

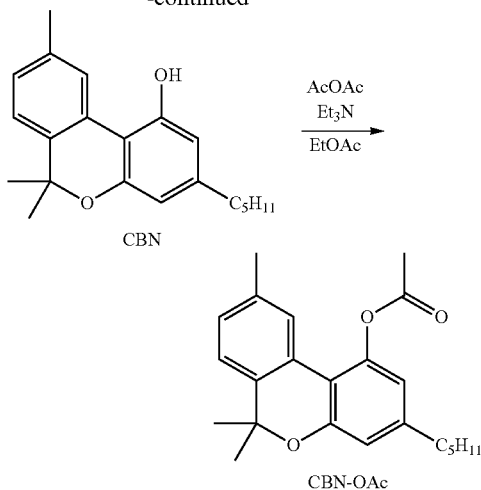

CBD (600 g, 1.91 mol) was charged to a glass reactor equipped with magnetic stirrer and a temperature controller. Elemental iodine (7.5 g, 0.03 mol, 1.6% catalytic mol equivalents) was charged to the reactor as well as 3000 mL of n-heptane to form a mixture. This mixture was stirred together at 80° C. Dry compressed 5% $O_2$ was added to the mixture at a rate of 0.5 liters per minute via gas dispersion tube. The mixture was heated for 216 hours until GCMS analysis showed that reaction intermediates fell below critical levels. The reaction mixture was cooled to 16° C. and crystallization was induced with the addition of 1 g pure CBN as seed crystals. The resultant solid was collected by Buchner funnel filtration yielding 378 grams of crude product, CBN. The crude product was dissolved in 1000 mL ethyl acetate along with 175 mL of acetic anhydride and 300 mL of triethylamine. This mixture was heated to 40° C. and stirred for 4 hours. The mixture was cooled and washed with five 200 mL portions of aqueous solution containing 5% sodium thiosulfate and 5% sodium bicarbonate. The washed organic layer was stripped of its solvent by rotary evaporation and reconstituted in 1500 mL of hot ethanol. The mixture was stirred and allowed to cool, and the resulting solid was collected by Buchner funnel filtration and washed with cold ethanol, yielding 350 grams (0.99 mol) of CBN—OAc. Final product quality was confirmed at >99% pure by GCMS analysis.

HRMS data was collected on CBN—OAc shown in Table 7 below.

TABLE 7

| Formula | Species | Structure | Calculated Mass (M/Z) | Observed Mass (M/Z) | Calculated Error (PPM) |
| --- | --- | --- | --- | --- | --- |
| $C_{23}H_{28}O_3$ | Molecule | 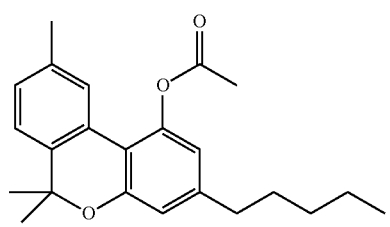 [SMILES: CCCCCc1cc(OC(C)=O)c2c(c1)OC(C)(C)c1ccc(C)cc1-2] | 352.2038 | | |

TABLE 7-continued

| Formula | Species | Structure | Calculated Mass (M/Z) | Observed Mass (M/Z) | Calculated Error (PPM) |
|---|---|---|---|---|---|
| $C_{23}H_{29}O_3^+$ | $[M + H]^+$ ion | 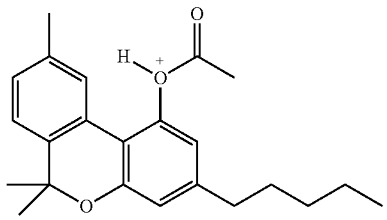 | 353.2111 | 353.2103 | 2.26 |
| $C_{23}H_{28}O_3 + Na^+$ | $[M + Na]^+$ adduct | 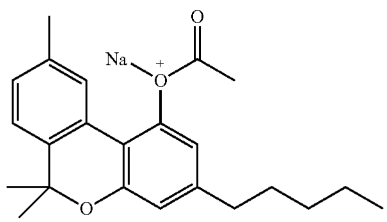 | 375.1931 | 375.1921 | 2.67 |

Example 3: Synthesis of Cannabivarinol (CBNV) and Acetylcannabivarinol (CBNV—OAc)

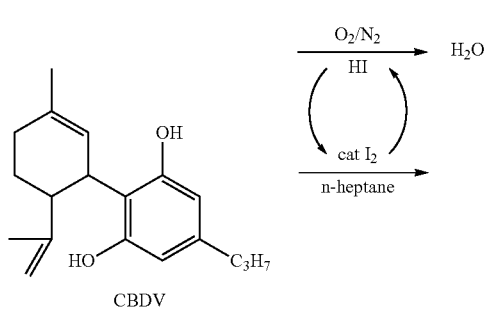

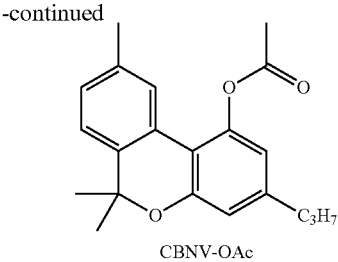

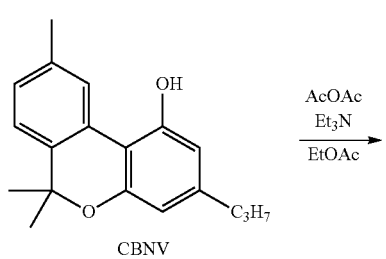

CBDV (50 g, 0.17 mol) was charged to a glass reactor equipped with magnetic stirrer and a temperature controller. Elemental iodine (0.67 g, 2.6 mMol, 1.5% cat mol eq) was charged to the reactor along with 250 mL of n-heptane to form a mixture. This mixture was stirred together at 90° C. Compressed 5% $O_2$ was added to the mixture at a rate of 50 milliliters per minute via gas dispersion tube. The mixture was heated for 240 hours until GCMS analysis showed that reaction intermediates fell below critical levels. The reaction mixture was cooled to 5° C. and crystallization was induced with the addition of 0.1 g pure CBNV as seed crystals. The resultant solid was collected by Buchner funnel filtration yielding 20.2 grams of crude product, CBNV. The crude product was dissolved in 100 mL ethyl acetate along with 20 mL of acetic anhydride and 30 mL of triethylamine. This mixture was heated to 40° C. and stirred for 6 hours. The mixture was cooled and washed with five 50 mL portions of aqueous solution containing 5% sodium thiosulfate and 5% sodium bicarbonate. The washed organic layer was stripped of its solvent by rotary evaporation and reconstituted in 100 mL of hot ethanol. The mixture was stirred and allowed to cool, and the resulting solid was collected by Buchner funnel filtration and washed with cold ethanol, yielding 18.5 grams (0.06 mol) of CBNV—OAc. The quality of the final product was confirmed at >99% pure by GCMS analysis.

HRMS data was collected on CBNV shown in Table 8 below.

TABLE 8

| Formula | Species | Structure | Calculated Mass (M/Z) | Observed Mass (M/Z) | Calculated Error (PPM) |
| --- | --- | --- | --- | --- | --- |
| $C_{19}H_{22}O_2$ | Molecule | 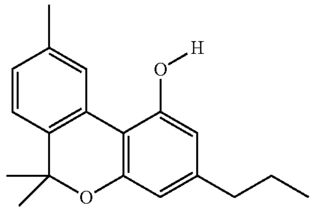 [SMILES: CCCc1cc(O)c2c(c1)OC(C)(C)c1ccc(C)cc1-2] | 282.1620 | | |
| $C_{19}H_{23}O_2^+$ | [M + H]$^+$ ion | 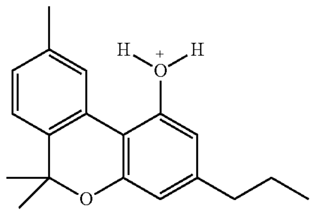 | 283.1693 | 283.1689 | 1.41 |
| $C_{19}H_{22}O_2$ + Na$^+$ | [M + Na]$^+$ adduct | 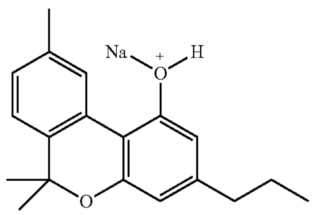 | 305.1512 | 305.1509 | 0.98 |

HRMS data was collected on CBNV—OAc shown in Table 9 below.

TABLE 9

| Formula | Species | Structure | Calculated Mass (M/Z) | Observed Mass (M/Z) | Calculated Error PPM) |
| --- | --- | --- | --- | --- | --- |
| $C_{21}H_{24}O_3$ | Molecule | 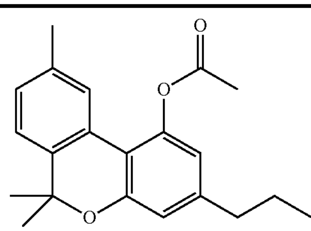 | 324.1725 | | |
| $C_{21}H_{25}O_3^+$ | [M + H]$^+$ ion | 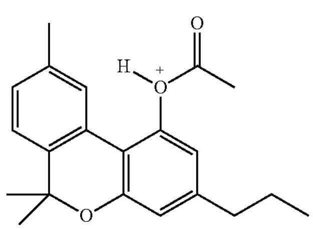 | 325.1798 | 325.1791 | 2.15 |
| $C_{21}H_{24}O_3$ + Na$^+$ | [M + Na]$^+$ adduct | 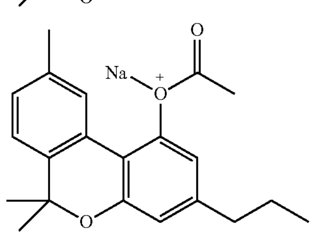 | 347.1618 | 347.1611 | 2.02 |

Although the disclosed inventive concepts include those defined in the attached claims, it should be understood that the inventive concepts can also be defined in accordance with the following embodiments.

EMBODIMENTS

In addition to the embodiments of the attached claims and the embodiments described above, the following numbered embodiments are also innovative.

Embodiment 1: A method of preparing cannabinol, or a pharmaceutically acceptable salt thereof, the method comprising:
admixing a catalyst, cannabidiol, and an oxidizing agent to form cannabinol, or a pharmaceutically acceptable salt thereof,
wherein the catalyst is $I_2$, $Br_2$, or $Cl_2$.

Embodiment 2. The method of embodiment 1, wherein the admixing comprises:
(a) reacting the catalyst and the cannabidiol to form tetrahydrocannabinol; and
(b) reacting the tetrahydrocannabinol, the catalyst, and the oxidizing agent to form the cannabinol, or a pharmaceutically acceptable salt thereof.

Embodiment 3. The method of embodiment 1 or 2, wherein the catalyst is $I_2$.

Embodiment 4. The method of embodiment 2 or 3, wherein reacting the catalyst and the cannabidiol is performed at a temperature of about 35° C. to about 200° C., about 50° C. to about 150° C., about 50° C. to about 100° C., or less than about 100° C.

Embodiment 5. The method of any one of embodiments 1-4, wherein the admixing is done in the presence of a solvent.

Embodiment 6. The method of embodiment 5, wherein the solvent comprises one or more of benzene, toluene, xylenes, mesitylene, anisole, acetonitrile, acetic acid, acetic anhydride, heptane, cyclohexane, pyridine, chloroform, isopropyl acetate, dimethyl sulfoxide, dimethylformamide, dimethylacetamide, N-methylpyrrolidone, and chlorobenzene.

Embodiment 7. The method of any one of embodiments 1-6, wherein the catalyst is present in an amount of about 10 mol % or less, about 5 mol % or less, or about 1 mol % or less, based on the total mols of cannabidiol.

Embodiment 8. The method of any one of embodiments 2-7, wherein the reacting the tetrahydrocannabinol, the catalyst, and the oxidizing agent is performed at a temperature in a range of about 50° C. to about 250° C., about 75° C. to about 200° C., about 120° C. to about 170° C., or less than about 150° C.

Embodiment 9. The method of any one of embodiments 1-8, wherein the oxidizing agent comprises one or more of $O_2$, $S_8$, benzoquinone, chloranil, hydrogen peroxide, peracetic acid, diacetyl peroxide, ditertbutyl peroxide, dicumyl peroxide, peroxybenzoic acid, benzoyl peroxide, and dimethyl sulfoxide.

Embodiment 10. The method of any one of embodiments 1-9, wherein the oxidizing agent comprises $O_2$ and an inert gas.

Embodiment 11. The method of any one of embodiments 1-10, wherein the oxidizing agent comprises $O_2$ and $N_2$.

Embodiment 12. The method of any one of embodiments 1-11, wherein the oxidizing agent comprises $O_2$ and the $O_2$ is present in an amount of less than about 25 wt %, less than about 20 wt %, less than about 15 wt %, about 10 wt % to about 20 wt %, or about 1 wt % to about 10 wt %, based on the total weight of the oxidizing agent.

Embodiment 13. The method of any one of embodiments 2-12, wherein step (a) and step (b) are performed in situ.

Embodiment 14. The method of any one of embodiments 1-14, wherein the method is performed in a single vessel.

Embodiment 15. The method of any one of embodiments 1-14, wherein the method further forms cannabifuran, and wherein the cannabifuran is formed in an amount of less than about 5 mol %, based on the total mols of cannabinol, or a pharmaceutically acceptable salt thereof.

Embodiment 16. The method of any one of embodiments 1-15, comprising crystallizing the cannabinol, or a pharmaceutically acceptable salt thereof.

Embodiment 17. The method of any one of embodiments 1-16, wherein the cannabinol, or a pharmaceutically acceptable salt thereof, has a purity of about 90% or more, about 95% or more, or about 99% or more.

Embodiment 18. The method of any one of embodiments 1-17, wherein the cannabinol, or a pharmaceutically acceptable salt thereof, is substantially free of $\Delta^{(9,10)}$-tetrahydrocannabinol.

Embodiment 19. The method of any one of embodiments 1-18, wherein the cannabinol, or a pharmaceutically acceptable salt thereof, is substantially free of $\Delta^{(8,9)}$-tetrahydrocannabinol and $\Delta^{(9,10)}$-tetrahydrocannabinol.

Embodiment 20. The method of any one of embodiments 1-19, further comprising: admixing the cannabinol, or a pharmaceutically acceptable salt thereof, with a dehydrating agent and acetic acid to form a mixture comprising acetylcannabinol, or a pharmaceutically acceptable salt thereof.

Embodiment 21. The method of embodiment 20, wherein the dehydrating agent comprises one or more of acetic anhydride, phosphoric acid, sulfuric acid, sodium bisulfite, phosphorus pentoxide, and polyphosphoric acid.

Embodiment 22. The method of embodiment 20, wherein the mixture further forms acetylcannabifuran, or a pharmaceutically acceptable salt thereof, wherein the acetylcannabifuran, or a pharmaceutically acceptable salt thereof, is formed in an amount of less than about 5 mol %, based on the total mols of acetylcannabinol.

Embodiment 23. A method of preparing cannabinol, or a pharmaceutically acceptable salt thereof, the method comprising:
admixing a catalyst, an oxidizing agent, and tetrahydrocannabinol to form cannabinol, or a pharmaceutically acceptable salt thereof,
wherein the catalyst is $I_2$, $Br_2$, or $Cl_2$.

Embodiment 24. The method of embodiment 23, wherein the tetrahydrocannabinol is prepared by a process comprising:
admixing the catalyst and cannabidiol to form the tetrahydrocannabinol.

Embodiment 25. The method of 24, wherein admixing the catalyst and the cannabidiol is performed at a temperature of about 35° C. to about 200° C., about 50° C. to about 150° C., about 50° C. to about 100° C., or about less than about 100° C.

Embodiment 26. A method of preparing cannabinol, or a pharmaceutically acceptable salt thereof, the method comprising:
(a) admixing cannabidiol and a catalyst to form a mixture of $\Delta^{(8,9)}$-tetrahydrocannabinol and $\Delta^{(9,10)}$-tetrahydrocannabinol; and
(b) admixing the mixture and an oxidizing agent to form the cannabinol, or a pharmaceutically acceptable thereof, wherein the catalyst is $I_2$ and the $I_2$ is present in an amount of less than about 5 mol %, based on the total mols of the cannabidiol.

Embodiment 27. The method of any one of embodiments 23-26, wherein the catalyst is present in an amount of less than about 1 mol %, based on the total mols of the cannabidiol.

Embodiment 28. The method of any one of embodiments 23-27, wherein the cannabinol has a purity of about 90% or more, about 95% or more, or about 99% or more.

Embodiment 29. A method of preparing acetylcannabinol, or a pharmaceutically acceptable salt thereof, the method comprising:
admixing cannabidiol, an oxidizing agent, $I_2$, and acetic acid to form a mixture comprising cannabinol, or a pharmaceutically acceptable salt thereof, wherein the $I_2$ is present in an amount of less than about 5 mol %, based on the total mols of cannabidiol; and
admixing the mixture with a dehydrating agent to form acetylcannabinol, or a pharmaceutically acceptable salt thereof.

Embodiment 30. The method of embodiment 29, wherein the $I_2$ is present in an amount of less than about 1 mol %, based on the total mols of cannabidiol.

Embodiment 31. The method of embodiment 29 or 30, wherein the acetylcannabinol has a purity of about 90% or more, about 95% or more, or about 99% or more.

Embodiment 32. A method of preparing a compound of Formula (I):

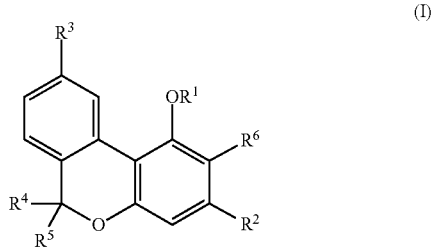

(I)

or a pharmaceutically acceptable salt thereof, wherein:
$R^1$ is hydrogen, $C_1$-$C_{10}$ alkyl, C(=O)—($C_1$-$C_{10}$ alkyl), or Si($C_1$-$C_{10}$ alkyl)$_3$;
$R^2$ is hydrogen or $C_1$-$C_{10}$ alkyl;
$R^3$ is hydrogen, $C_1$-$C_6$ alkyl, or $C_1$-$C_6$ hydroxyalkyl;
$R^4$ is hydrogen, $C_1$-$C_{10}$ alkyl, or $C_2$-$C_{10}$ alkenyl;
$R^5$ is hydrogen, $C_1$-$C_{10}$ alkyl, or $C_2$-$C_{10}$ alkenyl; and
$R^6$ is hydrogen, $C_1$-$C_6$ alkyl, C(=O)(OH), or C(=O)—($C_1$-$C_6$ alkyl);
the method comprising:
admixing a catalyst, an oxidizing agent, and a compound of Formula (II):

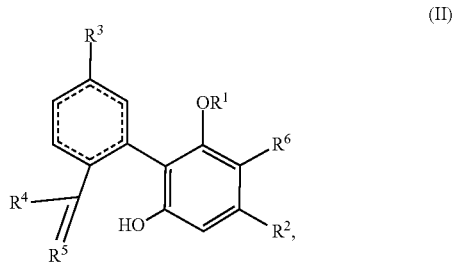

(II)

wherein ═══ each is independently a single bond or a double bond, and wherein only one ═══ is a double bond, to form a compound of Formula (I), or a pharmaceutically acceptable salt thereof,
wherein the catalyst is $I_2$, $Br_2$, or $Cl_2$.

Embodiment 33. The method of embodiment 32, wherein the admixing comprises:
(a) reacting the catalyst and the compound of Formula (II) to form a compound of Formula (III):

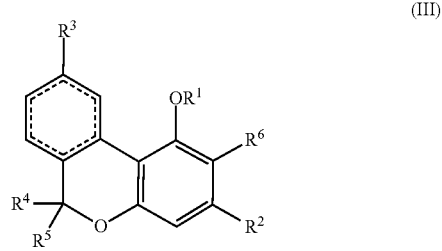

(III)

wherein each ═══ is independently a single bond or a double bond, and wherein only one ═══ is a double bond; and
(b) reacting the compound of Formula (III), the catalyst, and the oxidizing agent to form the compound of Formula (I), or a pharmaceutically acceptable salt thereof.

Embodiment 34. A method of preparing a compound of Formula (I):

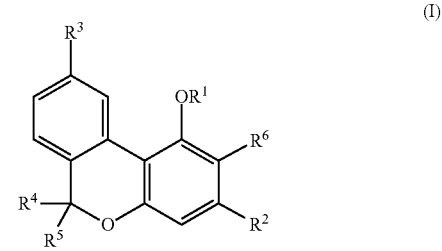

(I)

or a pharmaceutically acceptable salt thereof, wherein:
$R^1$ is hydrogen, $C_1$-$C_{10}$ alkyl, or C(=O)—($C_1$-$C_{10}$ alkyl);
$R^2$ is hydrogen or $C_1$-$C_{10}$ alkyl;
$R^3$ is hydrogen, $C_1$-$C_6$ alkyl, or $C_1$-$C_6$ hydroxyalkyl;
$R^4$ is hydrogen, $C_1$-$C_{10}$ alkyl, or $C_2$-$C_{10}$ alkenyl;
$R^5$ is hydrogen, $C_1$-$C_{10}$ alkyl or $C_2$-$C_{10}$ alkenyl; and
$R^6$ is hydrogen, $C_1$-$C_6$ alkyl, C(=O)(OH), or C(=O)—($C_1$-$C_6$ alkyl);
the method comprising:
admixing a catalyst, an oxidizing agent, and a compound of Formula (III)

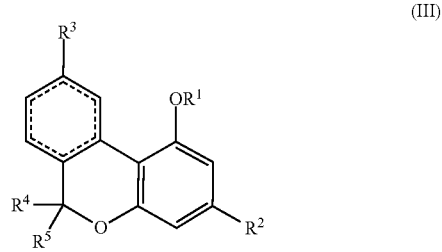

(III)

to form the compound of Formula (I), or a pharmaceutically acceptable salt thereof,
wherein each ≔ is independently a single bond or a double bond, and wherein only one ≔ is a double bond; and
wherein the catalyst is $I_2$, $Br_2$, or $Cl_2$.

Embodiment 35. The method of embodiment 34, wherein the compound of Formula (III) is prepared by a process comprising:
admixing the catalyst and a compound of Formula (II):

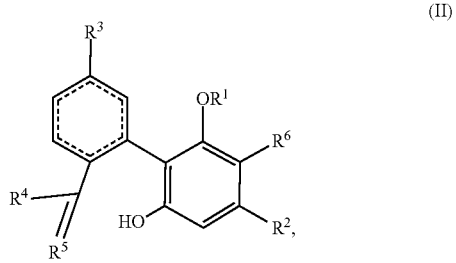

to form the compound of Formula (III),
wherein each ≔ is independently a single bond or a double bond, and wherein only one ≔ is a double bond.

Embodiment 36. The method of any one of embodiments 32-35, wherein $R^1$ is hydrogen or $C_1$-$C_3$ alkyl.

Embodiment 37. The method of any one of embodiments 32-36, wherein $R^1$ is hydrogen.

Embodiment 38. The method of any one of embodiments 32-35, wherein $R^1$ is C(=O)—($C_1$-$C_3$ alkyl).

Embodiment 39. The method of any one of embodiments 32-36, wherein $R^2$ is $C_1$-$C_6$alkyl.

Embodiment 40. The method of any one of embodiments 32-39, wherein $R^2$ is $C_5$ alkyl.

Embodiment 41. The method of any one of embodiments 32-40, wherein $R^3$ is $C_1$-$C_3$ alkyl.

Embodiment 42. The method of any one of embodiments 32-41, wherein $R^3$ is methyl.

Embodiment 43. The method of any one of embodiments 32-40, wherein $R^3$ is $C_1$-$C_3$ hydroxyalkyl.

Embodiment 44. The method of any one of embodiments 32-40, wherein $R^3$ is $CH_2OH$.

Embodiment 45. The method of any one of embodiments 32-44, wherein $R^4$ is $C_1$-$C_6$alkyl.

Embodiment 46. The method of any one of embodiments 32-45, wherein $R^4$ is methyl.

Embodiment 47. The method of any one of embodiments 32-46, wherein $R^5$ is $C_1$-$C_6$ alkyl.

Embodiment 48. The method of any one of embodiments 32-47, wherein $R^5$ is methyl.

Embodiment 49. The method of any one of embodiments 32-48, wherein the catalyst is $I_2$.

Embodiment 50. The method of any one of embodiments 33 or 36-49, wherein the reacting of the catalyst and the compound of Formula (II) is performed at a temperature of about 35° C. to about 200° C., about 50° C. to about 150° C., about 50° C. to about 100° C., or less than 100° C.

Embodiment 51. The method of any one of embodiments 35-49, wherein the admixing of the catalyst and the compound of Formula (II) is performed at a temperature of about 35° C. to about 200° C., about 50° C. to about 150° C., about 50° C. to about 100° C., or less than about 100° C.

Embodiment 52. The method of any one of embodiments 32-51, wherein the admixing or the reacting is performed in a solvent.

Embodiment 53. The method of embodiment 52, wherein the solvent comprises one or more of benzene, toluene, xylenes, mesitylene, anisole, acetonitrile, acetic acid, acetic anhydride, heptane, cyclohexane, pyridine, chloroform, isopropyl acetate, dimethyl sulfoxide, dimethylformamide, dimethylacetamide, N-methylpyrrolidone, and chlorobenzene.

Embodiment 54. The method of any one of embodiments 32-53, wherein the catalyst is present in an amount of about 10 mol % or less, about 5 mol % or less, or about 1 mol % or less, based on the total mols of the compound of Formula (II) or the compound of Formula (III).

Embodiment 55. The method of any one of embodiments 33-51, wherein the admixing or the reacting of the compound of Formula (III), the catalyst, and the oxidizing agent is performed at a temperature of about 50° C. to about 250° C., about 75° C. to about 200° C., about 120° C. to about 170° C., or less than about 150° C.

Embodiment 56. The method of any one of embodiments 32-55, wherein the oxidizing agent comprises one or more of $O_2$, $S_8$, benzoquinone, chloranil, hydrogen peroxide, peracetic acid, diacetyl peroxide, ditertbutyl peroxide, dicumyl peroxide, peroxybenzoic acid, and benzoyl peroxide, and dimethyl sulfoxide.

Embodiment 57. The method of any one of embodiments 32-56, wherein the oxidizing agent comprises $O_2$ and an inert gas.

Embodiment 58. The method of any one of embodiments 32-57, wherein the oxidizing agent comprises $O_2$ and $N_2$.

Embodiment 59. The method of any one of embodiments 32-57, wherein the oxidizing agent comprises $O_2$ and the $O_2$ is present in an amount of less than about 25 wt %, less than about 20 wt %, less than about 15 wt %, or about 10 wt % to about 20 wt %, based on the total weight of the oxidizing agent.

Embodiment 60. The method of embodiment 33, wherein step (a) and step (b) are performed in situ.

Embodiment 61. The method of any one of embodiments 32-60, wherein the method is performed in a single vessel.

Embodiment 62. The method of any one of embodiments 32-61, wherein the method further forms a compound of Formula (IV):

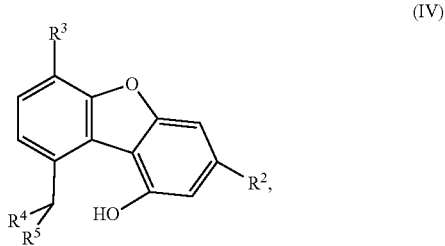

or a pharmaceutically acceptable salt thereof, wherein the compound of Formula (IV), or a pharmaceutically acceptable salt thereof, is formed in an amount of less than about 50 mol %, based on the total mols of the compound of Formula (I), or a pharmaceutically acceptable salt thereof.

Embodiment 63. The method of any one of embodiments 32-62, comprising crystallizing the compound of Formula (I), or a pharmaceutically acceptable salt thereof.

Embodiment 64. The method of any one of embodiments 32-63, wherein the compound of Formula (I), or a pharmaceutically acceptable salt thereof, has a purity of at least about 90%, at least about 95%, or at least about 99%.

Embodiment 65. The method of any one of embodiments 33-64, wherein the compound of Formula (I), or a pharmaceutically acceptable salt thereof, is substantially free of the compound of Formula (III).

Embodiment 66. The method of any one of embodiments 32-64, wherein the compound of Formula (I), or a pharmaceutically acceptable salt thereof, is substantially free of $\Delta^{(8,9)}$-tetrahydrocannabinol and $\Delta^{(9,10)}$-tetrahydrocannabinol.

Embodiment 67. The method of any one of embodiments 32-66, further comprising:
admixing the compound of Formula (I), or a pharmaceutically acceptable salt thereof, wherein $R^1$ is hydrogen, with a dehydrating agent and acetic acid to form a compound of Formula (I) wherein $R^1$ is C(=O)(Me).

Embodiment 68. The method of embodiment 67, wherein the dehydrating agent comprises one or more of acetic anhydride, phosphoric acid, sulfuric acid, sodium bisulfite, phosphorus pentoxide, and polyphosphoric acid.

Embodiment 69. The method of embodiment 67 or 68, comprising forming the compound of Formula (IV), or a pharmaceutically acceptable salt thereof, wherein $R^1$ is C(=O)(Me).

Embodiment 70. The method of embodiment 38, wherein the compound of Formula (IV), or a pharmaceutically acceptable salt thereof, is formed in an amount of less than about 5 mol %, based on the total mols of the compound of Formula (V).

Embodiment 71. The method of any one of embodiments 32-37 or 39-70, wherein the compound of Formula (I) is

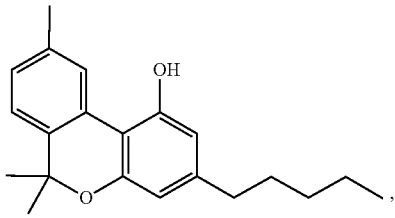 [SMILES: CCCCCc1cc(O)c2c(c1)OC(C)(C)c1ccc(C)cc1-2]

or a pharmaceutically acceptable salt thereof.

Embodiment 72. The method of any one of embodiments 32-37 or 39-66, wherein the method produces a mixture of

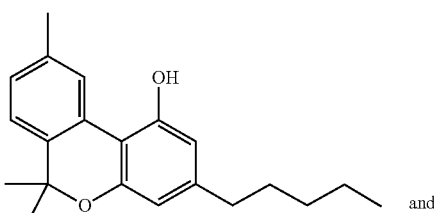 and

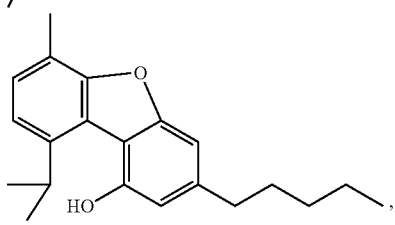

or pharmaceutically acceptable salts thereof.

Embodiment 73. The method of any one of embodiments 32-39, or 41-70, wherein the compound of Formula (I) is

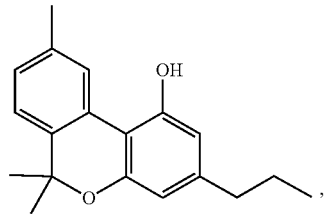 [SMILES: CCCc1cc(O)c2c(c1)OC(C)(C)c1ccc(C)cc1-2]

or a pharmaceutically acceptable salt thereof.

Embodiment 74. The method of any one of embodiments 32-37, 39-65, or 73, wherein the method forms

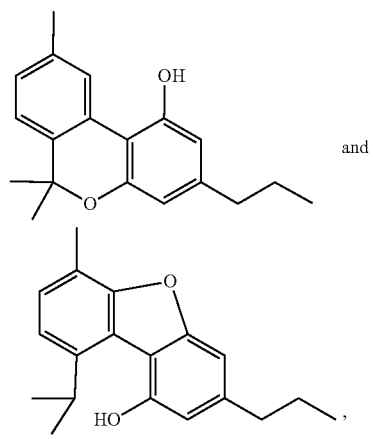

or pharmaceutically acceptable salts thereof.

Embodiment 75. The method of any one of embodiments 67-71, wherein the compound of Formula (V) is

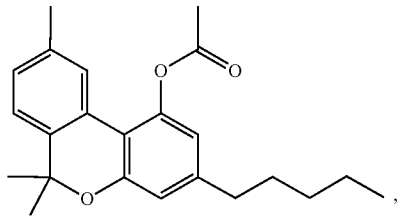 [SMILES: CCCCCc1cc(OC(C)=O)c2c(c1)OC(C)(C)c1ccc(C)cc1-2]

or a pharmaceutically acceptable salt thereof.

Embodiment 76. The method of any one of embodiments 67-69 or 73, wherein the compound of Formula (V) is

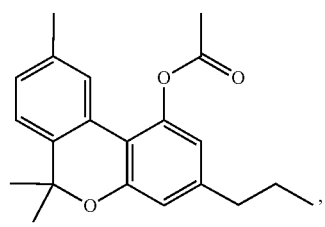 [SMILES: CCCc1cc(OC(C)=O)c2c(c1)OC(C)(C)c1ccc(C)cc1-2]

or a pharmaceutically acceptable salt thereof.

Embodiment 77. The method of any one of embodiments 33-37 or 39-76, wherein the compound of Formula (III) is

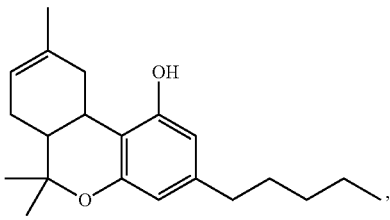 [SMILES: CCCCCc1cc(O)c2c(c1)OC(C)(C)C1CC=C(C)CC21]

or a pharmaceutically acceptable salt thereof.

Embodiment 78. The method of any one of embodiments 33-37 or 39-77, wherein the compound of Formula (III) is a mixture of

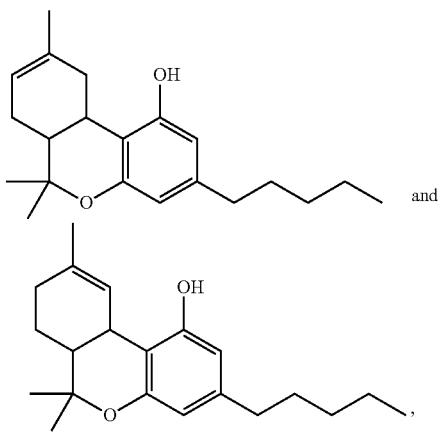

or pharmaceutically acceptable salts thereof.

Embodiment 79. A method of preparing cannabinol, or a pharmaceutically acceptable salt thereof, the method comprising:
(a) admixing cannabidiol and a catalytic amount of $I_2$ to form a mixture of $\Delta^{(8,9)}$-tetrahydrocannabinol and $\Delta^{(9,10)}$-tetrahydrocannabinol; and
(b) admixing the mixture and an oxidizing agent to form the cannabinol, or a pharmaceutically acceptable salt thereof.

Embodiment 80. The method of embodiments 79, wherein the catalytic amount of $I_2$ is less than about 5 mol %, based on the total mols of the cannabidiol.

Embodiment 81. The method of embodiments 79 or 80, wherein the catalytic amount of $I_2$ is less than about 1 mol %, based on the total mols of the cannabidiol.

Embodiment 82. The method of any one of embodiments 79-81, wherein the cannabinol is formed in about 50 mol % or more yield, based on the total mols of cannabidiol.

Embodiment 83. The method of any one of embodiments 79-82, wherein the oxidizing agent comprise one or more of $O_2$, $S_8$, benzoquinone, chloranil, hydrogen peroxide, peracetic acid, diacetyl peroxide, ditertbutyl peroxide, dicumyl peroxide, peroxybenzoic acid, and benzoyl peroxide, and dimethyl sulfoxide.

Embodiment 84. The method of any one of embodiments 79-83, wherein the admixing the cannabidiol and the catalytic amount of $I_2$ occurs at a temperature of about 35° C. to about 200° C., about 50° C. to about 150° C., about 50° C. to about 100° C., or less than about 100° C.

Embodiment 85. The method of any one of embodiments 79-84, wherein the admixing the mixture and the oxidizing agent occurs at a temperature of about 50° C. to about 250° C., about 75° C. to about 200° C., about 120° C. to about 170° C., or less than about 150° C.

Embodiment 86. The method of any one of embodiments 79-85, wherein the admixing is done in the presence of a solvent.

Embodiment 87. The method of embodiment 55, wherein the solvent comprises one or more of benzene, toluene, xylenes, mesitylene, anisole, acetonitrile, acetic acid, acetic anhydride, heptane, cyclohexane, pyridine, chloroform, isopropyl acetate, dimethyl sulfoxide, dimethylformamide, dimethylacetamide, N-methylpyrrolidone, and chlorobenzene.

Embodiment 88. The method of any one of embodiments 79-87, wherein the cannabinol, or a pharmaceutically acceptable salt thereof, is substantially free of $\Delta^{(8,9)}$-tetrahydrocannabinol and $\Delta^{(9,10)}$-tetrahydrocannabinol.

Embodiment 89. The method of any one of embodiments 37-88, further comprising crystallizing the cannabinol, or a pharmaceutically acceptable salt thereof.

Embodiment 90. The method of any one of embodiments 37-89, wherein the cannabinol, or a pharmaceutically acceptable salt thereof has a purity of at least about 90%, at least about 95%, or at least about 99%.

Embodiment 91. A method of preparing cannabinol, or a pharmaceutically acceptable salt thereof, the method comprising:
admixing cannabidiol with $O_2$ and a catalytic amount of $I_2$ to form cannabinol, or a pharmaceutically acceptable salt thereof.

Embodiment 92. The method of embodiment 91, wherein the $O_2$ is present in a gaseous mixture comprising an inert gas and the $O_2$ is in an amount of less than 25 wt %, less than 20 wt %, less than 15 wt %, or 10 wt % to 20 wt %, based on the total weight of the gaseous mixture.

Embodiment 93. The method of embodiment 91 or 92, wherein the cannabinol, or a pharmaceutically acceptable salt thereof, has a purity of 90% or more, 95% or more, or 99% or more.

Embodiment 94. A method of preparing cannabinol acetate, or a pharmaceutically acceptable salt thereof, the method comprising:
admixing cannabidiol, $O_2$, a catalytic amount of $I_2$, and acetic acid to form a mixture comprising cannabinol; and
admixing the mixture with a dehydrating agent to form cannabinol acetate, or a pharmaceutically acceptable salt thereof.

Embodiment 95. The method of embodiment 94, wherein the $O_2$ is present in a gaseous mixture comprising an inert gas and the $O_2$ is in an amount of less than 25 wt %, less than 20 wt %, less than 15 wt %, or 10 wt % to 20 wt %, based on the total weight of the gaseous mixture.

Embodiment 96. The method of embodiment 94 or 95, wherein the cannabinol acetate, or a pharmaceutically acceptable salt thereof, is formed in a 50 mol % or more yield, based on the total mols of the cannabidiol.

Embodiment 97. The method of any one of embodiments 94-96, wherein the dehydrating agent comprises one or more of acetic anhydride, phosphoric acid, sulfuric acid, sodium bisulfite, phosphorus pentoxide, and polyphosphoric acid.

Embodiment 98. The method of any one of embodiments 94-97, wherein the method is performed in a single vessel.

Embodiment 99. The method of any one of embodiments 94-97, wherein the method is performed in a single vessel without purifying the mixture comprising cannabinol prior to admixing the mixture with the dehydrating agent.

Embodiment 100. A method of preparing a mixture of compound (1) and compound (2):

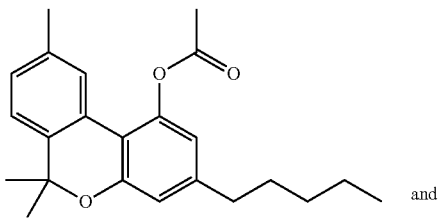
(1)

and

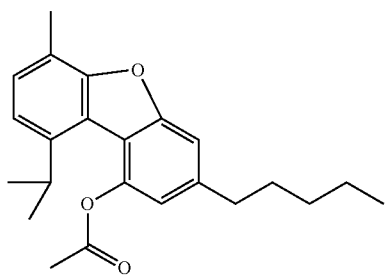
(2)

or pharmaceutically acceptable salts thereof,
the method comprising:
(a) admixing a catalyst, an oxidizing agent, and compound (3):

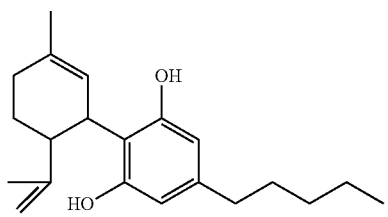
(3)

to form compound (4):

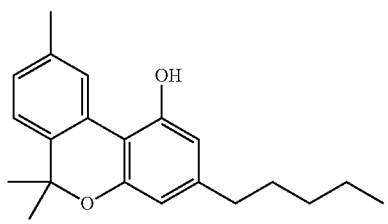
(4)

in a single vessel; and
(b) in the single vessel, admixing a dehydrating agent, acetic acid and compound (4)
to form the mixture of compound (1) and compound (2), or pharmaceutically acceptable salts thereof;
wherein the catalyst is $I_2$, $Br_2$, or $Cl_2$.

Embodiment 101. A method of preparing cannabinol, or a pharmaceutically acceptable salt thereof, the method comprising:

admixing cannabidiol, $O_2$, $I_2$, and a solvent to form a mixture comprising cannabinol, or a pharmaceutically acceptable salt thereof, and cannabifuran;

wherein the $I_2$ is present in an amount of about 10 mol % or less, based on the total mols of the cannabidiol;

wherein the cannabinol, or a pharmaceutically acceptable salt thereof, has a purity of at least about 90%; and wherein the cannabifuran is present in the mixture in an amount of about 10 mol % or less, based on the total mols of cannabinol, or a pharmaceutically acceptable salt thereof.

Embodiment 102. The method of embodiment 101, wherein the cannabinol, or a pharmaceutically acceptable salt thereof, is substantially free of $\Delta^{(8,9)}$-tetrahydrocannabinol and $\Delta^{(9,10)}$-tetrahydrocannabinol.

Embodiment 103. A composition comprising cannabinol, or a pharmaceutically acceptable salt thereof, and cannabifuran, wherein the cannabinol or a pharmaceutically acceptable salt thereof, and cannabifuran are present in a ratio of 100:1 to 1:1, respectively.

Embodiment 104. A composition comprising cannabivarin, or a pharmaceutically acceptable salt thereof, and cannabifuranvarin, wherein the cannabinol and the cannabifuran are present in a ratio of 100:1 to 1:1, respectively.

Although this disclosure contains many specific embodiment details, these should not be construed as limitations on the scope of the subject matter or on the scope of what may be claimed, but rather as descriptions of features that may be specific to particular embodiments. Certain features that are described in this disclosure in the context of separate embodiments can also be implemented, in combination, in a single embodiment. Conversely, various features that are described in the context of a single embodiment can also be implemented in multiple embodiments, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular embodiments of the subject matter have been described. Other embodiments, alterations, and permutations of the described embodiments are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results.

Accordingly, the previously described example embodiments do not define or constrain this disclosure. Other changes, substitutions, and alterations are also possible without departing from the spirit and scope of this disclosure.

What is claimed is:

1. A method of preparing a compound of Formula (I):

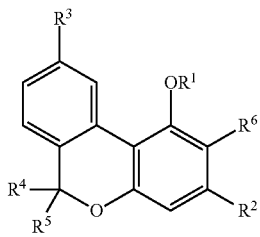

(I)

or a pharmaceutically acceptable salt thereof, wherein:
$R^1$ is hydrogen, $C_1$-$C_{10}$ alkyl, C(=O)—($C_1$-$C_{10}$ alkyl), or Si($C_1$-$C_{10}$ alkyl)$_3$;
$R^2$ is hydrogen or $C_1$-$C_{10}$ alkyl;
$R^3$ is hydrogen, $C_1$-$C_6$ alkyl, or $C_1$-$C_6$ hydroxyalkyl;
$R^4$ is hydrogen, $C_1$-$C_{10}$ alkyl, or $C_2$-$C_{10}$ alkenyl;
$R^5$ is hydrogen, $C_1$-$C_{10}$ alkyl, or $C_2$-$C_{10}$ alkenyl; and
$R^6$ is hydrogen, $C_1$-$C_6$ alkyl, C(=O)(OH), or C(=O)—($C_1$-$C_6$ alkyl);

the method comprising:
admixing a catalyst, an oxidizing agent, and a compound of Formula (II):

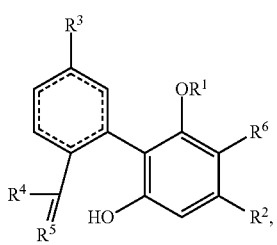

(II)

wherein each ≡ is independently a single bond or a double bond, and wherein only one ≡ is a double bond, to form a compound of Formula (I), or a pharmaceutically acceptable salt thereof,
wherein the catalyst is $I_2$, $Br_2$, or $Cl_2$; and
the oxidizing agent comprises one or more of $O_2$, $S_8$, benzoquinone, chloranil, hydrogen peroxide, peracetic acid, diacetyl peroxide, ditertbutyl peroxide, dicumyl peroxide, peroxybenzoic acid, benzoyl peroxide, and dimethyl sulfoxide.

2. The method of claim 1, wherein the admixing comprises:
(a) reacting the catalyst and the compound of Formula (II) to form a compound of Formula (III):

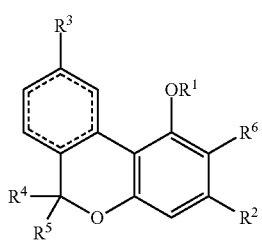

(III)

wherein each ≡ is independently a single bond or a double bond, and wherein only one ≡ is a double bond; and (b) reacting the compound of Formula (III), the catalyst, and the oxidizing agent to form the compound of Formula (I), or a pharmaceutically acceptable salt thereof.

3. A method of preparing a compound of Formula (I):

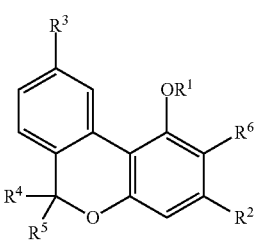

(I)

or a pharmaceutically acceptable salt thereof, wherein:
$R^1$ is hydrogen, $C_1$-$C_{10}$ alkyl, or C(=O)—($C_1$-$C_{10}$ alkyl);
$R^2$ is hydrogen or $C_1$-$C_{10}$ alkyl;
$R^3$ is hydrogen, $C_1$-$C_6$ alkyl, or $C_1$-$C_6$ hydroxyalkyl;
$R^4$ is hydrogen, $C_1$-$C_{10}$ alkyl, or $C_2$-$C_{10}$ alkenyl;
$R^5$ is hydrogen, $C_1$-$C_{10}$ alkyl or $C_2$-$C_{10}$ alkenyl; and
$R^6$ is hydrogen, $C_1$-$C_6$ alkyl, C(=O)(OH), or C(=O)—($C_1$-$C_6$ alkyl);

the method comprising:
admixing a catalyst, an oxidizing agent, and a compound of Formula (III)

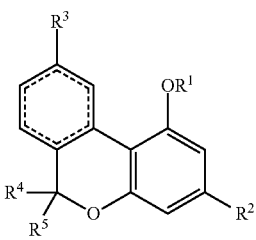

(III)

to form the compound of Formula (I), or a pharmaceutically acceptable salt thereof,
wherein each ≡ is independently a single bond or a double bond, and wherein only one ≡ is a double bond; and wherein the catalyst is $I_2$, $Br_2$, or $Cl_2$; and the oxidizing agent comprises one or more of $O_2$, $S_8$, benzoquinone, chloranil, hydrogen peroxide, peracetic acid, diacetyl peroxide, ditertbutyl peroxide, dicumyl peroxide, peroxybenzoic acid, benzoyl peroxide, and dimethyl sulfoxide.

4. The method of claim 3, wherein the compound of Formula (III) is prepared by a process comprising:
admixing the catalyst and a compound of Formula (II):

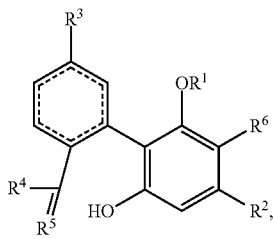

(II)

to form the compound of Formula (III),
wherein each ⚌ is independently a single bond or a double bond, and wherein only one ⚌ is a double bond.

5. The method of claim 3, wherein $R^1$ is hydrogen or $C_1$-$C_3$ alkyl.

6. The method of claim 3, wherein $R^1$ is C(=O)—($C_1$-$C_3$ alkyl).

7. The method of claim 3, wherein $R^2$ is $C_1$-$C_6$ alkyl.

8. The method of claim 3, wherein $R^3$ is $C_1$-$C_3$ alkyl.

9. The method of claim 3, wherein $R^3$ is $C_1$-$C_3$ hydroxyalkyl.

10. The method of claim 3, wherein $R^4$ is $C_1$-$C_6$ alkyl.

11. The method of claim 3, wherein $R^5$ is $C_1$-$C_6$ alkyl.

12. The method of claim 3, wherein the catalyst is $I_2$.

13. The method of claim 3, wherein the admixing of the catalyst and the compound of Formula (III) is performed at a temperature of about 35° C. to about 200° C.

14. The method of claim 4, wherein the admixing of the catalyst and the compound of Formula (II) is performed at a temperature of about 35° C. to about 200° C.

15. The method of claim 3, wherein the admixing is performed in an organic solvent.

16. The method of claim 3, wherein the catalyst is present in an amount of about 10 mol % or less, based on the total mols of the compound of Formula (III).

17. The method of claim 3, wherein the admixing of the compound of Formula (III), the catalyst, and the oxidizing agent is performed at a temperature of about 50° C. to about 250° C.

18. The method of claim 3, wherein the oxidizing agent comprises $O_2$, wherein the $O_2$ is present in a gaseous mixture that comprises an inert gas.

19. The method of claim 3, wherein the oxidizing agent comprises $O_2$ and the $O_2$ is present in an amount of less than about 25 wt %, based on the total weight of the oxidizing agent.

20. The method of claim 3, wherein the method further forms a compound of Formula (IV):

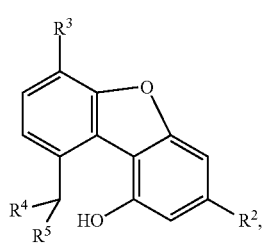

(IV)

or a pharmaceutically acceptable salt thereof,
wherein the compound of Formula (IV), or a pharmaceutically acceptable salt thereof, is formed in an amount of less than about 50 mol %, based on the total mols of the compound of Formula (I), or a pharmaceutically acceptable salt thereof.

21. The method of claim 3, comprising crystallizing the compound of Formula (I), or a pharmaceutically acceptable salt thereof, wherein the crystallizing comprises:
dissolving the compound of Formula (I), or a pharmaceutically acceptable salt thereof, in an organic solvent to form a solution wherein the temperature is at least about 35° C.; and
cooling the solution to room temperature.

22. The method of claim 3, wherein the compound of Formula (I), or a pharmaceutically acceptable salt thereof, has a purity of at least about 90%.

23. The method of claim 3, wherein the compound of Formula (I), or a pharmaceutically acceptable salt thereof, is substantially free of $\Delta^{(8,9)}$-tetrahydrocannabinol and $\Delta^{(9,10)}$-tetrahydrocannabinol.

24. The method of claim 3, further comprising:
admixing the compound of Formula (I), or a pharmaceutically acceptable salt thereof, wherein $R^1$ is hydrogen, with a dehydrating agent and acetic acid to form a compound of Formula (I) wherein $R^1$ is C(=O)(Me).

25. The method of claim 24, wherein the dehydrating agent comprises one or more of acetic anhydride, phosphoric acid, sulfuric acid, sodium bisulfite, phosphorus pentoxide, and polyphosphoric acid.

26. The method of claim 3, wherein the compound of Formula (I) is

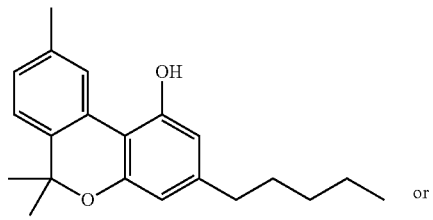 or

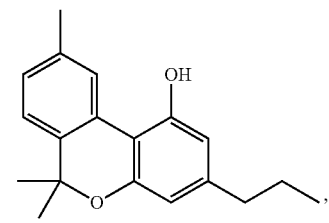, or a pharmaceutically acceptable salt thereof.

27. The method of claim 24, wherein the compound of Formula (I) is

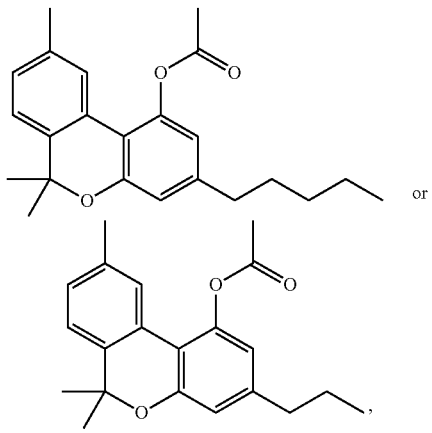

or

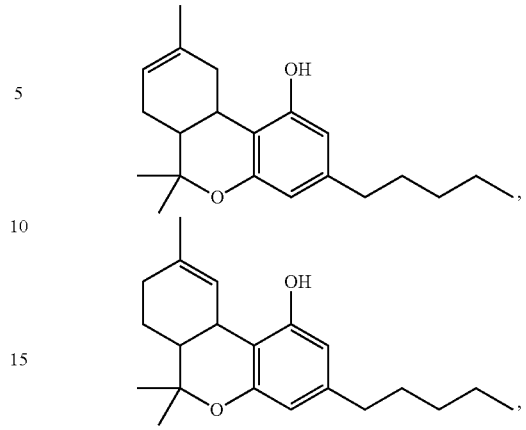

a pharmaceutically acceptable salt thereof, or a combination thereof.

or a pharmaceutically acceptable salt thereof.

28. The method of claim 3, wherein the compound of Formula (III) is

29. The method of claim 3, wherein the compound of Formula (I), or a pharmaceutically acceptable salt thereof, has a purity of at least about 95%.

* * * * *